United States Patent
Njar et al.

(10) Patent No.: US 10,793,525 B2
(45) Date of Patent: Oct. 6, 2020

(54) 13-CIS-RAMBA RETINAMIDES THAT DEGRADE MNKS FOR TREATING CANCER

(71) Applicant: UNIVERSITY OF MARYLAND, BALTIMORE, Baltimore, MD (US)

(72) Inventors: Vincent Njar, Glen Burnie, MD (US); Hannah Mbatia, Germantown, MD (US); Vidya Ramamurthy, Baltimore, MD (US); Senthilmurugan Ramalingam, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 322 days.

(21) Appl. No.: 15/528,317

(22) PCT Filed: Nov. 18, 2015

(86) PCT No.: PCT/US2015/061317
§ 371 (c)(1),
(2) Date: May 19, 2017

(87) PCT Pub. No.: WO2016/081589
PCT Pub. Date: May 26, 2016

(65) Prior Publication Data
US 2019/0002411 A1 Jan. 3, 2019

Related U.S. Application Data

(60) Provisional application No. 62/082,413, filed on Nov. 20, 2014.

(51) Int. Cl.
| | | |
|---|---|---|
| *A61K 31/4164* | (2006.01) | |
| *A61K 31/165* | (2006.01) | |
| *A61K 31/203* | (2006.01) | |
| *A61K 31/215* | (2006.01) | |
| *A61K 31/4406* | (2006.01) | |
| *A61K 31/505* | (2006.01) | |
| *A61K 31/4409* | (2006.01) | |
| *C07D 233/56* | (2006.01) | |
| *C07D 239/26* | (2006.01) | |
| *C07D 213/56* | (2006.01) | |
| *C07C 403/20* | (2006.01) | |
| *A61P 35/00* | (2006.01) | |
| *C07D 213/55* | (2006.01) | |

(52) U.S. Cl.
CPC .......... *C07D 233/56* (2013.01); *A61K 31/165* (2013.01); *A61K 31/203* (2013.01); *A61K 31/215* (2013.01); *A61K 31/4164* (2013.01); *A61K 31/4406* (2013.01); *A61K 31/4409* (2013.01); *A61K 31/505* (2013.01); *A61P 35/00* (2018.01); *C07C 403/20* (2013.01); *C07D 213/55* (2013.01); *C07D 213/56* (2013.01); *C07D 239/26* (2013.01); *C07C 2601/16* (2017.05)

(58) Field of Classification Search
None
See application file for complete search history.

(56) References Cited

U.S. PATENT DOCUMENTS

| 7,015,225 B1 | 3/2006 | Chen | |
| 7,265,143 B2 * | 9/2007 | Njar | ...................... C07C 323/61 514/396 |
| 2003/0162823 A1 | 8/2003 | Njar et al. | |

FOREIGN PATENT DOCUMENTS

WO 2010/036404 A2 4/2010

OTHER PUBLICATIONS

Extended European Search Report, dated Jun. 28, 2018, issued in counterpart European Patent Application No. 15860844.8 (in English; 5 pages).
Gediya et al., "Improved Synthesis of Histone Deacetylase Inhibitors (HDIs) (MS-275 and CI-994) and Inhibitory Effects of HDIs Alone or in Combination with RAMBAs or Retinoids on Growth of Human LNCaP Prostate Cancer Cells and Tumor Xenografts", Bioorganic & Medicinal Chemistry, vol. 16, No. 6, Mar. 15, 2008, pp. 3352-3360; cited in the International Search Report (in English; 22 pages).
Patel et al., "Novel retinoic acid metabolism blocking agents have potent inhibitory activities on human breast cancer cells and tumour growth", British Journal of Cancer, vol. 96, No. 8, 2007, pp. 1204-1215; cited in the International Search Report (in English; 12 pages).
International Search Report and Written Opinion dated Aug. 24, 2016, issued in counterpart international application No. PCT/US2015/061317 (in English; 16 pages).

\* cited by examiner

*Primary Examiner* — Samantha L Shterengarts
(74) *Attorney, Agent, or Firm* — Westerman, Hattori, Daniels & Adrian, LLP

(57) ABSTRACT

The synthesis and in vitro and in vivo anti-breast and anti-prostate cancers activities of novel C-4 heteroaryl 13-cis retinamides that modulate Mnk-eIF4E and AR signaling are discussed. In both breast and prostate cancer cell lines, these compounds induce Mnk1/2 degradation to substantially suppress eIF4E phosphorylation. In prostate cancer cells, the compounds induce degradation of both full-length androgen receptor (fAR) and splice variant AR (AR-V7) to inhibit AR transcriptional activity. The consequences of these multiple activities resulted in inhibition of cell growth and migration and induction of apoptosis. Finally and importantly, the compounds demonstrate strong in vitro and in vivo anti-breast and anti-prostate cancer activities, with no apparent host toxicities.

26 Claims, 13 Drawing Sheets

Compound 1

Compound 2

Compound 3

Compound 4

Compound 5

Compound 6

Compound 7

Compound 8

Compound 9

Compound 10

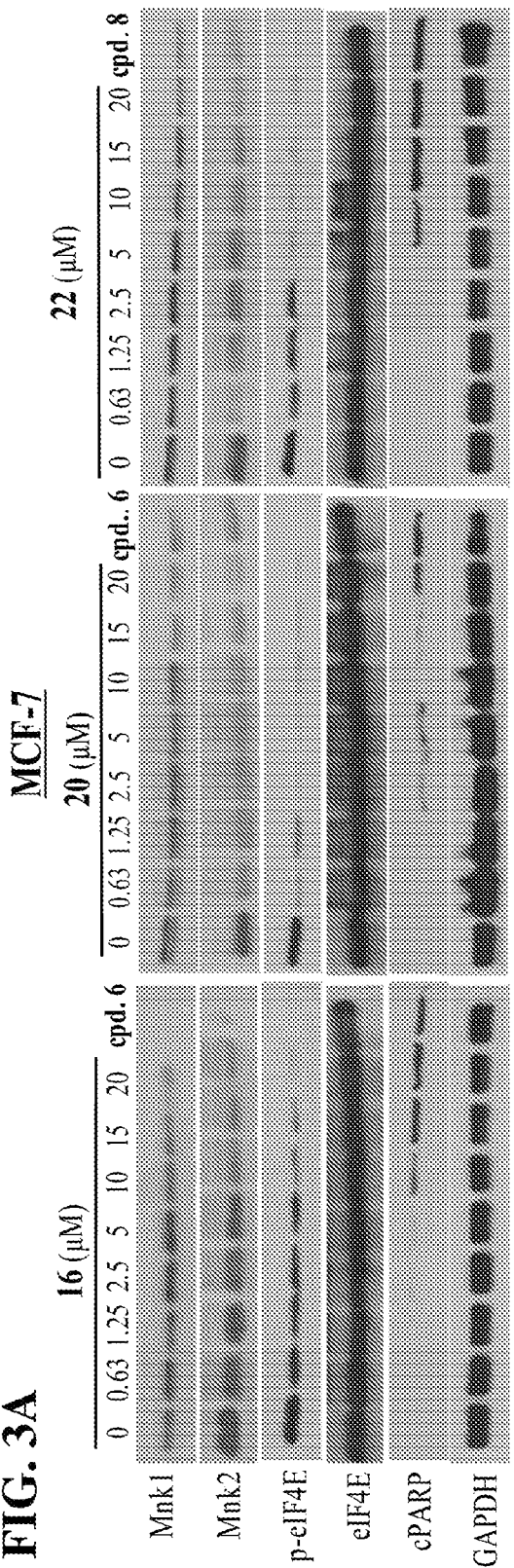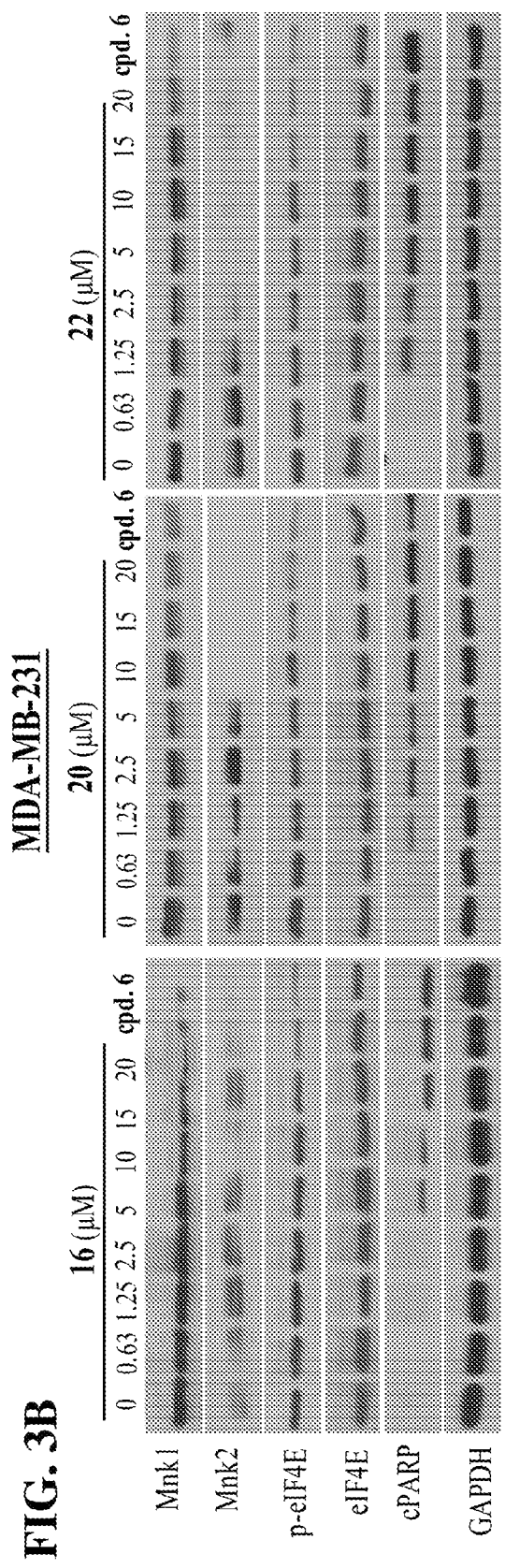
FIG. 3A
FIG. 3B

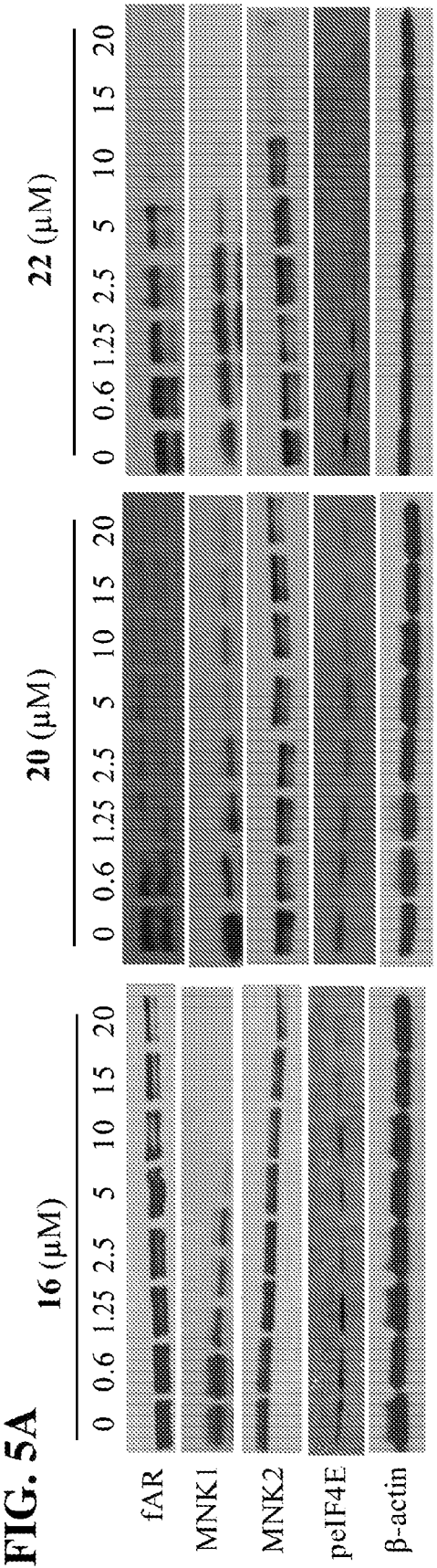
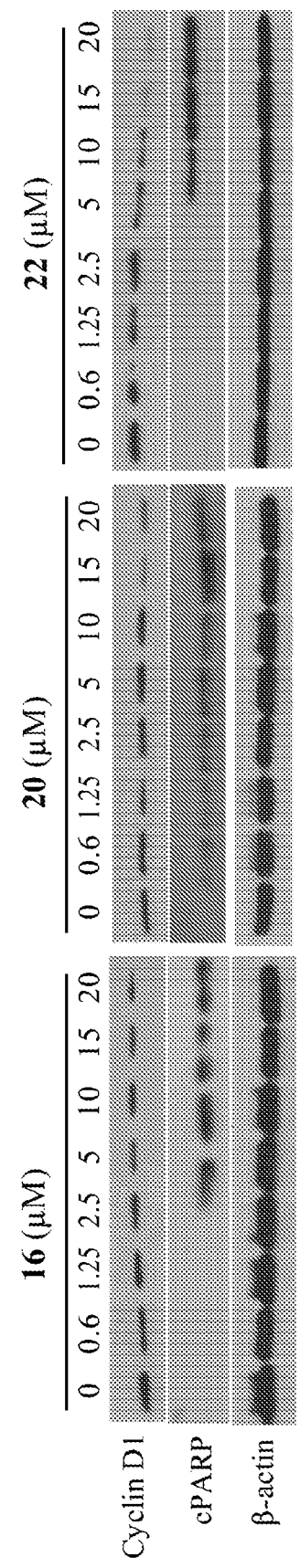
FIG. 5A
FIG. 5B

13-CIS-RAMBA RETINAMIDES THAT DEGRADE MNKS FOR TREATING CANCER

CROSS-REFERENCE

This application claims benefit of U.S. Provisional Application No. 62/082,413, filed on Nov. 20, 2014, the entirety of which is incorporated by reference.

STATEMENT OF FEDERALLY SPONSORED RESEARCH AND DEVELOPMENT

This invention was made with government support under Grant Number CA129379 awarded by the National Institutes of Health. The government has certain rights in the invention.

FIELD OF THE INVENTION

The present invention generally relates at least to the fields of medicine, molecular biology, cancer therapeutics, and dermatology therapeutics. In particular, the invention relates to the synthesis of novel agents which can be used for treating different cancer types, in particular breast and prostate cancers and for treating various dermatological conditions. These agents have utility in therapeutic applications in disease states that are driven by Mnk-eIF4E and/or signaling.

BACKGROUND OF THE INVENTION

Disruption and/or perturbation of cap-dependent translation is essential for the development of cancers and many fibrotic diseases, the most notable being Alzheimer's disease.[1] Hyper-activation of eukaryotic translation initiation factor 4E (eIF4E), the mRNA 5' cap-binding protein of cap-dependent translation promotes exquisite transcript-specific translation of key mRNAs that are indispensable in cancer initiation, progression and metastases.[2] The oncogenic potential of eIF4E is dependent on serine 209 phosphorylation by MAPK-interacting kinases 1 and 2 (Mnk1/2).

Currently, there are several strategies directed at disruption of the eIF4F complex to inhibit hyper-activity of oncogenic protein translation as a means to effectively treat a variety of cancers.[3]

When targeting a critical process such as translation, a major critical question is whether the drug will have significant effects on normal cellular processes, leading to limiting toxicities and too narrow a therapeutic window. This question has been addressed by several experimental and a few clinical studies. Recently, Graff et al. demonstrated that down-regulation of eIF4E by antisense oligonucleotide therapy caused reduction of in vivo tumor growth in MDA-MB-231 breast and PC-3 prostate cancer models without toxicity despite an ~80% eIF4E knockdown in essential organs.[4] These data provided in vivo evidence that cancers may be more susceptible to eIF4E inhibition than normal tissue and provided the basis for advancement of eIF4E-specific antisense molecule LY2275796 into Phase 1 clinical studies.[5] In other more recent studies, cercosporamide, a potent Mnk1/2 kinase inhibitor exhibited antitumor efficacies against HCT116 colon carcinoma xenograft tumors[6] MV4-11 acute myeloid leukemia (AML) tumors in animal models,[7] without any toxicity.

We previously reported that its proprietary novel C-4 azolyl retinamides (NRs) based on all-trans retinoic acid (ATRA) (Compound 1) (FIG. 1) scaffold induced apoptosis, potently inhibited the growth, migration and invasion of a variety of human breast and prostate cancer cell lines. With respect to the breast cancer (BC) cell lines, we demonstrated that the anti-BC activity of our NRs was due mainly to degradation of Mnk1/2 with subsequent suppression of phosphorylated eIF4E (peIF4E).[8a] However, in the prostate cancer (PC) cell lines, the Applicant demonstrated that the anti-tumor activity of the NRs was due to simultaneous inhibition of the Mnk/eIF4E and androgen receptor (AR) signaling pathways.[8b]

It is important to state here that unlike other reported small molecules which inhibit Mnk1/2 kinase activities,[3e,6,9] our NRs induced Mnk1/2 degradation via the ubiquitin-proteasome pathway with resultant depletion of peIF4E.[8] Structures of promising Mnk 1 and/or 2 kinase inhibitors include CGP57380 (Compound 2),[10] cercosporamide (Compound 3),[6] MNKI-19 (Compound 4)[11] and MNKI85 (Compound 5).[11] Compounds 2-5 are presented in FIG. 1. In addition, the structures of our Mnk degrading agent (MNKDA), VNLG-152 (Compound 6)[8a] and related compounds,[12] VN/14-1 (7), VN/66-1 (Compound 8) and N-(4-hydroxyphenyl) retinamide (4-HPR or fenretinide) (Compound 9) are also depicted in FIG. 1.

Given the implication of Mnk1/2-eIFE axis in the initiation and progressions of all types of solid tumors[24] and hematologic cancers,[25] there is a need for the development of additional and more efficacious agents for the prevention and treatment of all forms of breast and prostate cancers and other diseases which depend on functional Mnk 1/2.

BRIEF SUMMARY OF THE INVENTION

The present invention relates to novel 13-cis-retinoic acid metabolism blocking agent (RAMBA) retinamides that cause oxidative down-regulation of mitogen activated protein kinase interacting proteins (MNK1/2), block phosphorylation of eIF4E, induce apoptosis, inhibit cell growth and migration and invasion of triple negative and Her-2 over-expressing human breast cancer cells and tumor xenografts. These novel compounds are agents for the prevention and treatment of all forms of breast and prostate cancers and other diseases which depend on functional Mnk1/2.

The present invention relates to novel 13-cis-RAMBA retinamides, in particular the present invention relates to the novel Compounds 16, 20 and 22 herein described and their methods of synthesis.

In one embodiment, the present invention relates to novel Compounds 16, 20, and 22 which can be used for treating breast and prostate cancer in human subjects.

In another embodiment, the present invention relates to Compounds 16, 20, and 22 which can be used as therapeutic agents for treating breast or prostate cancer in a human subject in need thereof and wherein the agents can be used in combination with other anti-cancer agents which are currently used for treating breast and prostate cancer.

In another embodiment, the present invention relates to novel Compounds 16, 20, and 22 which can be used for treating all cancer types that are driven by MnK-EiF4E and/or signaling.

In another embodiment, the present invention relates to novel Compounds 16-25 herein described which can be used to treat human breast cancer in a human subject in need thereof.

In another embodiment, the present invention relates to novel Compounds 16-22 herein described which can be used to treat human prostate cancer in a human subject in need thereof.

In another embodiment, the present invention relates to novel Compounds 20 and 22 herein described which can be used to suppress breast xenograft tumor growth in a human subject in need thereof.

In another embodiment, the present invention relates to Compound 20 herein described which can be used to inhibit the growth of castration-resistant CWR22Rv1 human prostate tumor xenografts.

In another embodiment, the present invention relates to the novel compounds herein described which can be used in the manufacture of a medicament for treating or preventing Mnk1/2 and androgen receptor (AR) associated conditions including but not limited to breast cancer, prostate cancer, bladder cancer, pancreatic cancer, hepatocellular carcinoma, benign prostatic hyperplasia (BPH), Kennedy's disease and hematologic cancers.

In another embodiment, the present invention relates to novel Compounds 16, 20, and 22 herein described which can be used in the manufacture of a medicament for treating or preventing Mnk1/2 and androgen receptor (AR) associated conditions including but not limited to breast cancer, prostate cancer, bladder cancer, pancreatic cancer, hepatocellular carcinoma, benign prostatic hyperplasia (BPH), Kennedy's disease and hematologic cancers.

In another embodiment, the present invention relates to novel Compounds 16-40 and their methods of synthesis herein described.

In another embodiment, the present invention relates to novel Compounds 16-40 which can be used for treating various dermatological (skin) conditions, including but not limited to acne, psoriasis, wrinkling, and photoaged skin, in a human subject in need thereof.

In another embodiment, the present invention relates to novel Compounds 16, 20, and 22 herein described which can be used as therapeutic agents for treating dermatological (skin) condition, including but not limited to acne, psoriasis, wrinkling, and photoaged skin, in a human subject in need thereof.

In another embodiment, the present invention relates to novel Compounds 16, 20, and 22 in combination with other therapeutic agents used to treat dermatological (skin) conditions, including but not limited to acne, psoriasis, wrinkling, and photoaged skin, in a human subject in need thereof.

In another embodiment, the present invention relates to novel compounds herein described which can be used in the manufacture of a medicament for treating or preventing Mnk1/2 and androgen receptor (AR) associated conditions including but not limited to breast cancer, prostate cancer, bladder cancer, pancreatic cancer, hepatocellular carcinoma, benign prostatic hyperplasia (BPH), Kennedy's disease and hematologic cancers.

In another embodiment, the present invention relates to novel compounds herein described which can be used as therapeutic agents for treating breast or prostate cancer in a human subject in need thereof and wherein the agents can be used in combination with other anti-cancer agents which are currently used for treating breast and prostate cancer.

In another embodiment, the present invention relates to novel compounds herein described which can be used as therapeutic agents for treating dermatological (skin) conditions, including but not limited to acne, psoriasis, wrinkling, and photoaged skin, in a patient in need thereof.

BRIEF DESCRIPTION OF THE DRAWING

FIG. 1 also illustrates examples of MAPK-interacting kinase Mnk 1 and/or 2 kinase inhibitors, including CGP57380 (Compound 2), cercosporamide (Compound 3), MNKI-19 (Compound 4), MNKI85 (Compound 5). FIG. 1 also shows exemplary species of novel C-4 azolyl retinamides previously developed by the Applicant, including a Mnk degrading agent VNLG-152 (Compound 6) and related compounds, VN/14-1 (Compound 7), VN/66-1 (Compound 8) and N-(4-hydroxyphenyl) retinamide (4-HPR or fenretinide) (Compound 9). FIG. 1 further illustrates a structure of a 13-cis retinoic acid (13-CRA) (Compound 10) scaffold that provides a basis for developing a novel retinamide, including C-4 heteroaryl 13-cis retinamide, according to the present invention.

FIGS. 5(A)-(B) illustrate effects the novel retinamides of the present invention on the expression of fAR, Mnk, peIF4E, cyclin D1 and cleaved PARP in LNCaP cells.

FIG. 8 illustrates effects of the novel retinamides of the present invention on the viability of LNCaP cells transiently knocked-down for androgen receptors (AR) and/or Mnk1.

FIG. 9 illustrates suppressive effects of the novel retinamides of the present invention on breast xenograft tumor growth in vivo. FIG. 9C illustrates the changes in the body weight of the mice during the course of treatments. Animals were monitored for changes in body weight as a surrogate marker for toxicity in control and treatment groups. FIG. 9D illustrates the effects of the novel retinamides of the present invention on the expression of proteins modulated by Mnk/eIF4E signaling.

FIG. 10 illustrates the suppressive effects of the novel retinamides of the present invention on prostate xenograft tumor growth in vivo.

DETAILED DESCRIPTION OF THE INVENTION

Figure 1:
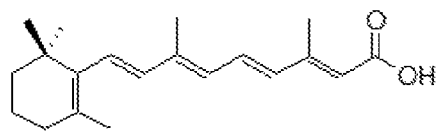
FIG. 1 illustrates a structure of an all-trans retinoic acid (ATRA) (Compound 1) scaffold that provides a basis for novel C-4 azolyl retinamides previously developed by the Applicant.
Figure 1:
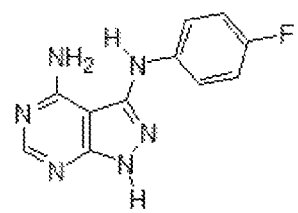
Figure 1:
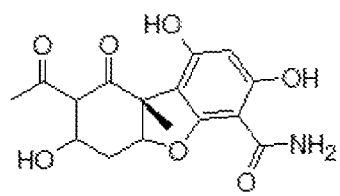
Figure 1:
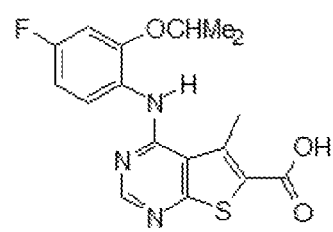
Figure 1:
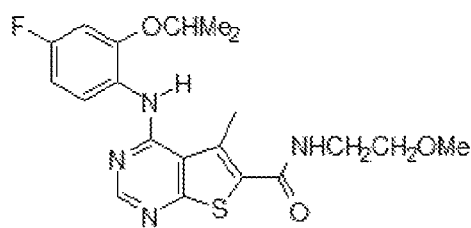
Figure 1:
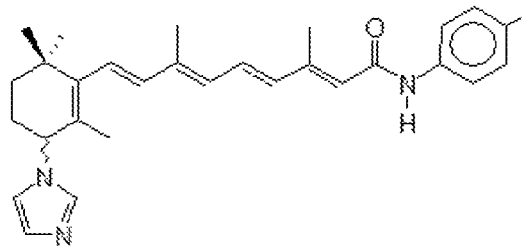
Figure 1:
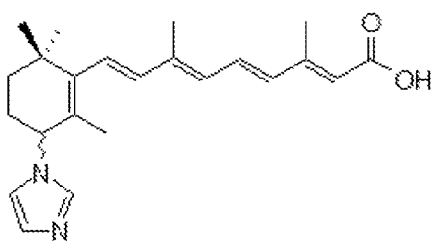
Figure 1:
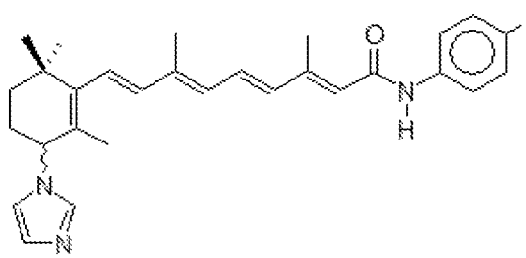
Figure 1:
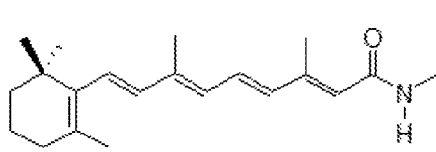
Figure 1:
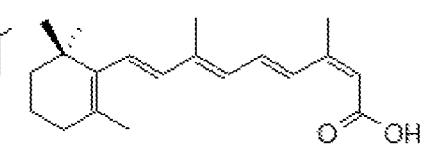

In the present invention, novel compounds based on 13-cis retinoic acid (13-CRA) (Compound 10) (FIG. 1) scaffold are designed and synthesized, and their anti-cancer activities are evaluated in both in vitro and in vivo models of human breast and prostate cancers.

These novel compounds target Mnk1/2 degradation in both breast cancer (BC) and prostate cancer (PC) cells and also induce AR degradation in PC cells, which in turn led to induction of apoptosis, cell cycle arrest, inhibition of cell growth, colonization, migration, and invasion. Importantly, Compounds 20 and 22 significantly inhibited tumor growth of aggressive MDA-MB-213 breast cancer xenografts, while Compound 20 was shown to substantially suppress castration-resistant prostate cancer CWR2Rv1 xenografts in vivo.

Figure 2:
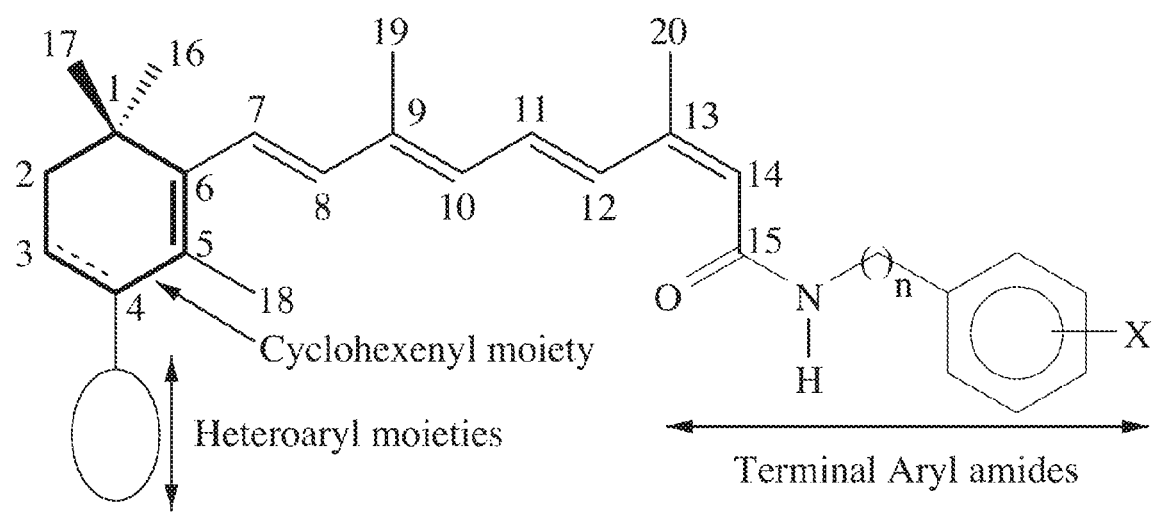
FIG. 2 is a schematic representation of the overall design strategy of the novel retinamides of the present invention.

Design Strategy:

Rationale structural modifications of small molecules allow for their interactions with molecular target(s) in ways that could lead to improved drug-like compounds, and possibly enhanced in vivo pharmacokinetic profiles.[13] Because of the inventors' desire to discover more efficacious anti-cancer agents, the inventors were eager to exploit Compound 10's scaffold as a strategy to design novel potent/efficacious MNKDAs with improved drug-like properties. The rationale of using this scaffold is based on experimental and clinical reports that, unlike ATRA (Compound 1), 13-CRA (Compound 10) has long elimination half-life in humans[14] and most animal species.[15] In addition, the inventors explored rational modification of the terminal amide moiety, C-4 heterocycles and the cyclohexene ring (FIG. 2). It is relevant to state here that our previous studies with the ATRA scaffold MNKDAs identified the C-4 azolyl retinamides to be superior to the corresponding carboxylic acid and esters.[8]

C-4 Azoyl/Terminal Amide Modifications:

Based on the continued successes of the C-imidazole retinamides with the ATRA scaffolds as promising anti-cancer agents,[8] the inventors designed and synthesized Compounds 16-25 as outlined in Scheme 1.

Cyclohexene Rigidification/C-4 Aryl and Heteroaryl Modifications:

On the basis of previous studies which showed that structural rigidification that introduces conformational constrains around rotatable bonds contributed to higher specificity and potency, greater metabolic stability, and improved bioavailability,[16] the inventors designed and synthesized several cyclohexadiene C-4 aryl substituted retinamides, Compounds 33-40 (Scheme 2). A potential advantage of this strategy is that the achiral nature of these compounds would not require the tedious characterization of the racemates and pure enantiomers as would be required in advanced preclinical development for the chiral compounds of Scheme 1.[17]

Chemistry:

Herein, the present inventors report for the first time, the synthesis of 18 novel compounds based on the structural scaffold of 13-CRA (Compound 10), as outlined in Schemes 1 and 2.

Scheme 1: Synthesis of C-4 Azoyl/terminal Amide Compounds 17-22[a]

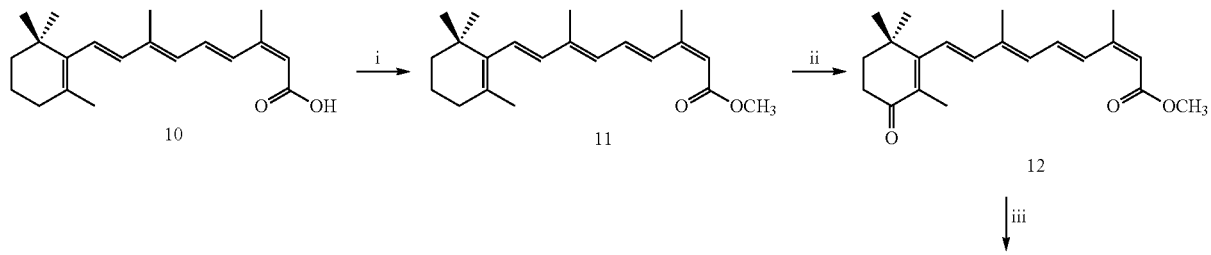

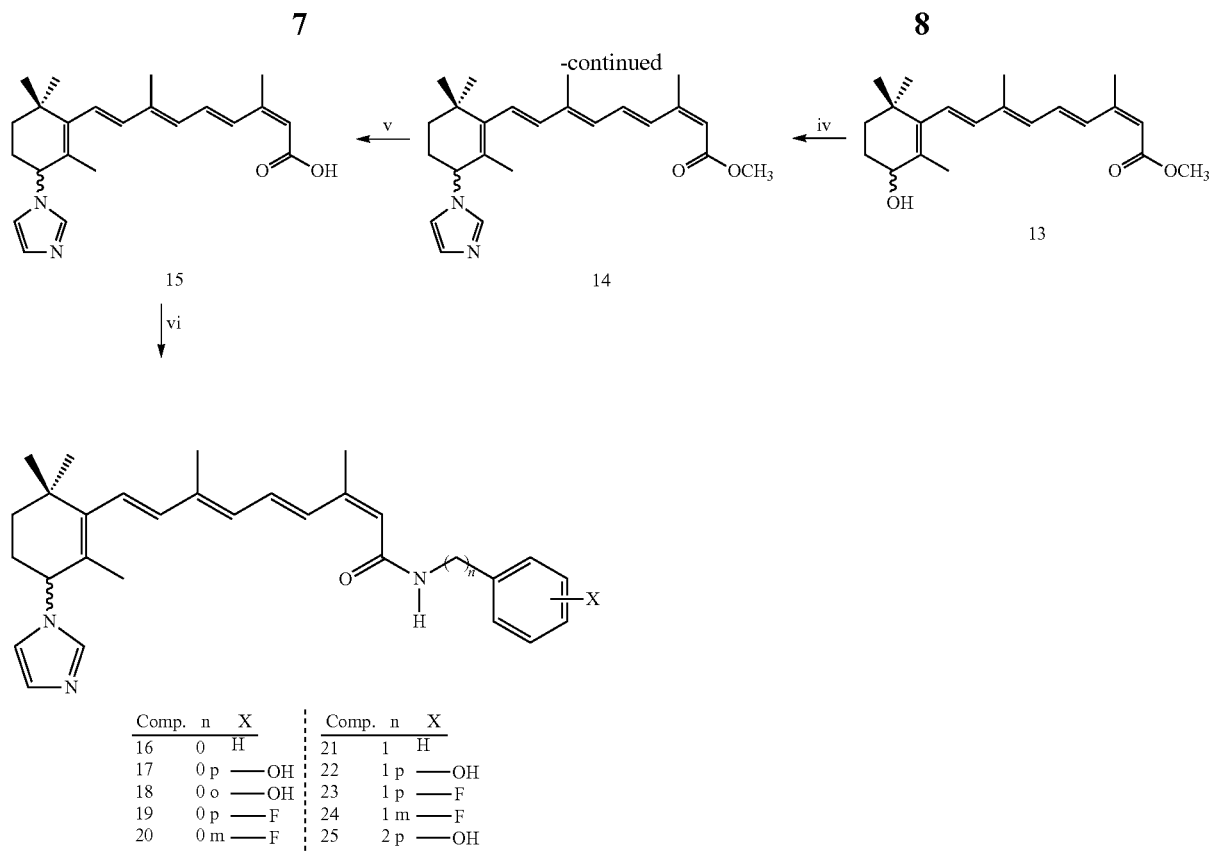

| Comp. | n | X | | Comp. | n | X | |
|---|---|---|---|---|---|---|---|
| 16 | 0 | H | | 21 | 1 | H | |
| 17 | 0 | p | —OH | 22 | 1 | p | —OH |
| 18 | 0 | o | —OH | 23 | 1 | p | —F |
| 19 | 0 | p | —F | 24 | 1 | m | —F |
| 20 | 0 | m | —F | 25 | 2 | p | —OH |

[a] Reagents and conditions: (i) (CH₃)₃SiCHN₂, MeOH/benzene; (ii) MnO₂, CH₂Cl₂; (iii) NaBH₄, MeOH; (iv) CDI, CH₃CN; (v) 2M KOH, MeOH, reflux; (vi) EDC, HOBT, DIEA, appropriate anilines, DMF.

The synthesis of (2Z,4E,6E,8E)-9-(3-(1H-imidazol-1-yl)-2,6,6-trimethylcyclohex-1-en-1-yl)-3,7-dimethylnona-2,4,6,8-tetraenoic acid (Compound 15) was carried out in five steps from the commercially available 13-CRA (Compound 10) and the procedure was adopted from our reported procedures of ATRA based retinamides.[18]

Protection of the carboxylic acid as the methyl ester (Compound 11) was done using trimethylsilyldiazomethane in hexanes followed by allylic oxidation using MnO₂ to give 4-oxo intermediate (Compound 12). Reduction of Compound 12 using NaBH₄ gave the (±)-4-hydroxymethylterionate (Compound 13) which was further treated with carbonyldiimidazole (CDI) at ambient temperature to yield (±)-(1H-imidazol-1-yl)methylterionate (Compound 14). Alkaline hydrolysis of Compound 14 in refluxing methanol gave the desired free acid Compound 15. Coupling of the respective amines with Compound 15 was successfully achieved using ethyl(dimethylaminopropyl) carbodiimide (EDC), hydroxybenzotriazole (HOBt), diisopropylethylamine (DIEA) to give Compounds 16-25 (Scheme 1), respectively Scheme 2: Synthesis of Cyclohexen Rigidification/C-4 Aryl and Heteroaryl Retinamides[a]

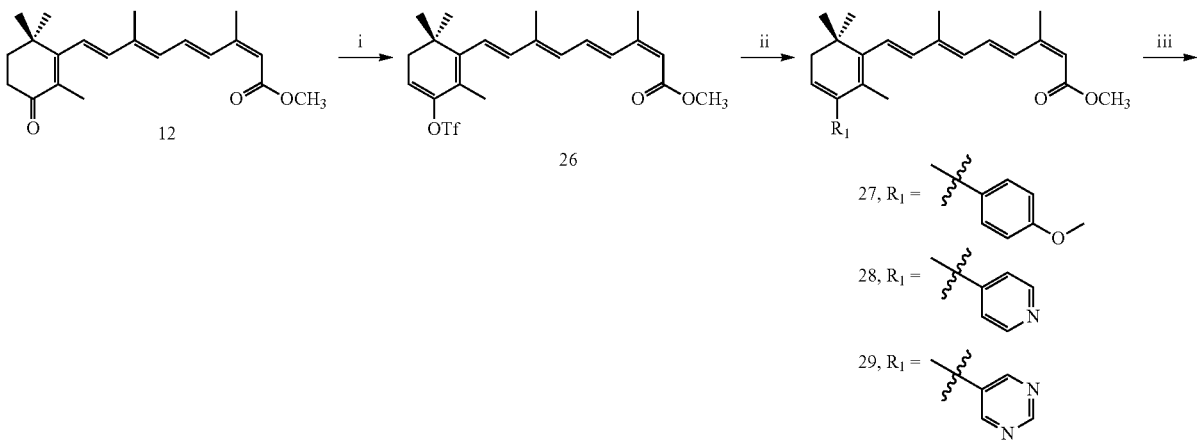

-continued

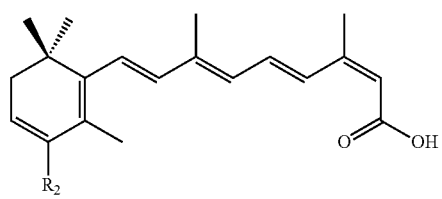

30, R₂ =

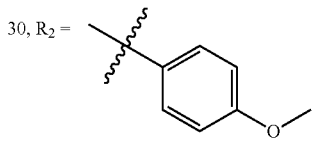

31, R₂ =

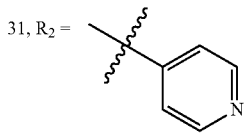

32, R₂ =

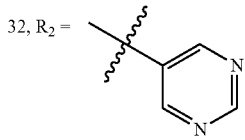

↓ iv

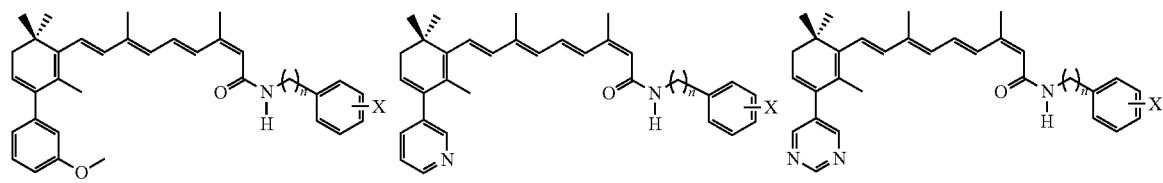

33, n = 1, X = p-OH
34, n = 2, X = p-OH 35, n = 0, X = H
36, n = 1, X = p-OH
37, n = 2, x = p-OH 38, n = 0, X = H
39, n = 1, X = p-OH
40, n = 2, x = p-OH

<sup>a</sup>Reagents and coditions: (i) 5-Chloro-2-pyridyl triflimide, NaN(SiMe₃)₂, THF; (ii) 3-methoxybenzylboronic acid, Pd(PPh₃)₄, CeCO₃, dioxane, reflux; (iii) 2M KOH, MeOH, reflux (iv) EDC, HOBT, DIEA, appropriate benzylamine, DMF.

The synthesis of achiral C-4 aryl retinamides Compounds 33-40 (Scheme 2) commenced from the 4-oxo intermediate (Compound 12). Generation of enolate using sodium bis(trimethylsilyl)amide in THF solution and trapping of the enolate with N-(5-chloro-2-pyridyl)bistrifluoromethanesulfonimide furnished the vinyl triflate Compound 26 according to the reported procedure.[19] However, it should be noted that this reaction was carried out at −78° C. throughout the reaction time, because, at higher temperatures, decomposition occurred and ≤20% of the products were obtained. Regiospecific palladium-catalyzed cross-coupling reaction with boronic acids[20] provided Compounds 27-29. Ester hydrolysis using 2M KOH gave the corresponding free acids Compounds 30-32. Coupling of these respective acids with appropriate amines was successfully achieved using EDC, HOBt and DIEA to give Compounds 33-40, respectively (Scheme 2).

Further, the inventors have also developed novel derivative compounds based on 13-cis retinoic acid (13-CRA) scaffold.

Amide Derivatives (Series 1):

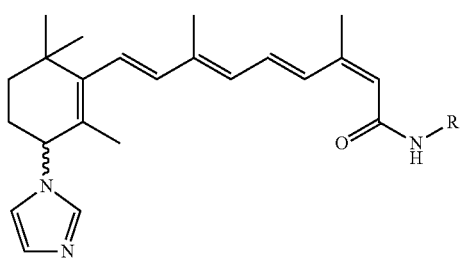

The R group can be, for example, a benzyl group or a heterocyclic group that is mono-, di-, or tri-substituted at either at the para, meta, or ortho position with OH, OMe, CN, CO₂H, CO₂Me, SO₂NH₂; imidazole, 1H-tetrazole, pyridine and their derivatives. Non-limiting examples of amide derivatives are presented in TABLE 1.

TABLE 1

Amide derivatives (Series A)

| Compound number<br>Compound name | Structure |
|---|---|
| VNHM-1-66 (A1)<br>(2Z,4E,6E,8E)-9-(3-(1H-imidazol-1-yl)-2,6,6-trimethylcyclohex-1-en-1-yl)-3,7-dimethyl-N-phenylnona-2,4,6,8-tetraenamide | 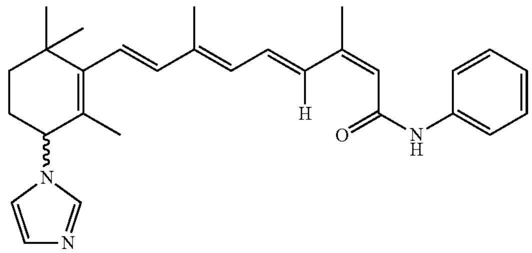 |
| VNHM-1-69 (A2)<br>(2Z,4E,6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide | 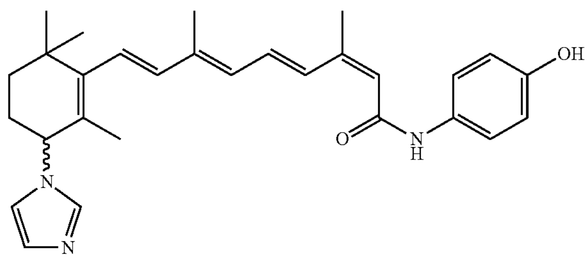 |
| VNHM-1-74 (A3)<br>(2Z,4E,6E,8E)-9-(3-(1H-imidazol-1-yl)-2,6,6-trimethylcyclohex-1-en-1-yl)-N-(2-hydroxyphenyl)-3,7-dimethylnona-2,4,6,8-tetraenamide | 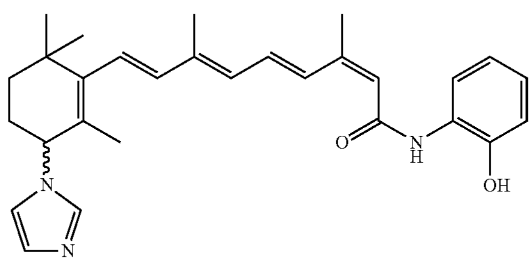 [SMILES: CC1=C(/C=C/C(C)=C/C=C/C(C)=C\C(=O)Nc2ccccc2O)C(C)(C)CCC1n1ccnc1] |
| VNHM-1-75 (A4)<br>(2Z,4E,6E,8E)-9-(3-(1H-imidazol-1-yl)-2,6,6-trimethylcyclohex-1-en-1-yl)-N-(4-fluorophenyl)-3,7-dimethylnona-2,4,6,8-tetraenamide | 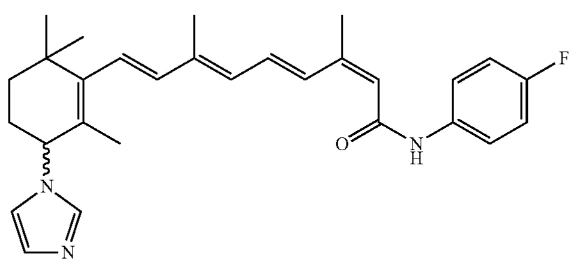 [SMILES: CC1=C(/C=C/C(C)=C/C=C/C(C)=C\C(=O)Nc2ccc(F)cc2)C(C)(C)CCC1n1ccnc1] |
| VNHM-1-81 (A5)<br>(2Z,4E,6E,8E)-9-(3-(1H-imidazol-1-yl)-2,6,6-trimethylcyclohex-1-en-1-yl)-N-(3-fluorophenyl)-3,7-dimethylnona-2,4,6,8-tetraenamide | 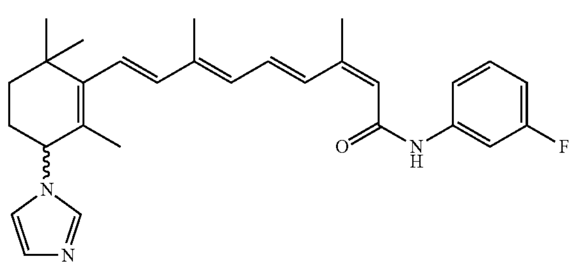 [SMILES: CC1=C(/C=C/C(C)=C/C=C/C(C)=C\C(=O)Nc2cccc(F)c2)C(C)(C)CCC1n1ccnc1] |

TABLE 1-continued

Amide derivatives (Series A)

| Compound number Compound name | Structure |
|---|---|
| A6 (2Z,4E,6E,8E)-9-(3-(1H-imidazol-1-yl)-2,6,6-trimethylcyclohex-1-en-1-yl)-N-(4-cyanophenyl)-3,7-dimethylnona-2,4,6,8-tetraenamide | |
| A7 methyl 4-((2Z,4E,6E,8E)-9-(3-(1H-imidazol-1-yl)-2,6,6-trimethylcyclohex-1-en-1-yl)-3,7-dimethylnona-2,4,6,8-tetraenamido)benzoate | |
| A8 4-((2Z,4E,6E,8E)-9-(3-(1H-imidazol-1-yl)-2,6,6-trimethylcyclohex-1-en-1-yl)-3,7-dimethylnona-2,4,6,8-tetraenamido)benzoic acid | |
| A9 (2Z,4E,6E,8E)-9-(3-(1H-imidazol-1-yl)-2,6,6-trimethylcyclohex-1-en-1-yl)-3,7-dimethyl-N-(4-sulfamoylphenyl)nona-2,4,6,8-tetraenamide | |
| A10 (2Z,4E,6E,8E)-9-(3-(1H-imidazol-1-yl)-2,6,6-trimethylcyclohex-1-en-1-yl)-1-(1H-imidazol-1-yl)-3,7-dimethylnona-2,4,6,8-tetraen-1-one | |

TABLE 1-continued

Amide derivatives (Series A)

Compound number
Compound name    Structure

A11
(2Z,4E,6E,8E)-9-(3-
(1H-imidazol-1-yl)-
2,6,6-
trimethylcyclohex-1-
en-1-yl)-N-(tert-butyl)-
3,7-dimethylnona-
2,4,6,8-tetraenamide A12
(2Z,4E,6E,8E)-9-(3-
(1H-imidazol-1-yl)-
2,6,6-
trimethylcyclohex-1-
en-1-yl)-N-(4-
methoxyphenyl)-3,7-
dimethylnona-2,4,6,8-
tetraenamide A13
(2Z,4E,6E,8E)-9-(3-
(1H-imidazol-1-yl)-
2,6,6-
trimethylcyclohex-1-
en-1-yl)-3,7-dimethyl-
1-(4H-1,2,4-triazol-4-
yl)nona-2,4,6,8-
tetraen-1-one A14
(2Z,4E,6E,8E)-9-(3-
(1H-imidazol-1-yl)-
2,6,6-
trimethylcyclohex-1-
en-1-yl)-3,7-dimethyl-
N-(pyridin-2-yl)nona-
2,4,6,8-tetraenamide A15
(2Z,4E,6E,8E)-9-(3-
(1H-imidazol-1-yl)-
2,6,6-
trimethylcyclohex-1-
en-1-yl)-3,7-dimethyl-
N-(4-
(trifluoromethyl)phenyl)
nona-2,4,6,8-
tetraenamide Series B derivatives:

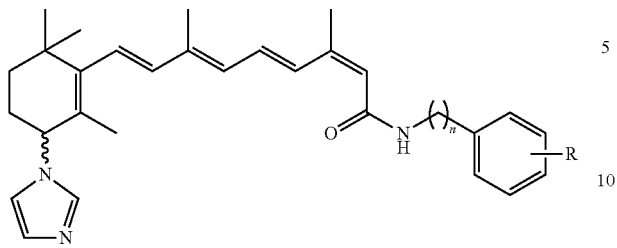

In these derivatives, n can be, for example, any integer between 1 to 6. The R group can be, for example, a benzyl group or a heterocyclic group that is mono-, di-, or tri-substituted at either at the para, meta, or ortho position with OH, OMe, CN, $CO_2H$, $CO_2Me$, $SO_2NRH$; imidazole; or 1H-tetrazole. Non-limiting examples of Series B derivatives are presented in TABLE 2.

TABLE 2

Series B derivatives

| Compound number Compound name | Structure |
|---|---|
| VNHM-1-73 (B1) (2Z,4E,6E,8E)-9-(3-(1H-imidazol-1-yl)-2,6,6-trimethylcyclohex-1-en-1-yl)-N-(4-hydroxybenzyl)-3,7-dimethylnona-2,4,6,8-tetraenamide | |
| VNHM-1-84 (B2) (2Z,4E,6E,8E)-9-(3-(1H-imidazol-1-yl)-2,6,6-trimethylcyclohex-1-en-1-yl)-N-benzyl-3,7-dimethylnona-2,4,6,8-tetraenamide | |
| B3 4-(((2Z,4E,6E,8E)-9-(3-(1H-imidazol-1-yl)-2,6,6-trimethylcyclohex-1-en-1-yl)-3,7-dimethylnona-2,4,6,8-tetraenamido)methyl)benzoic acid | |

TABLE 2-continued

Series B derivatives

| Compound number Compound name | Structure |
|---|---|
| B4 (2Z,4E,6E,8E)-9-(3-(1H-imidazol-1-yl)-2,6,6-trimethylcyclohex-1-en-1-yl)-N-(3-cyanobenzyl)-3,7-dimethylnona-2,4,6,8-tetraenamide | |
| VNHM-1-111 (B5) (2Z,4E,6E,8E)-9-(3-(1H-imidazol-1-yl)-2,6,6-trimethylcyclohex-1-en-1-yl)-N-(3-fluorobenzyl)-3,7-dimethylnona-2,4,6,8-tetraenamide | |
| B6 (2Z,4E,6E,8E)-9-(3-(1H-imidazol-1-yl)-2,6,6-trimethylcyclohex-1-en-1-yl)-3,7-dimethyl-N-(4-(trifluoromethyl)benzyl)nona-2,4,6,8-tetraenamide | |
| B7 (2Z,4E,6E,8E)-9-(3-(1H-imidazol-1-yl)-2,6,6-trimethylcyclohex-1-en-1-yl)-3,7-dimethyl-N-(3-sulfamoylbenzyl)nona-2,4,6,8-tetraenamide | |
| B8 (2Z,4E,6E,8E)-9-(3-(1H-imidazol-1-yl)-2,6,6-trimethylcyclohex-1-en-1-yl)-3,7-dimethyl-N-phenethylnona-2,4,6,8-tetraenamide | |

TABLE 2-continued

Series B derivatives

| Compound number Compound name | Structure |
|---|---|
| B9 (2Z,4E,6E,8E)-9-(3-(1H-imidazol-1-yl)-2,6,6-trimethylcyclohex-1-en-1-yl)-N-(3-hydroxyphenethyl)-3,7-dimethylnona-2,4,6,8-tetraenamide | |
| B10 (2Z,4E,6E,8E)-9-(3-(1H-imidazol-1-yl)-2,6,6-trimethylcyclohex-1-en-1-yl)-3,7-dimethyl-N-(3-phenylpropyl)nona-2,4,6,8-tetraenamide | |
| B11 (2Z,4E,6E,8E)-9-(3-(1H-imidazol-1-yl)-2,6,6-trimethylcyclohex-1-en-1-yl)-N-(3-(4-hydroxyphenyl)propyl)-3,7-dimethylnona-2,4,6,8-tetraenamide | |
| B12 (2Z,4E,6E,8E)-9-(3-(1H-imidazol-1-yl)-2,6,6-trimethylcyclohex-1-en-1-yl)-N-(3-(3-fluorophenyl)propyl)-3,7-dimethylnona-2,4,6,8-tetraenamide | |
| B13 (2Z,4E,6E,8E)-9-(3-(1H-imidazol-1-yl)-2,6,6-trimethylcyclohex-1-en-1-yl)-3,7-dimethyl-N-(3-(3-(trifluoromethyl)phenyl)propyl)nona-2,4,6,8-tetraenamide | |

C₄ (R) Derivatives:

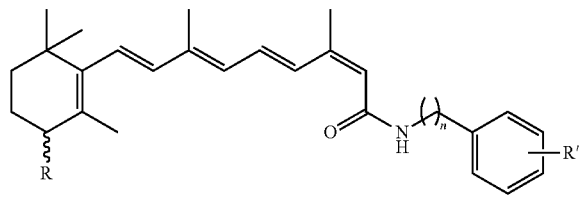

In these derivatives, n can be, for example, 0 to 5. R can be, for example, an 1H-imidazole group, an azo group, an oxime, a benzoimidazole, an azole group, a sulfur containing group, an oxygen containing group, a nitrogen containing group, a pyridyl containing group, an ethylene group, a cyclopropyl-amine group, an ester, a cyano group, an oxirane, or an aziridine group linked with an amide group, an ester group, or an ether group. R' can be, for example, an alkyl, an ester, an ether, a benzyl, a thio, a Weinreb amide, a heterocyclic, a halide, or a hydroxyl. Non-limiting examples of C₄ (R) derivatives are presented in TABLE 3.

TABLE 3

C₄ (R) derivatives

| Compound number Compound name | Structure |
|---|---|
| VNHM-1-4 (C1) (2Z,4E,6E,8E)-methyl 9-(3-(1H-imidazol-1-yl)-2,6,6-trimethylcyclohex-1-en-1-yl)-3,7-dimethylnona-2,4,6,8-tetraenoate | |
| VNHM-1-71 (C2) (2Z,4E,6E,8E)-methyl 9-((E)-3-(hydroxyimino)-2,6,6-trimethylcyclohex-1-en-1-yl)-3,7-dimethylnona-2,4,6,8-tetraenoate | |
| C3 (2Z,4E,6E,8E)-methyl 9-(3-(1H-benzo[d]imidazol-1-yl)-2,6,6-trimethylcyclohex-1-en-1-yl)-3,7-dimethylnona-2,4,6,8-tetraenoate | |
| C4 tert-butyl 4-(3-((1E,3E,5E,7Z)-3,7-dimethyl-9-oxo-9-(phenylamino)nona-1,3,5,7-tetraen-1-yl)-2,4,4-trimethylcyclohex-2-en-1-yl)-1H-imidazole-1-carboxylate | |

TABLE 3-continued

C$_4$ (R) derivatives

| Compound number<br>Compound name | Structure |
|---|---|
| C5<br>(2Z,4E,6E,8E)-9-(3-(1H-imidazol-4-yl)-2,6,6-trimethylcyclohex-1-en-1-yl)-3,7-dimethyl-N-phenylnona-2,4,6,8-tetraenamide | 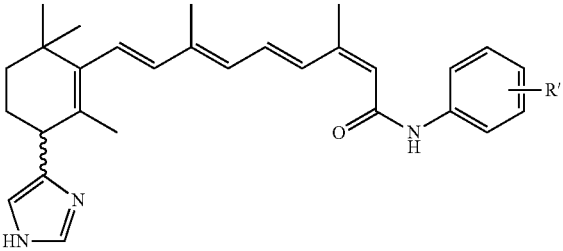 |
| C6<br>(2Z,4E,6E,8E)-3,7-dimethyl-N-phenyl-9-(2,6,6-trimethyl-3-(pyridin-2-yl)cyclohex-1-en-1-yl)nona-2,4,6,8-tetraenamide | 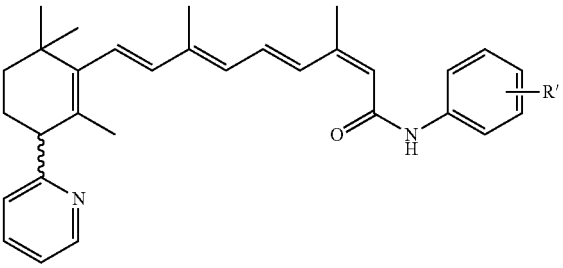 |
| C7<br>(2Z,4E,6E,8E)-9-(3-(3-fluoropyridin-2-yl)-2,6,6-trimethylcyclohex-1-en-1-yl)-3,7-dimethyl-N-phenylnona-2,4,6,8-tetraenamide | 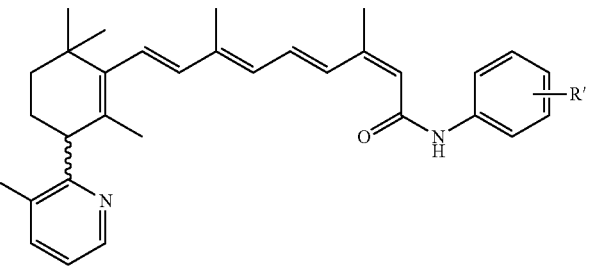 |
| C8<br>(2Z,4E,6E,8E)-3,7-dimethyl-N-phenyl-9-(2,6,6-trimethyl-3-(5-methylpyridin-2-yl)cyclohex-1-en-1-yl)nona-2,4,6,8-tetraenamide | 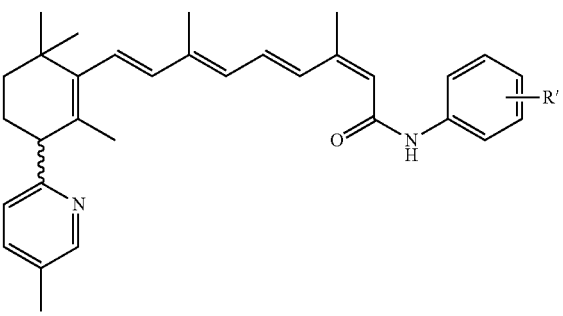 |
| C9<br>(2Z,4E,6E,8E)-9-(3-(5-(tert-butyl)pyridin-2-yl)-2,6,6-trimethylcyclohex-1-en-1-yl)-3,7-dimethyl-N-phenylnona-2,4,6,8-tetraenamide | 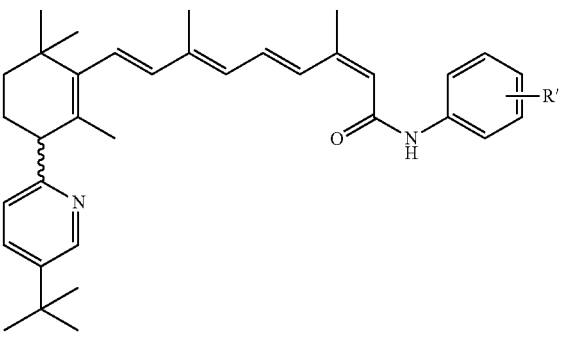 |

TABLE 3-continued

C4 (R) derivatives

| Compound number<br>Compound name | Structure |
|---|---|
| C10<br>(2Z,4E,6E,8E)-3,7-dimethyl-N-phenyl-9-(2,6,6-trimethyl-3-(5-(pyrrolidin-1-yl)pyridin-2-yl)cyclohex-1-en-1-yl)nona-2,4,6,8-tetraenamide | 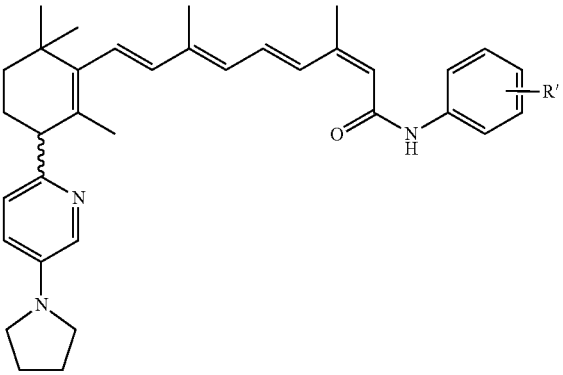 |
| C11<br>(2Z,4E,6E,8E)-3,7-dimethyl-N-phenyl-9-(2,6,6-trimethyl-3-(5-(3-methylpiperidin-1-yl)pyridin-2-yl)cyclohex-1-en-1-yl)nona-2,4,6,8-tetraenamide | 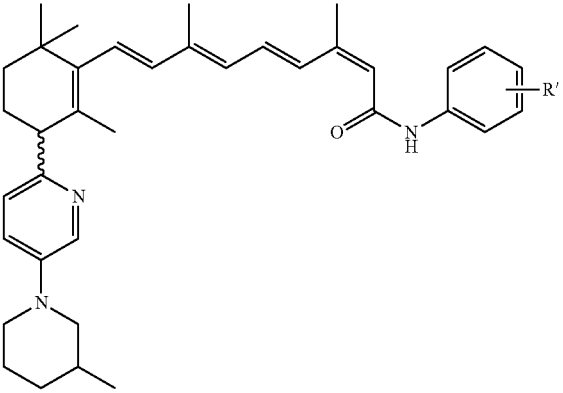 |
| C12<br>(2Z,4E,6E,8E)-9-(3-(5-cyclopropylpyridin-2-yl)-2,6,6-trimethylcyclohex-1-en-1-yl)-3,7-dimethyl-N-phenylnona-2,4,6,8-tetraenamide | 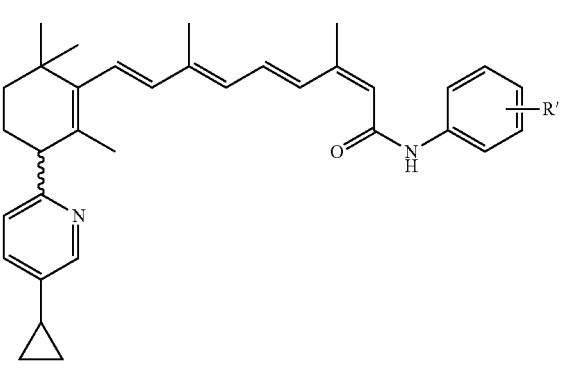 |
| C13<br>ethyl 2-(3-((1E,3E,5E,7Z)-3,7-dimethyl-9-oxo-9-(phenylamino)nona-1,3,5,7-tetraen-1-yl)-2,4,4-trimethylcyclohex-2-en-1-yl)isonicotinate | 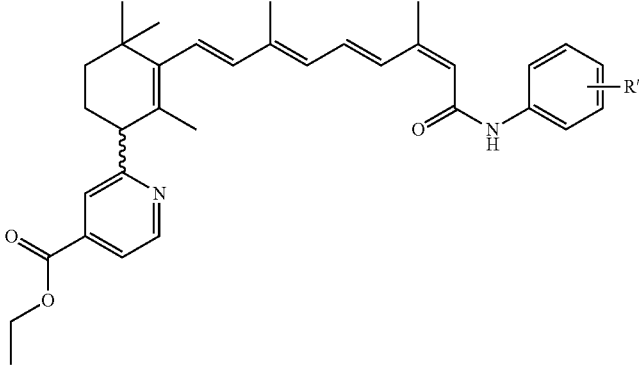 |

TABLE 3-continued

C₄ (R) derivatives

Compound number
Compound name                Structure

C14
2-(3-((1E,3E,5E,7Z)-3,7-
dimethyl-9-oxo-9-
(phenylamino)nona-
1,3,5,7-tetraen-1-yl)-2,4,4-
trimethylcyclohex-2-en-1-
yl)isonicotinic acid C15
(2Z,4E,6E,8E)-9-(3-(4-
(((Z)-
benzylideneamino)methyl)
pyridin-2-yl)-2,6,6-
trimethylcyclohex-1-en-1-
yl)-3,7-dimethyl-N-
phenylnona-2,4,6,8-
tetraenamide C16
methyl 5-(3-
((1E,3E,5E,7Z)-3,7-
dimethyl-9-oxo-9-
(phenylamino)nona-
1,3,5,7-tetraen-1-yl)-2,4,4-
trimethylcyclohex-2-en-1-
yl)pyrazine-2-carboxylate C17
5-(3-((1E,3E,5E,7Z)-3,7-
dimethyl-9-oxo-9-
(phenylamino)nona-
1,3,5,7-tetraen-1-yl)-2,4,4-
trimethylcyclohex-2-en-1-
yl)pyrazine-2-carboxylic
acid TABLE 3-continued C_A (R) derivatives

| Compound number<br>Compound name | Structure |
|---|---|
| C18<br>(2Z,4E,6E,8E)-9-(3-(5-fluoropyrazin-2-yl)-2,6,6-trimethylcyclohex-1-en-1-yl)-3,7-dimethyl-N-phenylnona-2,4,6,8-tetraenamide | 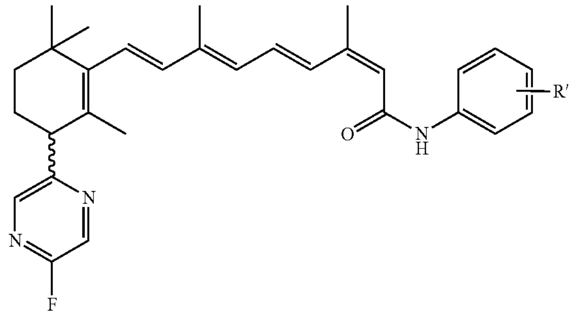 |
| C19<br>(2Z,4E,6E,8E)-3,7-dimethyl-N-phenyl-9-(2,6,6-trimethyl-3-(thiazol-4-yl)cyclohex-1-en-1-yl)nona-2,4,6,8-tetraenamide | 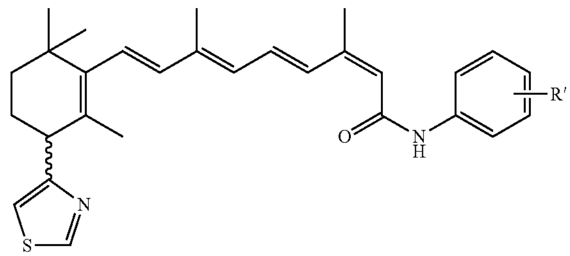 |
| C20<br>(2Z,4E,6E,8E)-9-(3-(2-cyanothiazol-4-yl)-2,6,6-trimethylcyclohex-1-en-1-yl)-3,7-dimethyl-N-phenylnona-2,4,6,8-tetraenamide | 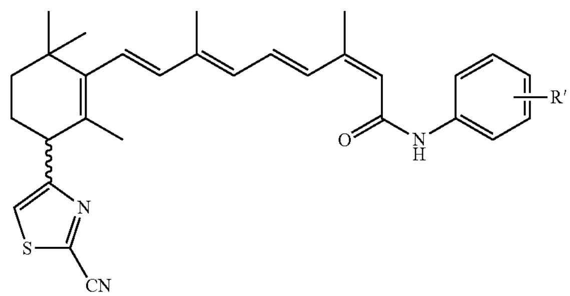 |
| C21<br>methyl 4-(3-((1E,3E,5E,7Z)-3,7-dimethyl-9-oxo-9-(phenylamino)nona-1,3,5,7-tetraen-1-yl)-2,4,4-trimethylcyclohex-2-en-1-yl)thiazole-2-carboxylate | 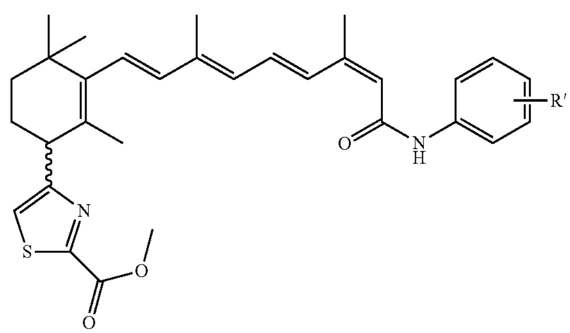 |
| C22<br>4-(3-((1E,3E,5E,7Z)-3,7-dimethyl-9-oxo-9-(phenylamino)nona-1,3,5,7-tetraen-1-yl)-2,4,4-trimethylcyclohex-2-en-1-yl)thiazole-2-carboxylic acid | 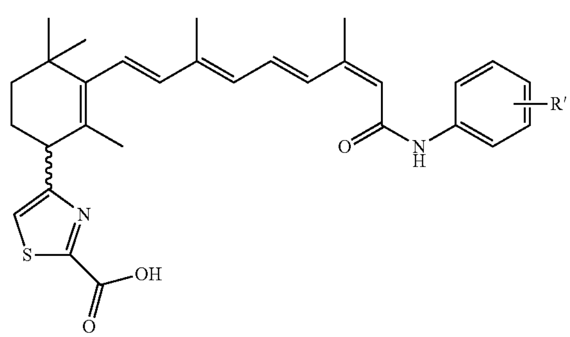 |

TABLE 3-continued

C₄ (R) derivatives

| Compound number Compound name | Structure |
|---|---|
| C23 (2Z,4E,6E,8E)-3,7-dimethyl-N-phenyl-9-(2,6,6-trimethyl-3-(thiazol-5-yl)cyclohex-1-en-1-yl)nona-2,4,6,8-tetraenamide | 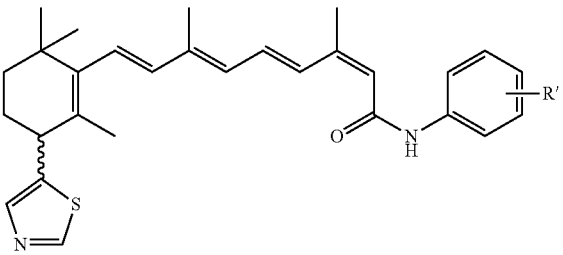 |
| C24 (2Z,4E,6E,8E)-3,7-dimethyl-N-phenyl-9-(2,6,6-trimethyl-3-methylenecyclohex-1-en-1-yl)nona-2,4,6,8-tetraenamide | 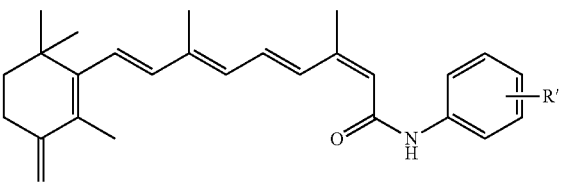 |
| C25 (2Z,4E,6E,8E)-3,7-dimethyl-N-phenyl-9-(4,6,6-trimethylspiro[2.5]oct-4-en-5-yl)nona-2,4,6,8-tetraenamide | 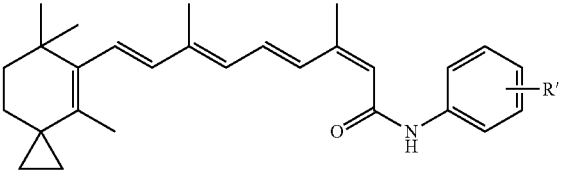 |
| C26 (E)-ethyl 2-(3-((1E,3E,5E,7Z)-3,7-dimethyl-9-oxo-9-(phenylamino)nona-1,3,5,7-tetraen-1-yl)-2,4,4-trimethylcyclohex-2-en-1-ylidene)acetate | 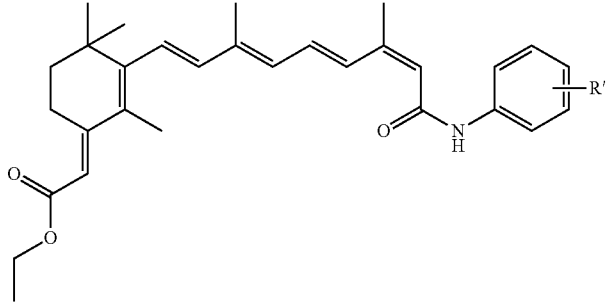 |
| C27 (E)-2-(3-((1E,3E,5E,7Z)-3,7-dimethyl-9-oxo-9-(phenylamino)nona-1,3,5,7-tetraen-1-yl)-2,4,4-trimethylcyclohex-2-en-1-ylidene)acetic acid | 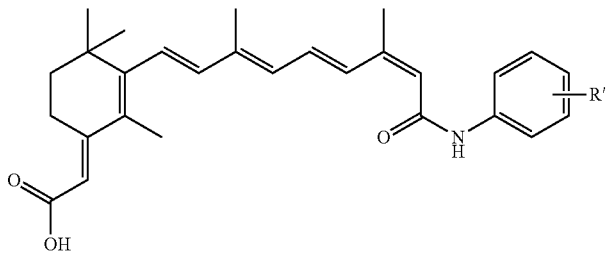 |
| C28 (2Z,4E,6E,8E)-9-((E)-3-benzylidene-2,6,6-trimethylcyclohex-1-en-1-yl)-3,7-dimethyl-N-phenylnona-2,4,6,8-tetraenamide | 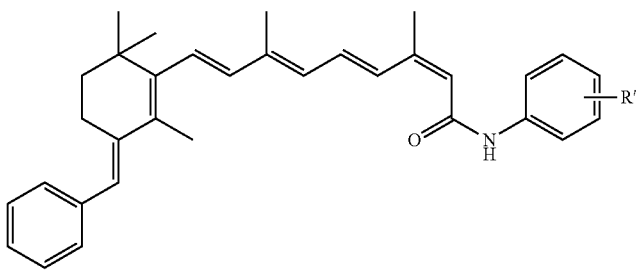 |

TABLE 3-continued

C₄ (R) derivatives

| Compound number Compound name | Structure |
|---|---|
| C29<br>4-((E)-(3-((1E,3E,5E,7Z)-3,7-dimethyl-9-oxo-9-(phenylamino)nona-1,3,5,7-tetraen-1-yl)-2,4,4-trimethylcyclohex-2-en-1-ylidene)methyl)benzoic acid | 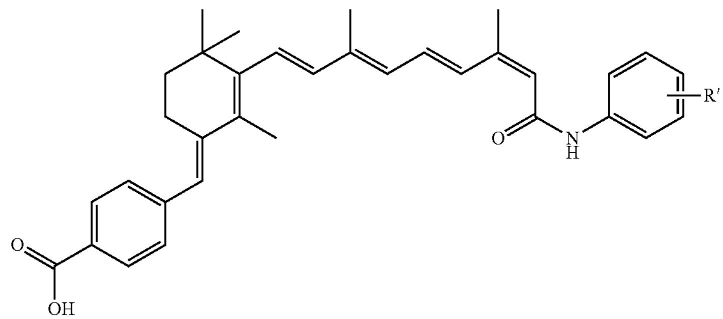 |
| C30<br>(2Z,4E,6E,8E)-9-(3-(1H-benzo[d]imidazol-1-yl)-2,6,6-trimethylcyclohex-1-en-1-yl)-N-methoxy-N,3,7-trimethylnona-2,4,6,8-tetraenamide | 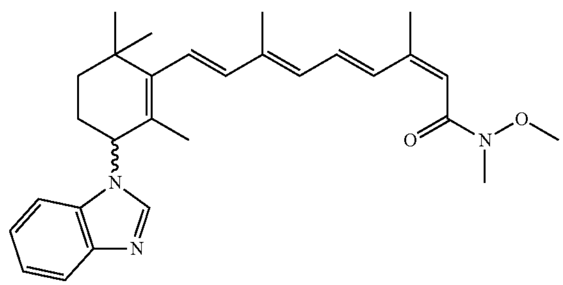 [SMILES: CON(C)C(=O)\C=C(C)/C=C/C=C(C)/C=C/C1=C(C)C(n2cnc3ccccc32)CCC1(C)C] |
| C31<br>(2Z,4E,6E,8E)-N-methoxy-N,3,7-trimethyl-9-(2,6,6-trimethyl-3-(1H-1,2,4-triazol-1-yl)cyclohex-1-en-1-yl)nona-2,4,6,8-tetraenamide | 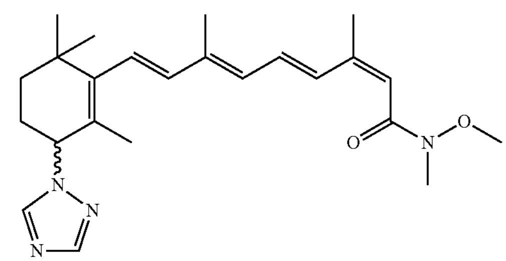 [SMILES: CON(C)C(=O)\C=C(C)/C=C/C=C(C)/C=C/C1=C(C)C(n2cncn2)CCC1(C)C] |
| C32<br>(2Z,4E,6E,8E)-methyl 9-(3-(1H-imidazol-1-yl)-2,6,6-trimethylcyclohexa-1,3-dien-1-yl)-3,7-dimethylnona-2,4,6,8-tetraenoate | 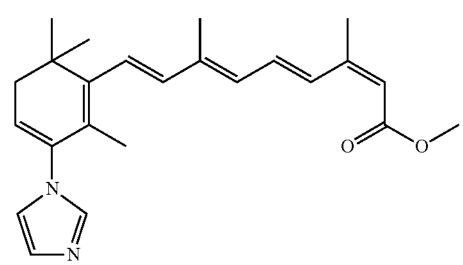 |
| VNHM-1-106 (C33)<br>(2Z,4E,6E,8E)-3,7-dimethyl-N-phenyl-9-(2,6,6-trimethyl-3-(pyridin-3-yl)cyclohexa-1,3-dien-1-yl)nona-2,4,6,8-tetraenamide | 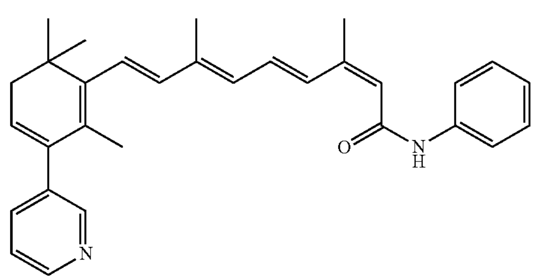 [SMILES: CC1=C(/C=C/C(C)=C/C=C/C(C)=C\C(=O)Nc2ccccc2)C(C)(C)CC=C1c1cccnc1] |

TABLE 3-continued

C_A (R) derivatives

| Compound number Compound name | Structure |
|---|---|
| VNHM-1-104 (C34) (2Z,4E,6E,8E)-7-methyl-N-phenyl-9-(2,6,6-trimethyl-3-(pyrimidin-5-yl)cyclohexa-1,3-dien-1-yl)nona-2,4,6,8-tetraenamide | |
| VNHM-1-94 (C35) (2Z,4E,6E,8E)-N-(4-hydroxybenzyl)-9-(3'-methoxy-2,4,4-trimethyl-4,5-dihydro-[1,1'-biphenyl]-3-yl)-7-methylnona-2,4,6,8-tetraenamide | |
| VNHM-1-108 (C36) (2Z,4E,6E,8E)-methyl 9-(3-hydrazono-2,6,6-trimethylcyclohex-1-en-1-yl)-3,7-dimethylnona-2,4,6,8-tetraenoate | |
| C37 (2Z,4E,6E,8E)-methyl 3,7-dimethyl-9-(2,6,6-trimethyl-3-(phenylamino)cylohex-1-en-1-yl)nona-2,4,6,8-tetraenoate | |

Thioamide Derivatives, Ester, and Ether (Series D):

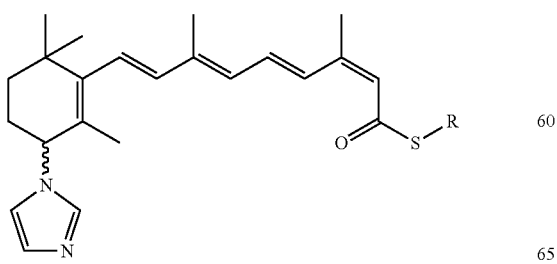

The R group can be, for example, a benzyl group or a heterocyclic group that is mono-, di-, or tri-substituted at either at the para, meta, or ortho position with OH, OMe, CN, $CO_2H$, $CO_2Me$, $SO_2NH_2$; imidazole, 1H-tetrazole, alpha methyl benzyl, pyridine, and their derivatives; Weinreb amide, cyclic amides, and their derivatives. Non-limiting examples of thioamide derivatives, ester, and ether are presented in Table 4.

TABLE 4

Thioamide derivatives, ester, and ether (Series D)

| Compound number Compound name | Structure |
|---|---|
| D1 (2Z,4E,6E,8E)-S-phenyl 9-(3-(1H-imidazol-1-yl)-2,6,6-trimethylcyclohex-1-en-1-yl)-3,7-dimethylnona-2,4,6,8-tetraenethioate | |
| D2 (2Z,4E,6E,8E)-S-(4-hydroxyphenyl) 9-(3-(1H-imidazol-1-yl)-2,6,6-trimethylcyclohex-1-en-1-yl)-3,7-dimethylnona-2,4,6,8-tetraenethioate | |
| D3 (2Z,4E,6E,8E)-S-(2-fluorophenyl) 9-(3-(1H-imidazol-1-yl)-2,6,6-trimethylcyclohex-1-en-1-yl)-3,7-dimethylnona-2,4,6,8-tetraenethioate | |
| D4 (2Z,4E,6E,8E)-S-p-tolyl 9-(3-(1H-benzo[d]imidazol-1-yl)-2,6,6-trimethylcyclohex-1-en-1-yl)-3,7-dimethylnona-2,4,6,8-tetraenethioate | |
| D5 (2Z,4E,6E,8E)-S-m-tolyl 3,7-dimethyl-9-(2,6,6-trimethyl-3-(pyridin-2-yl)cyclohex-1-en-1-yl)nona-2,4,6,8-tetraenethioate | |

TABLE 4-continued

Thioamide derivatives, ester, and ether (Series D)

| Compound number<br>Compound name | Structure |
| --- | --- |
| D6<br>(2Z,4E,6E,8E)-S-(4-hydroxyphenyl) 3,7-dimethyl-9-(2,6,6-trimethyl-3-(thiazol-4-yl)cyclohex-1-en-1-yl)nona-2,4,6,8-tetraenethioate | 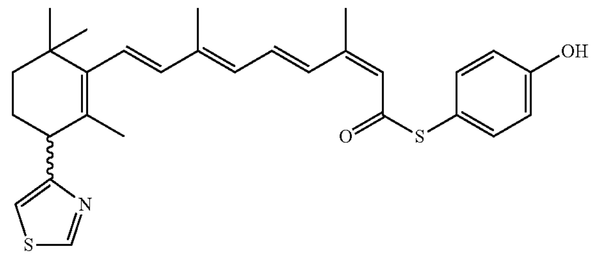 [SMILES: CC1=C(/C=C/C(C)=C/C=C/C(C)=C\C(=O)Sc2ccc(O)cc2)C(C)(C)CCC1c1cscn1] |
| D7<br>(2Z,4E,6E,8E)-S-(3-cyanophenyl) 9-(3-(1H-imidazol-4-yl)-2,6,6-trimethylcyclohex-1-en-1-yl)-3,7-dimethylnona-2,4,6,8-tetraenethioate | 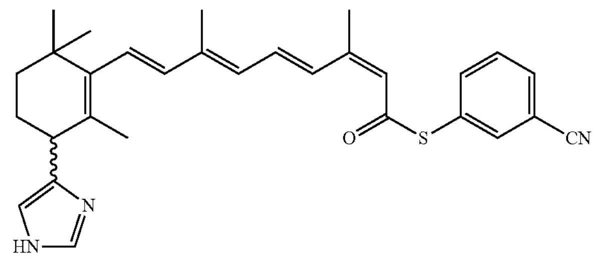 [SMILES: CC1=C(/C=C/C(C)=C/C=C/C(C)=C\C(=O)Sc2cccc(C#N)c2)C(C)(C)CCC1c1c[nH]cn1] |
| D8<br>(2Z,4E,6E,8E)-phenyl 9-(3-(1H-imidazol-1-yl)-2,6,6-trimethylcyclohex-1-en-1-yl)-3,7-dimethylnona-2,4,6,8-tetraenoate | 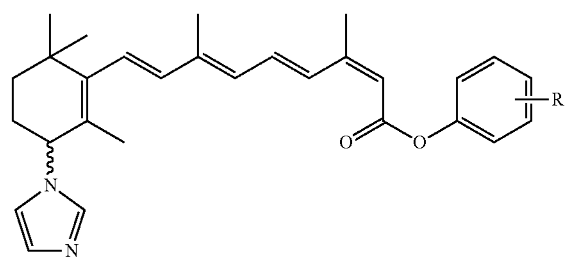 |
| D9<br>1-(3-((1E,3E,5E,7Z)-3,7-dimethyl-9-phenoxynona-1,3,5,7-tetraen-1-yl)-2,4,4-trimethylcyclohex-2-en-1-yl)-1H-imidazole | 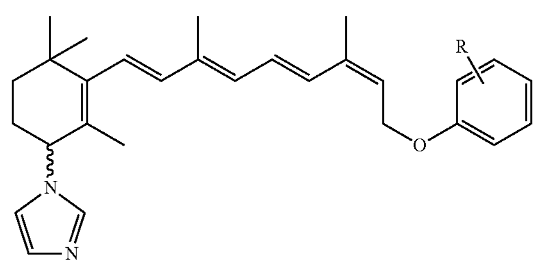 |
| D10<br>N-((2Z,4E,6E,8E)-9-(3-(1H-imidazol-1-yl)-2,6,6-trimethylcyclohex-1-en-1-yl)-3,7-dimethylnona-2,4,6,8-tetraen-1-yl)-N-methylaniline | 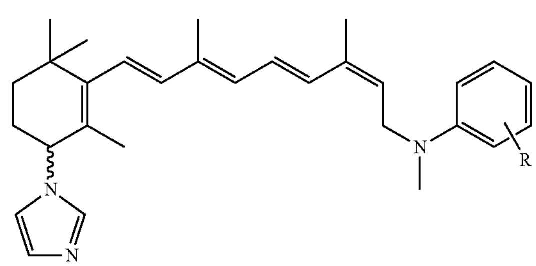 |

TABLE 4-continued

Thioamide derivatives, ester, and ether (Series D)

| Compound number<br>Compound name | Structure |
|---|---|
| D11<br>(Z)-N-((2Z,4E,6E,8E)-9-(3-(1H-imidazol-1-yl)-2,6,6-trimethylcyclohex-1-en-1-yl)-3,7-dimethylnona-2,4,6,8-tetraen-1-ylidene)aniline | 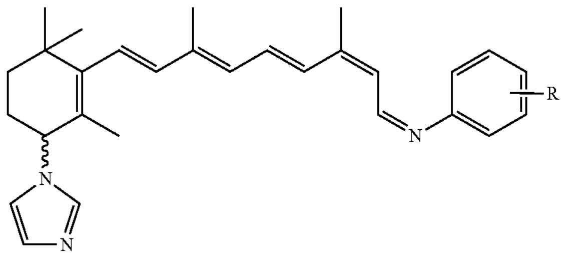 |

Pharmaceutical Composition/Formulation

A pharmaceutical composition, as used herein, refers to a mixture of a compound of the invention with other chemical components, such as carriers, stabilizers, diluents, dispersing agents, suspending agents, thickening agents, and/or excipients. The pharmaceutical composition facilitates administration of the compound to an organism. Pharmaceutical composition containing a compound of the present invention can be administered in therapeutically effective amounts as pharmaceutical compositions by any conventional form and route known in the art including, but not limited to intravenous, oral, rectal, aerosol, parenteral, ophthalmic, pulmonary, transdermal, vaginal, otic, nasal, and topical administration.

A compound of the present invention may be administered in a local rather than systemic manner, for example, via injection of the compound directly into an organ, often in a depot or sustained release formulation. A pharmaceutical composition containing a compound of the present invention may be administered in a targeted drug delivery system, for example, in a liposome coated with organ-specific antibody. The liposomes will be targeted to and taken up selectively by the organ. In addition, a pharmaceutical composition containing a compound of the present invention may be provided in the form of a rapid release formulation, in the form of an extended release formulation, or in the form of an intermediate release formulation.

For oral administration, a compound of the present invention can be formulated, for example, by combining the active compounds with pharmaceutically acceptable carriers or excipients well known in the art. Such carriers enable a compound of the present invention to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds of the present invention, optionally grinding the resulting mixture, and processing the mixture of granules, after adding suitable auxiliaries, if desired, to obtain tablets or dragee cores. Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. In certain instances, a gelatin is alkaline processed. The push-fit capsules can contain a compound of the present invention as an active ingredient in admixture with filler such as lactose, binders such as starches, and/or lubricants such as talc or magnesium stearate and, optionally, stabilizers. In soft capsules, the active ingredient may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, a pharmaceutical composition may take the form of tablets, lozenges, or gels formulated in conventional manner. Parental injections may involve for bolus injection or continuous infusion. A pharmaceutical composition containing a compound of the present invention may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active ingredient in water-soluble form. Additionally, suspensions of the active ingredient may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, for example, sterile pyrogen-free water, before use.

In some embodiments, pharmaceutical formulations are prepared as an amorphous solid dispersion. For example, the pharmaceutical formulation is a spray-dried formulation of the active compound in a polymer matrix. The pharmaceutical formulation may also be prepared by hot melt extrusion.

A compound of the present invention can be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Formulations suitable for transdermal administration of a compound of the present invention may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of a compound of the invention can be accomplished by means of iontophoretic patches and the like. Additionally, transdermal patches can provide controlled delivery of a compound of the invention. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, a compound of the present invention may be in a form as an aerosol, a mist or a powder. A pharmaceutical composition containing a compound of the present invention may be conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

A compound of the present invention may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of a compound of the present invention are administered in a pharmaceutical composition to a mammal having a disease or condition to be treated. In some embodiments, the mammal is a human. A therapeutically effective amount can vary widely depending on the severity of the disease, the age and relative health of the subject, the potency of the compound used and other factors. A compound of the present invention can be used singly or in combination with one or more therapeutic agents as components of mixtures.

A pharmaceutical composition containing a compound of the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A pharmaceutical composition containing a compound of the present invention may be manufactured in a conventional manner, such as, by way of example only, by means of conventional mixing, dissolving, granulating, dragee-making, levigating, emulsifying, encapsulating, entrapping or compression processes.

A pharmaceutical composition may include at least one pharmaceutically acceptable carrier, diluent or excipient and a compound of the present invention as an active ingredient in free-base form, or in a pharmaceutically acceptable salt form. In addition, the methods and pharmaceutical compositions described herein may include the use of N-oxides, crystalline forms (also known as polymorphs), as well as active metabolites of these compounds having the same type of activity.

Methods for the preparation of a pharmaceutical composition containing a compound of the present invention include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The pharmaceutical composition may be in liquid solutions or suspensions, solid forms suitable for solution or suspension in a liquid prior to use, or as emulsions. The pharmaceutical composition may also contain minor amounts of nontoxic, auxiliary substances, such as wetting or emulsifying agents, pH buffering agents, and so forth.

Methods of Administration and Treatment Methods

A compound of the present invention can be used in the preparation of medicaments for treating or preventing Mnk1/2 and androgen receptor (AR) associated conditions including but not limited to breast cancer, prostate cancer, bladder cancer, pancreatic cancer, hepatocellular carcinoma, benign prostatic hyperplasia (BPH), Kennedy's disease and hematologic cancers. In addition, a compound of the present invention can be used, for example, as a therapeutic agent alone or in combination with other therapeutic agents, for treating various dermatological (skin) conditions, including but not limited to acne, psoriasis, wrinkling, and photoaged skin.

In a human subject in need thereof a method for treating any of the diseases or conditions described herein in a subject in need of such treatment involves administration of a pharmaceutical composition containing at least one compound of the present invention (or a pharmaceutically acceptable salts, pharmaceutically acceptable N-oxides, pharmaceutically active metabolites, pharmaceutically acceptable prodrugs, and pharmaceutically acceptable solvates thereof) in a therapeutically effective amount to the subject.

A pharmaceutical composition containing a compound of the present invention can be administered for prophylactic and/or therapeutic treatments. In therapeutic applications, the compositions are administered to a patient already suffering from a disease or condition, in an amount sufficient to cure or at least partially arrest the symptoms of the disease or condition, or to cure, heal, improve, or ameliorate the condition itself. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

Where the patient's condition does not improve, upon the doctor's discretion, the compositions may be administered chronically, that is, for an extended period of time, including throughout the duration of the patient's life in order to ameliorate or otherwise control or limit the symptoms of the patient's disease or condition. Where the patient's status does improve, upon the doctor's discretion, the administration of the compositions may be given continuously or temporarily suspended for a certain length of time (i.e., a "drug holiday"). Once improvement of the patient's conditions has occurred, a maintenance dose is administered if necessary. Subsequently, the dosage or the frequency of administration, or both, can be reduced, as a function of the symptoms, to a level at which the improved disease or condition is retained. Patients may require intermittent treatment on a long-term basis upon any recurrence of symptoms.

In certain instances, it may be appropriate to administer therapeutically effective amounts of at least one of the compounds of the present invention (or a pharmaceutically acceptable salts, pharmaceutically acceptable N-oxides, pharmaceutically active metabolites, pharmaceutically acceptable prodrugs, and pharmaceutically acceptable solvates thereof) in combination with another therapeutic agent. By way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds of the present invention with another therapeutic agent (which also includes a therapeutic regimen) that also has therapeutic benefit. In any case, regardless of the disease or condition being treated, the overall benefit experienced by the patient may simply be additive of the two therapeutic agents or the patient may experience a synergistic benefit. Where the compounds of the present invention are administered in conjunction with other therapies, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

The multiple therapeutic agents (one of which is one of the compounds of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents. Multiple therapeutic combinations are envisioned.

In addition, a compound of the present invention may also be used in combination with procedures that may provide additional or synergistic benefit to the patient. By way of example only, patients are expected to find therapeutic and/or prophylactic benefit in the methods described herein, wherein pharmaceutical composition of the invention and/or combinations with other therapeutics are combined with genetic testing to determine whether that individual is a carrier of a mutant gene that is known to be correlated with certain diseases or conditions.

A compound of the present invention and combination therapies may be administered before, during or after the occurrence of a disease or condition, and the timing of administering the composition containing a compound can vary. Thus, for example, the compounds can be used as a prophylactic and can be administered continuously to subjects with a propensity to conditions or diseases in order to prevent the occurrence of the disease or condition. The compounds and compositions may be administered to a subject during or as soon as possible after the onset of the symptoms. The initial administration can be via any route practical, such as, for example, an intravenous injection, a bolus injection, infusion, a pill, a capsule, transdermal patch, buccal delivery, and the like, or combination thereof. A compound is preferably administered as soon as is practicable after the onset of a disease or condition is detected or suspected, and for a length of time necessary for the treatment of the disease. The length of treatment can vary for each subject, and the length can be determined using known criteria.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Examples

Biological Studies: Materials and Methods
Cell Culture and Western Blotting

MCF-7, MDA-MB-231, MDA-MB-468 and SKBR-3 human breast cancer cells and LNCaP, PC-3, and CWR22Rv1 human prostate carcinoma cells (American Type Culture Collection, Manassas, Va., USA) were maintained in RPMI 1640 media (Gibco-Life Technologies, Grand Island, N.Y., USA) supplemented with 10% fetal bovine serum and 1% penicillin/streptomycin. Western blotting was done as mentioned previously,[8, 13b] using the following antibodies: AR, Bad, Bax, Bcl-2, eIF4E, Mnk1, Mnk-2, N-cadherin, PARP, peIF4E$^{ser209}$ purchased from Cell Signaling Technology, Danvers, Mass., USA. Anti- Mnk2 was purchased from Sigma-Aldrich and normal rabbit IgG, cyclin D1 was from Santa Cruz Biotechnology, CA, USA.

Cell Proliferation Analysis

Cells were plated (2500 cells/well) in 96 well plates and treated with or without specified compounds as described previously.[8a, 12b]

Wound Healing Assay

Wound healing assay and matrigel invasion assay were also conducted as described previously using highly metastatic PC-3 cells following treatment with 5 μM of RRs for 24 h.[8a,26]

siRNA Transfection and Luciferase Assay siRNA (100 nM) was transfected into LNCaP cells using Lipofectamine® 2000 Transfection reagent (Invitrogen) as per manufacturer's protocol. Protein silencing was confirmed by immunoblot analysis. For cell growth assay experiments, transfection complex were removed after 18 h, cells were washed twice with PBS and replaced with growth medium. 24 h later drug was added and harvested after 72 h. For Western blot experiment, transfection complexes were washed off after 18 h and replaced with phenol free media for 24 h. Cells were then treated with 20 μM of VNLG-152 for an additional 24 h and cells were lysed using RIPA lysis buffer.[8b, 27] Luciferase assay was conducted in LNCaP cells using the Dual Luciferase kit (Promega) as described earlier.[8b, 13b]

In Vivo Anti-Tumor Studies:

All animal studies were performed according to the guidelines and approval of the Animal Care Committee of the University of Maryland School of Medicine, Baltimore (UMB). Female Athymic Nude mice or male SCID (Charles Rivers Laboratories or UMB facilities) at 4-6 weeks of age were maintained in a pathogen-free environment. MDA-MB-231 ($10 \times 10^6$) cells were subcutaneously implanted into Athymic Nude mice and CWR22Rv1 ($1 \times 10^6$) cells into male SCID mice. Mice bearing established tumors (~100 mm³) were randomized into treatment groups of 6 and dosed with vehicle (40% β-cyclodexdrin in ddH₂O), or compounds 20 and 22 (i.p., formulated in 40% β-cyclodexdrin in ddH₂O, once daily, 5 days a week for 28 days).

In Vivo Anti-Tumor Activity:

The National Cancer Institute (NCI) criteria[23] were used to determine tumor growth efficacy of our compounds. Thus, percent test or treatment/control (% T/C), defined as the ratio of the median tumor volume for the treated group versus control group, was calculated as % T/C=[(median tumor volume of treated group at day 28)/(median tumor volume of control group at day 28)]×100. By these criteria, agents which confer % T/C<42% are considered minimally effective/active, and % T/C<10% are considered to be highly active.[23]

Statistical Analysis

All experiments were carried out in at least triplicates and are expressed as mean±S.E. where applicable. Treatments were compared to controls using the Student's t-test with either GraphPad Prism or Sigma Plot. Differences between groups were considered statistically significant at P<0.05.

Example 1: Effects of 13-Cis Retinamides on the Growth of Breast and Prostate Cancers Cells In Vitro The effects of the 13-cis novel retinamides of the present invention on human cancer cell proliferation using a variety of breast and prostate cancer cells lines using our previously described MTT assay procedures were determined.[8,12b,21]

The results ($GI_{50}$ values) are summarized in TABLES 5 and 6. Growth inhibitory concentrations ($GI_{50}$ values) are the concentrations of compounds that cause 50% growth inhibition obtained from dose-response curves. The clinically relevant retinoids, ATRA and 4-HPR and the Mnk inhibitor, cercosporamide were used as comparators in the assays.

Anti-Proliferative Activities in Breast Cancer Cell Lines:

As described earlier, the structural modification focused on modifications of the terminal amide, cyclohexene ring and C-4 substituents. As presented in TABLE 5, several important generalizations emerge from the anti-proliferative data. First, compounds of the present invention, including Compounds 16-25, possess higher anti-proliferative activities towards all four breast cancer cell lines than the positive controls, ATRA, 4-HPR and the Mnk inhibitors, as evidenced by the lower $GI_{50}$ values (TABLE 5).

TABLE 5

Inhibitory concentrations ($GI_{50}$, μM) of NRs and reference compounds on the Growth of Human Breast Cancer Cells in Vitro

| Cpds. | $GI_{50}s$ (μM)[a] MCF-7 | $GI_{50}s$ (μM)[a] MDA-MB-231 | $GI_{50}s$ (μM)[a] MDA-MB-468 | $GI_{50}s$ (μM)[a] SKBR-3 |
|---|---|---|---|---|
| 16 | 1.90 | 1.74 | 2.54 | 1.73 |
| 17 | 1.99 | 13.05 | 6.83 | 3.89 |
| 18 | 1.09 | 4.67 | 3.03 | 3.89 |
| 19 | 0.40 | 4.95 | 4.57 | 25.11 |
| 20 | 5.69 | 8.51 | 6.76 | 16.98 |
| 21 | 9.77 | 5.88 | 7.24 | 10.71 |
| 22 | 0.16 | 2.23 | 2.70 | 2.45 |
| 23 | 1.93 | 1.41 | 2.45 | 5.50 |
| 24 | 1.81 | 1.65 | 2.45 | 5.50 |
| 25 | 1.90 | 2.88 | 13.48 | 1.41 |
| 33 | n/d | n/d | n/d | n/d |
| 34 | n/d | n/d | n/d | n/d |
| 35 | 8.32 | 25.11 | 39.81 | 47.40 |
| 36 | n/d | n/d | n/d | n/d |
| 37 | 8.75 | 26.91 | 50.11 | 42.24 |
| 38 | 7.01 | 26.91 | 22.90 | 30.98 |
| 39 | 4.96 | 11.48 | 19.05 | 11.48 |
| 40 | 2.96 | 14.45 | 23.44 | 23.99 |
| ATRA[b] | | 14.12 | 14.12 | 22.90 |
| 4-HPR | 4.65 | 11.05 | 6.02 | 3.98 |
| Cerco.[b] | | 43.65 | 47.86 | 26.02 |

[a]The $GI_{50}$ were determined from dose-response curves (by nonlinear regression analysis using GraphPad Prism) compiled from at least three independent experiments using indicated BC cells, SEM < 10%, and represents the compound concentration required to inhibit cell growth by 50%.
[b]Previously reported in Ramalingam S, et al.[8a]
n/d = not determined (≥60% inhibition of MCF-7 cells growth at 10 μM).

Second, for each compound, the anti-proliferative activities towards the BC cell lines varied significantly. In general, the MCF-7 cell line was the most sensitive, while the SKBR-3 were the least sensitive to these compounds. Third, for a given BC cell line, the anti-proliferative activity depends largely on the structure of the NR, which in turn depends largely on the nature of the C-4 heterocycle and cyclohexen/cyclohexadiene ring. Compounds with the imidazole tethered to C-4 of the cyclohexene ring (Compounds 16-25) exhibit more potent anti-proliferative activities than compounds with phenyl (Compounds 33 and 34), pyridine (Compounds 35-37) or pyrimidine (Compounds 38-40) tethered to C-4 of the cyclohexadiene ring. Compared to Compound 16 which possesses an unsubstituted amide phenyl ring, compounds with substituted hydroxyl (Compounds 17 and 18) or fluoro (Compounds 19 and 20) groups displayed mixed anti-proliferative activities, but in general were either equipotent or less active than Compound 16. The only exception was p-fluoro compound (Compound 19) with a $GI_{50}$=0.4 μM against MCF-7 cells was ~4.8 fold more potent than Compound 16 ($GI_{50}$=1.90 μM). Insertion of a methylene moiety between the amide and phenyl group clearly led to decreased anti-proliferative activities (compare $GI_{50}$s of Compound 16: 1.74-2.54 µM to $GI_{50}$s of Compound 21: 5.88-10.71 µM). However, ortho/para hydroxyl or fluoro substitutions to benzyl group of Compound 21 to give Compounds 22-24 led to enhanced anti-proliferative activities across the four BC cell lines. Amongst these three compounds, Compound 22 was the most potent with $GI_{50}$ values of 0.16, 2.23, 2.70 and 2.45 µM versus MCF-7, MDA-MB-231, MDA-MB-468 and SKBR-3 cell lines, respectively. Related Compound 25 with an ethylene moiety between the amide and p-hydroxyl group led to varied anti-proliferative activities. It is notable that Compound 25 amongst these compounds, exhibited the best activity ($GI_{50}$=1.41 µM) against SKBR-3 cell line.

Anti-Proliferative Activities in Prostate Cancer Cell Lines:

The $GI_{50}$ values of Compounds 16-22 against three human prostate cancer cell lines, including, LNCaP, CWR22Rv1 and PC-3 were determined and compared to the $GI_{50}$ values of clinically relevant drugs, ATRA, 4-HPR, casodex and MDV3100 (enzalutamide) (TABLE 6). In general, the compounds were more potent than ATRA, but were equipotent to 4-HPR, casodex and MDV3100. The PC-3 cell line was the least sensitive to all the compounds tested. Compounds 20 and 22 exhibited the most potent anti-proliferative activities across the three cell lines.

TABLE 6

Inhibitory concentrations ($GI_{50}$, µM) of NRs and reference compounds on the Growth of Human Prostate Cancer Cells in Vitro

| Cpds. | $GI_{50}$s (µM)[a] LNCaP | $GI_{50}$s (µM)[a] CWR22Rv1 | $GI_{50}$s (µM)[a] PC-3 |
|---|---|---|---|
| 16 | 2.69 | 1.28 | 8.91 |
| 17 | 3.54 | 3.89 | 11.74 |
| 18 | 3.23 | 2.23 | 15.48 |
| 19 | 3.89 | 8012 | 30.19 |
| 20 | 2.69 | 2.04 | 5.62 |
| 21 | n/d | n/d | n/d |
| 22 | 1.69 | 1.86 | 3.54 |
| ATRA[b] | 47.86 | 25.11 | 36.3 |
| 4-HPR[b] | 2.69 | 3.23 | 3.54 |
| Casodex[b] | 2.61 | 3.81 | 9.15 |
| MDV3100[b] | 2.88 | 3.34 | 9.15 |

[a]The $GI_{50}$ were determined from dose-response curves (by nonlinear regression analysis using GraphPad Prism) compiled from at least three independent experiments using LNCaP cells, SEM < 10%, and represents the compound concentration required to inhibit cell growth by 50%.
[b]Previously reported in Ramamurthy V et al.[8b]
n/d = not determined.

Figure 3C:
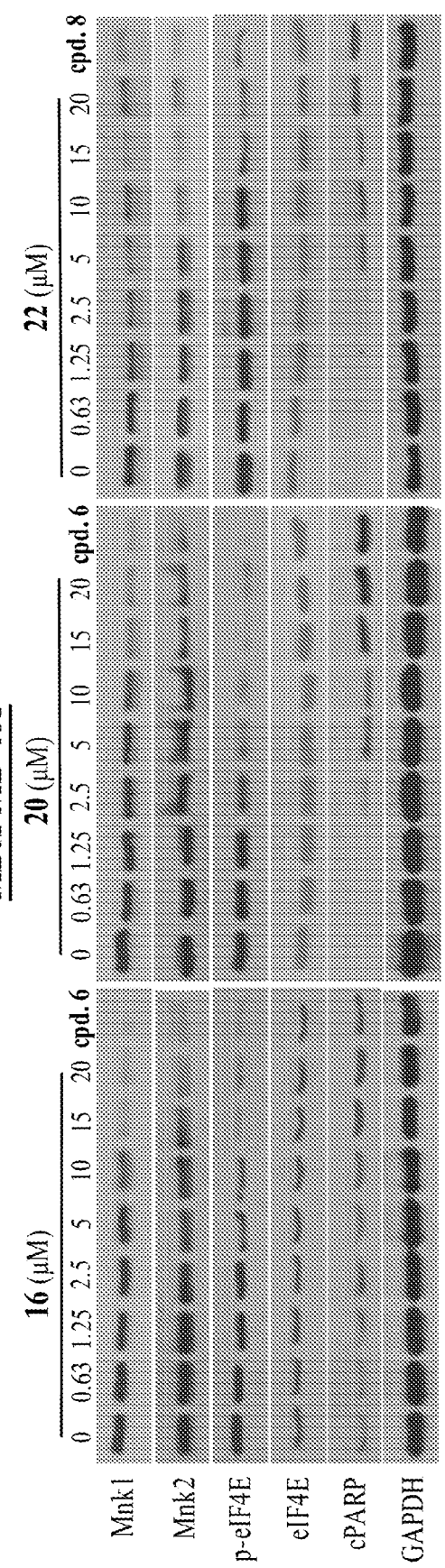
FIGS. 3(A)-(B) illustrate effects of the novel retinamides of the present invention on Mnk1 and 2, peIF4E, eIF4E and cPARP proteins in MCF-7 cells.

Example 2: In Vitro Characterization of Compounds 16, 20 and 22 in Breast Cancer Cell Lines As we previously reported, the anti-proliferative effects of the 1st generation MNKDAs in BC cells was due to degradation of Mnk1/2 with subsequent depletion of peIF4E and induction of apoptosis.[8a] To determine if these compounds modulate Mnk1/2 and related oncogenic proteins, the inventors performed western blot of lysates from MCF-7, MDA-MB-231 and MDA-MB-468 human breast cancer cells treated with Compounds 16, 20, and 22, or with vehicle (DMSO, negative control), or Compound 6 (positive control). Equal protein concentrations from MCF-7 (FIG. 3A), MDA-MB-231 (FIG. 3B) and MDA-MB-468 (FIG. 3C) cells treated for 24 hours with Compounds 16, 20 and 22 at the various concentrations as indicated and Compound 6 (20 µmol/L) were separated by SDS-PAGE and western blots probed with antibodies to Mnk1 and 2, peIF4E, eIF4E and cPARP. Vehicle treated cells were included as control and all blots were reprobed for GAPDH for loading control. FIG. 3A-C shows that the three compounds significantly and dose-dependently, reduced the expressions of Mnk1, Mnk2 and peIF4E, with no noticeable effects on the expression of total eIF4E. The compounds also caused dose-dependent formation of c-PARP which indicates induction of cell death (apoptosis).

Figure 4:
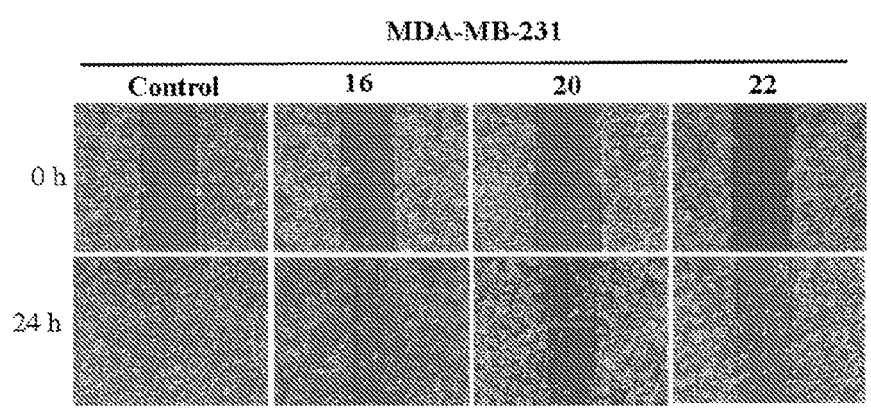
FIG. 4 illustrates effects of the novel retinamides of the present invention on MDA-MB-231 cell migration.

Based on previous studies with closely related compound,[8] the inhibitory effects of Compounds 16, 20 and 22 on cell migration were evaluated, using the human metastatic BC cell line, MDA-MB-231 by wound-healing assay. MDA-MB-231 cells ($5 \times 10^5$ cells/well) were seeded on Boyden chamber, grown to confluence and scratches made at experimental tome zero. The cells were treated with indicated compounds (5 µM each) for 24 h. Representative photomicrographs of initial and final wounds are shown at 100× magnification. FIG. 4 shows that the Compounds 20 and 22 significantly inhibited migration of MDA-MB-231 cells compared to the control. At 24 hours after cell monolayers were wounded, control cells had completely filled in the scratched area.

Example 3: In Vitro Characterization of Compounds 16, 20 and 22 in Prostate Cancer Cell Lines Previously, we demonstrated that the anti-tumor activity of the early NRs in prostate cancer cells was due to simultaneous inhibition of the Mnk/eIF4E and androgen receptor (AR) signaling pathways.[8b] Similar to studies described above, the inventors performed western blot of lysates from LNCaP human prostate cancer cells treated with Compounds 16, 20, and 22, or with vehicle (DMSO, negative control), or Compound 6 (positive control). Equal protein concentrations from LNCaP cells treated with Compounds 16, 20 and 22 at different concentrations (0.6-20 µM) for 24 hours were separated by SDS-PAGE and western blots probed with antibodies to fAR, Mnk1/2, peIF4E, cyclin D1 and cleaved PARP. Vehicle treated cells were included as a control and all blots were reprobed for β-actin for loading control. FIG. 5A shows that the three compounds significantly and in a dose-dependent fashion, reduced the expressions of fAR, Mnk1 and Mnk2, with no noticeable effects on the expression of total eIF4E. In addition, the compounds caused significant depletion of oncogenic cyclin D1 and they each induced cleaved PARP (c-PARP), a reliable marker of apoptotic cell death (FIG. 5B).

Figure 6:
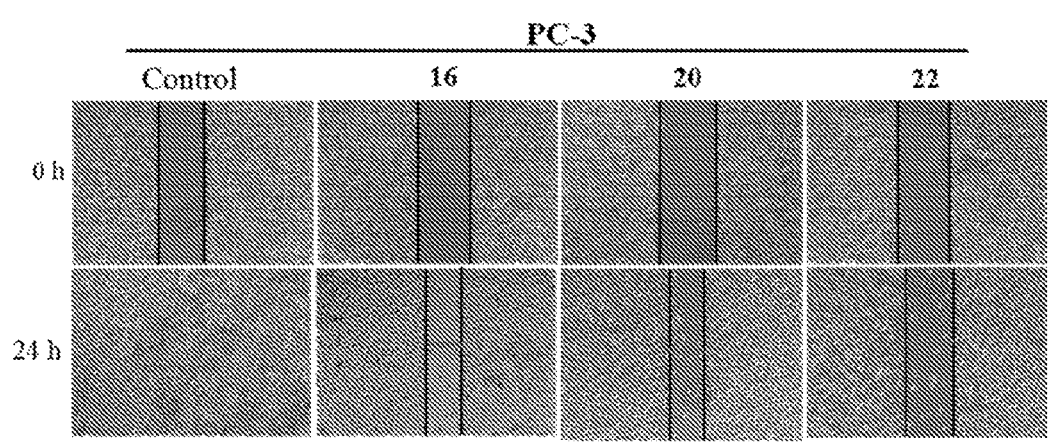
FIG. 6 illustrates effects of the novel retinamides of the present invention on PC-3 cell migration.

Based on previous studies with closely related compound,[8] the inhibitory effects of Compounds 16, 20 and 22 on cell migration were evaluated, using the human metastatic PC cell line, PC-3 by wound-healing assay. PC-3 cells ($5 \times 10^5$ cells/well) were seeded on Boyden chamber, grown to confluence and scratches made at experimental tome zero. The cells were treated with indicated compounds (5 µM each) for 24 hours. Representative photomicrographs of initial and final wounds are shown at 100× magnification. FIG. 6 shows that the three compounds significantly inhibited migration of PC-3 cells compared to the control. At 24 hours after cell monolayers were wounded, control cells had completely filled in the scratched area.

Since AR is a major driver of proliferation in PCa,[22] the effect of Compounds 16, 20 and 22 on AR transcriptional activity in LNCaP cells was next examined. LNCaP cells dual transfected with ARR2-Luc and the Renilla luciferase reporting vector pRL-null and treated with 10 μM of specified compounds for 18 hours in the presence of 10 nmol/L dihydrotestosterone (DHT). Control represents baseline activity without androgen stimulation. Androgen stimulated luciferase activity (luminescence) was measured in a victor 1420 plate reader. The results are presented in FIG. 7 as the fold induction (i.e., the relative luciferase activity of the treated cells divided by that of control) normalized to that of *Renilla*,*=P<0.05; ♣=P<0.01 compared with DHT alone treated cells.

Figure 7:
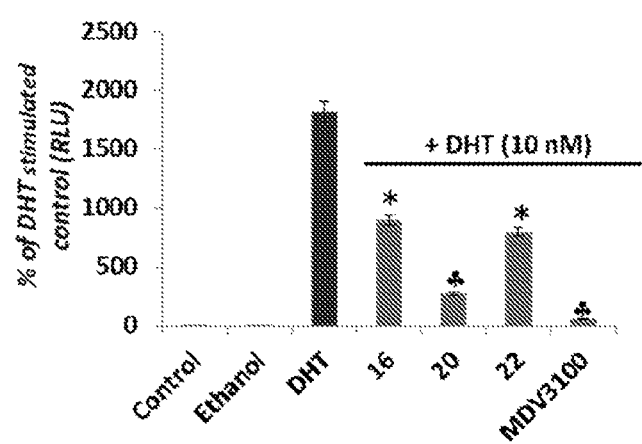
FIG. 7 illustrates effects of the novel retinamides of the present invention on dihydrotestosterone (DHT)-induced AR transactivation in LNCaP cells.

As shown in FIG. 7, 24-hour exposure of LNCaP cells to lead NRs, Compounds 16, 20 and 22 (10 μM) resulted in a 2-4-fold dramatic inhibition of DHT induced AR transcriptional activity that was however less potent than that observed upon clinically available MDV3100 treatment. Of these leads, Compound 20 was the most potent.

Figure 8A:
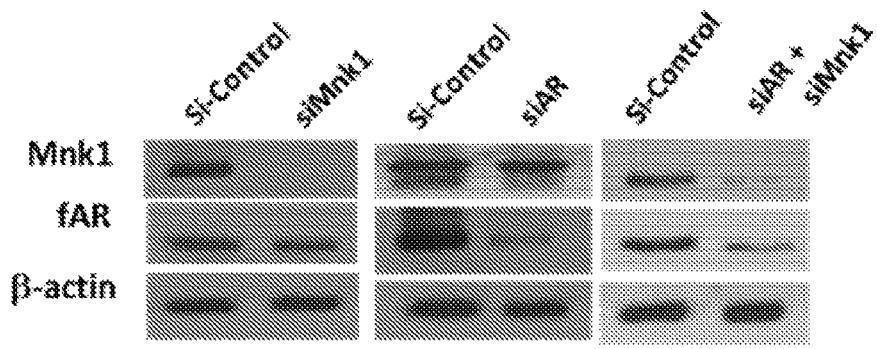
FIG. 8A illustrates a western blot analysis of the expression of fAR and Mnk1 in LNCaP cells transfected with 50 nM of siAR, siMnk1 and combinations for 18 hours.
Figure 8B:
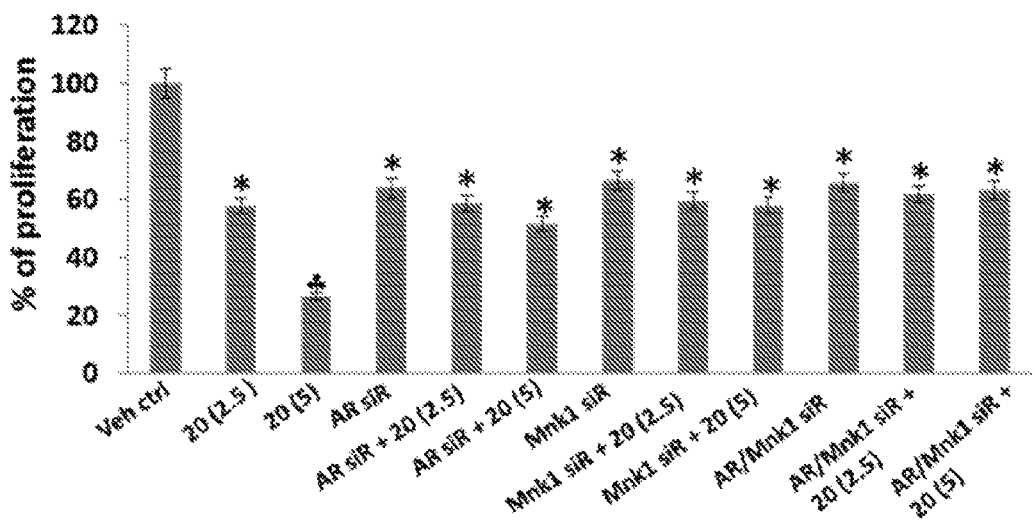
FIG. 8B illustrates the effect of Compound 20 of the present invention (in µM concentration) on cell proliferation in LNCaP cells transfected with 50 nM of siAR, siMNK1 and combinations as determined by MTT assay. The histogram bars represent the mean±SEM of three independent experiments and after normalizing to control cells, * indicates P<0.05, * indicates P<0.01 compared with vehicle treated control.

To confirm whether AR and Mnk1 are the major anti-cancer targets of these compounds on LNCaP cells, the percentage of cell survival in LNCaP cells was analyzed by MTT assay following transient transfection with AR siRNA and/or Mnk1 siRNA for 18 hours. Here, data for Compound 20, which are identical to data for Compounds 16 and 22, are presented in FIG. 8. The efficiency of transfection was confirmed by western blot analysis, wherein protein lysates obtained from the transfected cells after AR siRNA transfection showed a temporal decrease in total AR protein and cells transfected with Mnk1 siRNA showed a temporal decrease in the expression Mnk1 compared to scrambled (si-control) treated controls after 18 h of transfection (FIG. 8A). Cells co-treated with AR and Mnk1 siRNA showed a remarkable decrease in the expression of both AR and Mnk1 compared to scrambled siRNA treated cells (FIG. 8A). MTT assay revealed that transient transfections with AR and/or Mnk1 siRNA caused a considerable decrease (~40%) in LNCaP cell viability compared to control (FIG. 8B, compare lane 1 to lanes 4, 7 and 10). Treatment of LNCaP cells (un-transfected) with 5 μM concentration of Compound 20 for 72 hours showed a robust reduction in cell viability (lane 3). LNCaP cells harboring AR (lane 6) or Mnk1 (lane 9) knockdown also displayed a sensible decrease in cell viability upon treatment with 5 μM of Compound 20, compared to the Mnk1 and AR siRNA alone treated counterparts (lanes 4 and 7, respectively). However, LNCaP cells with double knockdown of AR and Mnk1 genes (lane 12) did not show any significant decrease in cell viability upon agent treatment compared to cells co-treated with Mnk1 and AR siRNA (FIG. 8B, lane 10). These results strongly suggest that Mnk1 and AR are prime targets of Compounds 16, 20 and 22, and that loss of both these targets abolishes the potent growth-inhibitory effects mediated by these agents in LNCaP cells.

Example 4: Inhibition of Breast and Prostate Cancer Tumor Growth In Vivo

To determine whether the anti-cancer effects exhibited by the lead compounds in cell cultures could be replicated in animal models, anti-tumor xenograft studies in two well-established aggressive models of human breast (MDA-MB-231) and prostate (CWR22Rv1) cancers were conducted.

Figure 9A:
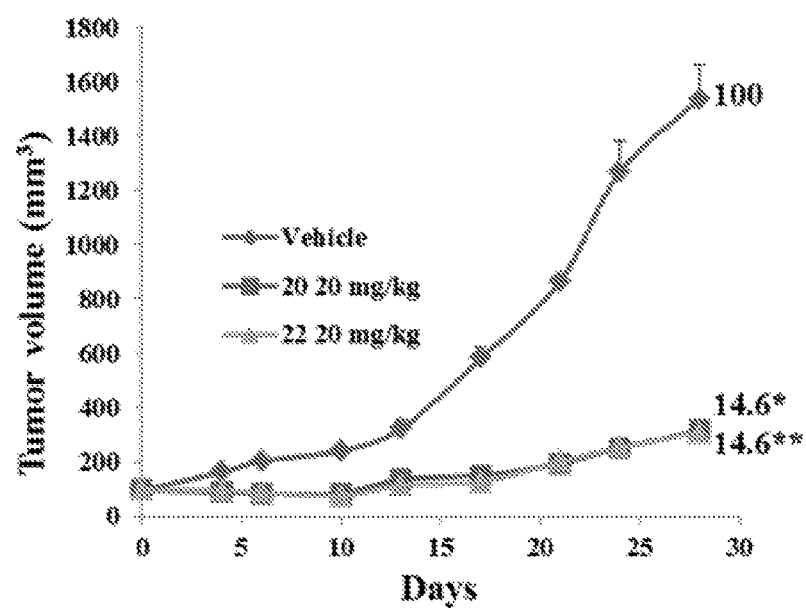
FIG. 9A illustrates the significant suppression of tumor growth in nude female mice bearing MDA-MB-231 xenograft tumors (n=6/group) treated with Compound 20 or 22 of the present invention, administered intraperitoneal 20 mg/kg/day, 5 days per week for 28 days. % T/C values are indicated to the right of each growth curve and the error bars are the SEM. For Compound 20, * indicates p=0.0001 and for Compound 22, ** indicates p=0.0001).
Figure 9B:
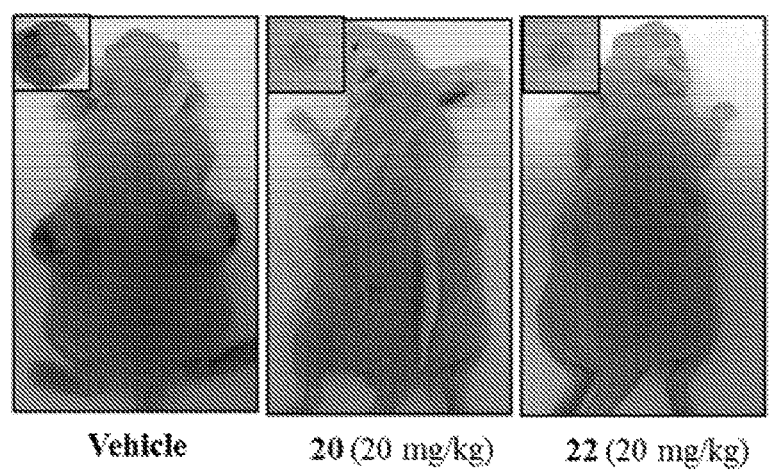
FIG. 9B presents representative photos of the tumor-bearing mice and excised tumors in the control and the two treatment groups at termination of experiment (day 28).

MDA-MB-231 Anti-Tumor Efficacy Study:

First, in vivo antitumor efficacy of Compounds 20 and 22 was evaluated in mice bearing MDA-MB-231 triple negative BC (TNBC) xenografts that were administered intraperitoneal (i.p.) 20 mg/kg Compound 20 or 22 5x/week over 28 days, which resulted in an 85.4% suppression of tumor growth. Indeed, the two compounds were equipotent (FIG. 9A). Thus, the tumor growth inhibition, measured as % T/C=14.6%, classified these compounds as highly efficacious according to the National Cancer Institutes (NCI'S) criteria.[23] Tumor growth inhibition (% T/C), is defined as the ratio of the median tumor volume for the treated versus control group. Representative photos of the tumor-bearing mice in the control and the two treatment groups at termination of experiment (day 28) are presented in FIG. 9B. Importantly, the mice in the treated group did not lose body weight (FIG. 9C) and display any signs of toxicity, suggesting no apparent adverse events of the compounds.

Molecular Analysis of Tumors:

To assess their in vivo mode of action, we evaluated the effects of Compounds 20 and 22 on Mnk-1, peIF4E and their downstream targets. As expected, tumors from mice treated with Compounds 20 or 22 showed depletion of Mnk1/2, peIF4E, cyclide D1 and anti-apoptotic Bcl-2 with concomitant up-regulation of pro-apoptotic proteins, Bad and Bax (FIG. 9D).

Figure 10A:
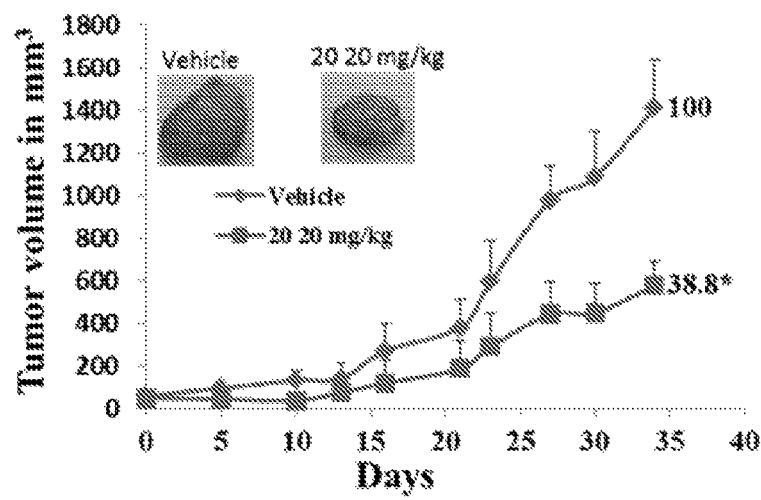
FIG. 10A illustrates the significant suppression of tumor growth in castrated SCID male mice bearing CWR22Rv1 xenograft tumors (n=6/group) treated with by Compound 20 of the present invention, administered intraperitoneal 20 mg/kg/day, 5 days per week for 28 days. % T/C values are indicated to the right of each growth curve and the error bars are the SEM. * indicates p=0.0001).
Figure 10B:
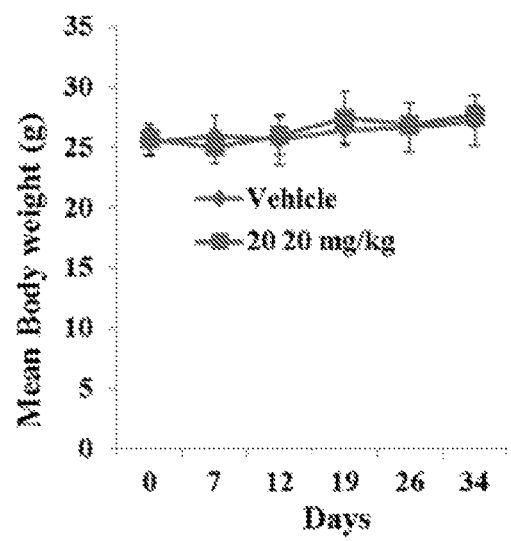
FIG. 10B illustrates the changes in the body weight of the mice during the course of treatments. Animals were monitored for changes in body weight as a surrogate marker for toxicity in control and treatment groups.

CWR22Rv1 Anti-Tumor Efficacy Study:

Similarly, treatment of Compound 20 to castrated mice bearing the aggressive CWR22Rv1 xenografts cause significant inhibition of tumor growth with % T/C value of 38.8, i.e., 61.2% suppression of tumor growth (FIG. 10A). We also found that the body weights were comparable in mice either from vehicle control or treatment groups (FIG. 10B), suggesting no apparent adverse effects of compound 20.

Figure 10C:
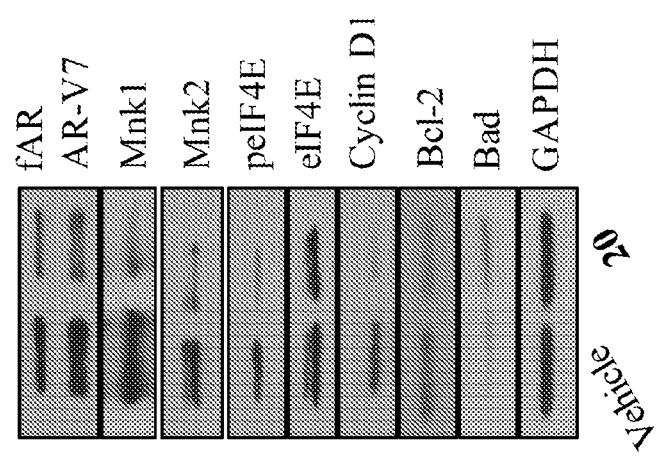
FIG. 10C illustrates the effects of the novel retinamides of the present invention on the expression of proteins modulated by AR and Mnk/eIF4E signaling.
Figure 11:
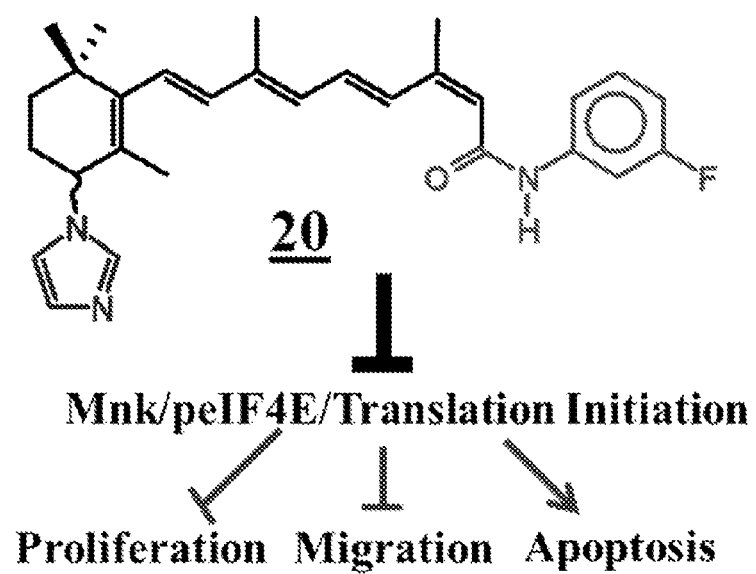
FIG. 11 is a schematic representation illustrating an action of a novel retinamide of the present invention to induce Mnk 1/2 degradation to suppress phosphorylation of eukaryotic initiation factor 4F (eIF4E), which can in turn inhibit proliferation and migration of cancer calls, and induce apoptosis in cancer cells.

Molecular Analysis of Tumors:

To assess their in vivo mode of action, we evaluated the effects of Compound 20 on fAR, AR-V7, Mnk-1, peIF4E and their downstream targets. Tumors from mice treated with Compound 20 showed depletion of fAR, AR-V7, Mnk1/2, peIF4E, cyclin D1 and anti-apoptotic Bcl-2 with concomitant up-regulation of pro-apoptotic proteins, Bad (FIG. 10C).

Example 5: Chemistry

General: All the materials listed below were of research grade or spectrophotometric grade in the highest purity commercially available from Sigma-Aldrich. Column chromatography was performed on silica (230-400 mesh, 60 Å) from Silicycle. Silica gel plates (Merck F254) were used for thin layer chromatography (TLC) and were developed with mixtures of ethyl acetate (EtOAc)/Petroleum ether or $CH_2Cl_2$/methanol (MeOH) unless otherwise specified and were visualized with 254 and 365 nm light and $I_2$ or $Br_2$ vapor. Petroleum ether refers to light petroleum, bp 40-60° C. $^1$H and $^{13}$C NMR spectra were recorded in $CDCl_3$ or DMSO-$d_6$ using a Brüker 400 MHz NMR instrument and chemical shifts are reported in ppm on the δ scale relative to tetramethylsilane. High resolution mass spectra were obtained on Bruker 12 T APEX-Qe FTICR-MS instrument by positive ion ESI mode by Susan A. Hatcher, Facility Director, College of Sciences Major Instrumentation Cluster, Old Dominion University, Norfolk, Va. Melting points (mp) were determined with Fischer Johns melting point apparatus uncorrected. Purities of the compounds were determined by Waters UPLC BEH C18 1.7 μl, 2.1×50 mm column using a solvent gradient system of ammonium acetate buffer/acetonitrile/methanol (100→0, 0→100 and 0→10 respectively) over a period of 10 min. The purities of all final compounds were determined to be at least 95% pure by a combination of UPLC, NMR and HRMS.

Synthesis of (2Z,4E,6E,8E)-methyl 3,7-dimethyl-9-(2,6,6-trimethylcyclohex-1-en-1-yl)nona-2,4,6,8-tetraenoate (Compound 11)

In a 250 mL round bottomed flask (RBF) equipped with a magnetic stirrer, 13-cis-retionoic acid (Compound 10) (5 g, 16.64 mmol) was dissolved in methanol (30 mL) and benzene (100 mL). While stirring, trimethylsilyldiazomethane solution 2.0M in hexanes (3.730 g, 32.68 mmol) was added drop-wise very slowly and reaction was monitored by the gas evolution on the oil bubbler. The reaction mixture was concentrated to give an oily yellow crude product. Purification by flash column chromatography [FCC; petroleum ether/EtOAc (9:1)] afforded Compound 11 as a yellow solid. Yield: 4.32 g (83%); mp: 38-40° C.; $^1$H NMR (400 MHz, CDCl$_3$) δ 7.77 (d, J=15.3 Hz, 1H), 6.99 (dd, J=15.3, 11.5 Hz, 1H), 6.32-6.21 (m, 2H), 6.15 (d, J=16.1 Hz, 1H), 5.64 (s, 1H), 3.70 (s, 3H), 2.07 (s, 3H), 2.03 (t, J=6.2 Hz, 2H), 1.99 (s, 3H), 1.71 (s, 3H), 1.65-1.54 (m, 2H), 1.47 (dd, J=7.7, 3.9 Hz, 2H), 1.03 (s, 6H); $^{13}$C NMR (100 MHz, CDCl$_3$) δ 166.8, 151.3, 139.8, 137.6, 137.4, 132.2, 130.3, 130.0, 129.2, 128.5, 128.3, 116.0, 77.3, 77.0, 76.7, 50.9, 39.6, 34.2, 33.1, 28.9, 21.7, 20.9, 19.2, 12.8.

Synthesis of (2Z,4E,6E,8E)-methyl 3,7-dimethyl-9-(2,6,6-trimethyl-3-oxocyclohex-1-en-1-yl)nona-2,4,6,8-tetraenoate (Compound 12)

In a 500 mL volumetric flask, Compound 11 (4.00 g, 12.7 mmol), MnO$_2$ (100 g, 1150 mmol) were added into 100 mL of dichloromethane. The mixture was allowed to stir on an Innova 2000 platform shaker at 200 rpm for 12 h. Filtration was done through a pad of celite and the organic reaction mixture concentrated to give thick yellow oil. This was adsorbed on silica (50 g) and packed on a column where elution was done gravity with a solvent system of [petroleum ether/EtOAc (9:1)] to yield Compound 12 as a yellow solid. Yield: 2.80 g (68%); mp: 83-85° C.; $^1$H NMR (400 MHz, CDCl$_3$) δ 7.85 (d, J=15.4 Hz, 1H), 6.96 (dd, J=15.3, 11.4 Hz, 1H), 6.35 (dd, J=12.5, 7.6 Hz, 3H), 5.70 (s, 1H), 4.12 (q, J=7.1 Hz, 2H), 3.71 (s, 3H), 2.51 (t, J=6.8 Hz, 2H), 2.08 (s, 3H), 2.02 (s, 3H), 1.86 (s, 3H), 1.26 (t, 2H), 1.19 (s, 6H). $^{13}$C NMR (100 MHz, CDCl$_3$) δ 199., 166.6, 160.7, 150.7, 140.6, 138.1, 133.6, 131.4, 131.2, 130.1, 125.8, 117.2, 51.0, 37.4, 35.7, 34.2, 27.6, 21.0, 13.7.

Synthesis of (2Z,4E,6E,8E)-methyl-9-(3-hydroxy-2,6,6-trimethylcyclohex-1-en-1-yl)-3,7-dimethylnona-2,4,6,8-tetraenoate (13)

In a 25 mL round bottom flask, Compound 12 (2.50 g, 7.61 mmol) was dissolved in methanol (20 mL) and crystalline sodium borohydride (0.45 g, 11.9 mmol) was added slowly and left to stir at room temperature for 1 h where TLC analysis shows exhaustion of the starting material. Reaction mixture was diluted with water (25 mL), extraction done with CH$_2$Cl$_2$ (2×20 mL). Organic portions were mixed and concentrated to give a thick brownish oil. This was adsorbed on silica and packed on a column where elution was done via gravity using a solvent system of [petroleum ether/EtOAc (8:2)] to yield Compound 13 as a yellow oil. Yield: 2.01 g (80%); $^1$H NMR (400 MHz, CDCl$_3$) δ 7.79 (d, J=15.3 Hz, 1H), 7.03-6.92 (m, 1H), 6.27 (d, J=11.4 Hz, 1H), 6.19 (d, J=6.6 Hz, 2H), 5.66 (s, 1H), 4.01 (s, 1H), 3.71 (s, 3H), 2.07 (s, 3H), 1.99 (s, 3H), 1.90 (ddd, J=11.5, 6.9, 3.1 Hz, 1H), 1.84 (s, 3H), 1.76-1.57 (m, 2H), 1.43 (ddd, J=13.2, 7.3, 3.0 Hz, 1H), 1.05 (s, 3H), 1.02 (s, 3H). $^{13}$C NMR (100 MHz, CDCl$_3$) δ 166.7, 151.1, 141.6, 139.2, 138.4, 132.0, 131.1, 130.2, 129.8, 127.5, 116.4, 70.2, 50.9, 34.8, 34.5, 29.0, 27.5, 20.9, 18.6, 12.8.

Synthesis of (2Z,4E,6E,8E)-methyl-9-(3-(1H-imidazol-1-yl)-2,6,6-trimethylcyclohex-1-en-1-yl)-3,7-dimethylnona-2,4,6,8-tetraenoate (Compound 14)

In a 25 mL round bottom flask Compound 13, (1.90 g, 5.75 mmol) was dissolved in acetonitrile (25 mL) followed by 1,1'-Carbonyldiimidazole (CDI) (1.21 mg, 7.47 mmol). On adding CDI, reaction mixture was seen to turn from yellow to dark red with evolution of gas. After 1 hr, TLC analysis showed exhaustion of starting material and the reaction mixture was therefore concentrated. Water (20 mL) was added and extraction was effected using with CH$_2$Cl$_2$ (3×20 mL). The combined organic portion was concentrated, adsorbed on silica and loaded on a column where elution was done via gravity with a solvent system of [methanol/CH$_2$Cl$_2$ (0.5:9.5)] to yield Compound 14 as a red viscous oil. Yield: 1.50 g 69%; $^1$H NMR (400 MHz, CDCl$_3$) δ 7.80 (d, J=15.4 Hz, 1H), 7.50 (s, 1H), 7.07 (s, 1H), 7.00-6.87 (m, 2H), 6.33-6.17 (m, 3H), 5.67 (s, 1H), 4.54 (t, J=4.8 Hz, 1H), 3.71 (s, 3H), 2.08 (s, 3H), 2.01 (s, 3H), 1.82 (dt, J=35.3, 18.6 Hz, 2H), 1.61 (d, J=10.8 Hz, 3H), 1.57 (d, J=11.2 Hz, 1H), 1.50 (dd, J=6.8, 3.5 Hz, 1H), 1.17-1.04 (m, 6H). $^{13}$C NMR (100 MHz, CDCl$_3$) δ 166.7, 150.9, 144.8, 139.2, 138.6, 136.8, 131.7, 131.7, 130.2, 129.2, 126.5, 125.0, 118.1, 116.7, 77.3, 77.2, 77.0, 76.7, 58.0, 53.4, 51.0, 34.7, 34.6, 29.0, 28.1, 27.8, 20.9, 18.8, 12.8; HRMS (ESI) calcd for C$_{24}$H$_{32}$N$_2$O$_2$Na$^+$, 403.2355, Found: 403.2357.

General Procedure A

Synthesis of (2Z,4E,6E,8E)-9-(3-(1H-imidazol-1-yl)-2,6,6-trimethylcyclohex-1-en-1-yl)-3,7-dimethylnona-2,4,6,8-tetraenoic acid (Compound 15)

In a 25 mL round bottom flask, Compound 14 (1.00 g, 2.62 mmol) was dissolved in methanol/water (9:1) and potassium hydroxide (final reaction concentration of 2M) was added. The reaction mixture was let to stir under reflux for 4 h after which the reaction mixture was concentrated and diluted with water (25 mL). The pH of the resulting solution was adjusted to 7. On adjusting the pH, Compound 15 precipitated out of solution as a yellow solid, filtered and washed with cold ether (2×20 mL). This was used as is without further purification in the subsequent step. Yield: 0.60 g (63%); mp 151-153° C.; $^1$H NMR (400 MHz, CDCl$_3$) δ 12.07 (s, 1H), 7.78-7.61 (m, 2H), 7.17-6.87 (m, 3H), 6.32 (q, J=16.2 Hz, 3H), 5.64 (s, 1H), 4.73 (s, 1H), 2.12-1.94 (m, 6H), 1.84-1.68 (m, 2H), 1.50 (s, 3H), 1.48 (s, 2H), 1.09 (d, J=15.1 Hz, 6H). $^{13}$C NMR (100 MHz, DMSO) δ 167.5, 150.6, 143.9, 139.5, 139.0, 137.3, 132.2, 131.9, 130.3, 128.6, 127.2, 125.8, 118.8, 118.2, 66.8, 35.1, 34.7, 29.1, 28.3, 28.1, 20.9, 18.8, 13.0; HRMS (ESI) calcd for C$_{23}$H$_{30}$N$_2$O$_2$Na$^+$, 389.2199, Found: 389.2202.

General Procedure B

Synthesis of (2Z,4E,6E,8E)-9-(3-(1H-imidazol-1-yl)-2,6,6-trimethylcyclohex-1-en-1-yl)-3,7-dimethyl-N-phenylnona-2,4,6,8-tetraenamide (Compound 16)

To a 25 mL round bottom flask, Compound 15 (0.2 g, 0.546 mmol), aniline (0.056 g, 0.601 mmol), EDC (0.208 g, 1.09 mmol), HOBT (0.147 g, 1.09 mmol) and DIPEA (0.706 g, 5.46 mmol) were dissolved in DMF (3 mL). The reaction mixture was allowed to stir for 12 h, concentrated, diluted with water (50 mL) and extracted using $CH_2Cl_2$ (3×20 mL). The combined organic portions were dried over $Na_2SO_4$, and concentrated to give the crude product as a reddish oil. Purification by gravity chromatography on silica using 10% EtOAc in petroleum ether gave Compound 16 as a yellow powder. Yield: 0.16 g (64%); mp: 166-168° C.; $^1$H NMR (400 MHz, $CDCl_3$) δ 7.93 (d, J=15.5 Hz, 1H), 7.52 (d, J=16.1 Hz, 3H), 7.33 (t, J=7.7 Hz, 2H), 7.26 (s, 3H), 7.21 (s, 1H), 7.14-7.06 (m, 2H), 6.94 (dd, J=15.3, 11.3 Hz, 2H), 6.31 (d, J=11.5 Hz, 1H), 6.21 (q, J=16.0 Hz, 2H), 5.70 (s, 1H), 4.54 (s, 1H), 2.09 (s, 3H), 2.01 (s, 3H), 1.92 (s, 1H), 1.85 (s, 1H), 1.66 (s, 3H), 1.57 (d, J=18.1 Hz, 4H), 1.50 (s, 1H), 1.37-1.26 (m, 1H), 1.17-1.02 (m, 6H). $^{13}$C NMR (100 MHz, $CDCl_3$) δ 164.6, 154.1, 146.9, 145.2, 139.5, 137.4, 136.5, 132.3, 131.1, 130.4, 130.2, 128.4, 125.7, 124.5, 121.7, 120.9, 118.5, 115.7, 53.4, 36.5, 31.4, 29.0, 27.7, 24.9, 20.8, 18.8, 12.7; HRMS (ESI) calcd for $C_{29}H_{35}N_3ONa^+$, 464.2672. Found: 464.2674.

Synthesis of (2Z,4E,6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide (Compound 17)

Compound 17 was synthesized using general procedure B. Yellow powder. Yield: 0.113 g (47%); mp: 111-113° C.; $^1$H NMR (400 MHz, $CDCl_3$) δ 8.22 (s, 1H), 7.53 (s, 1H), 7.42 (d, J=7.9 Hz, 1H), 7.08 (s, 1H), 6.93 (s, 1H), 6.85 (dd, J=21.5, 10.1 Hz, 3H), 6.27-6.08 (m, 2H), 5.76 (s, 1H), 4.54 (s, 1H), 3.47 (s, 1H), 2.09 (d, J=11.4 Hz, 1H), 2.02 (s, 2H), 1.98 (s, 3H), 1.91 (s, J=22.5 Hz, 5H), 1.85 (d, J=17.8 Hz, 1H), 1.65 (d, J=12.6 Hz, 1H), 1.56 (d, J=15.3 Hz, 3H), 1.50 (d, J=5.6 Hz, 1H), 1.31 (dd, J=26.4, 14.7 Hz, 1H), 1.11 (s, 3H), 1.07 (s, 3H). $^{13}$C NMR (100 MHz, $CDCl_3$) δ 164.6, 154.1, 146.9, 145.2, 139.5, 137.4, 136.5, 132.3, 131.1, 130.4, 130.2, 128.4, 125.7, 124.5, 121.7, 120.9, 118.5, 115.7, 53.4, 36.5, 31.4, 29.0, 27.7, 24.9, 20.8, 18.8, 12.7; HRMS (ESI) calcd for $C_{29}H_{35}N_3O_2Na^+$, 480.2621. Found: 480.2624.

Synthesis of (2Z,4E,6E,8E)-9-(3-(1H-imidazol-1-yl)-2,6,6-trimethylcyclohex-1-en-1-yl)-N-(2-hydroxyphenyl)-3,7-dimethylnona-2,4,6,8-tetraenamide (Compound 18)

Compound 18 was synthesized using general procedure B. Yellow powder. Yield: 0.080 g (32%); mp: 136-138° C.; $^1$H NMR (400 MHz, $CDCl_3$) δ 7.93 (d, J=15.6 Hz, 1H), 7.66 (s, 1H), 7.50 (s, 1H), 7.16-6.79 (m, 7H), 6.32 (d, J=11.4 Hz, 1H), 6.23 (d, J=7.3 Hz, 2H), 5.78 (s, 1H), 4.54 (s, 1H), 2.09 (d, J=16.3 Hz, 3H), 2.02 (s, 3H), 1.85 (s, 2H), 1.59 (s, 4H), 1.52 (d, J=15.8 Hz, 2H), 1.11 (d, J=21.1 Hz, 6H). $^{13}$C NMR (100 MHz, $CDCl_3$) δ 165.9, 149.9, 149.0, 144.9, 139.2, 138.8, 136.7, 131.9, 130.2, 129.0, 126.7, 126.5, 126.1, 125.0, 121.8, 120.1, 119.4, 118.3, 58.0, 34.7, 34.6, 29.0, 28.1, 27.8, 21.1, 18.8, 12.9; HRMS (ESI) calcd for $C_{29}H_{35}N_3O_2Na^+$, 480.2621. Found: m/z=480.2626.

Synthesis of (2Z,4E,6E,8E)-9-(3-(1H-imidazol-1-yl)-2,6,6-trimethylcyclohex-1-en-1-yl)-N-(4-fluorophenyl)-3,7-dimethylnona-2,4,6,8-tetraenamide (Compound 19)

Compound 19 was synthesized using general procedure B. Yellow powder. Yield: 0.151 g (63%); mp: 123-125° C.; 1H NMR (400 MHz, CDCl3) δ 8.22 (s, 1H), 7.53 (s, 1H), 7.42 (d, J=7.9 Hz, 1H), 7.08 (s, 1H), 6.93 (s, 1H), 6.75 (dd, J=21.5, 10.1 Hz, 3H), 6.41 (m, 2H), 5.76 (s, 1H), 4.54 (s, 1H), 3.47 (s, 1H), 2.09 (d, J=11.4 Hz, 1H), 2.02 (s, 2H), 1.98 (s, 3H), 1.91 (s, J=22.5 Hz, 5H), 1.85 (d, J=17.8 Hz, 1H), 1.65 (d, J=12.6 Hz, 1H), 1.56 (d, J=15.3 Hz, 3H), 1.50 (d, J=5.6 Hz, 1H), 1.31 (dd, J=26.4, 14.7 Hz, 1H), 1.11 (s, 3H), 1.07 (s, 3H). 13C NMR (100 MHz, CDCl3) δ 164.7, 153.1, 146.8, 145.2, 139.5, 137.4, 135.5, 132.3, 131.0, 130.4, 130.2, 127.4, 125.7, 124.5, 122.7, 120.9, 116.5, 115.7, 53.4, 35.5, 31.4, 29.0, 27.7, 24.9, 20.8, 18.8, 12.7; calcd for $C_{29}H_{34}FN_3ONa^+$, 482.2578. Found: m/z=482.2580.

Synthesis of (2Z,4E,6E,8E)-9-(3-(1H-imidazol-1-yl)-2,6,6-trimethylcyclohex-1-en-1-yl)-N-(3-fluorophenyl)-3,7-dimethylnona-2,4,6,8-tetraenamide (Compound 20)

Compound 20 was synthesized using general procedure B. Yellow powder. Yield: 0.143 g (59%); mp: 119-121° C.; $^1$H NMR (400 MHz, $CDCl_3$) δ 7.92 (d, J=15.4 Hz, 1H), 7.51 (dd, J=33.6, 17.3 Hz, 3H), 7.17 (s, 1H), 7.07 (s, 1H), 7.03-6.88 (m, 2H), 6.78 (s, 1H), 6.34-6.14 (m, 3H), 5.68 (s, 1H), 4.54 (s, 1H), 2.05 (d, J=32.2 Hz, 6H), 1.85 (s, 1H), 1.69 (s, 3H), 1.52 (d, J=17.0 Hz, 2H), 1.29 (s, 1H), 1.10 (d, J=19.9 Hz, 6H)$^{13}$C NMR (100 MHz, $CDCl_3$) δ 164.4, 161.8, 149.0, 144.9, 139.9, 139.2, 138.4, 136.8, 136.2, 131.9, 131.4, 131.0, 130.4, 130.0, 129.9, 129.1, 126.4, 125.0, 119.5, 118.2, 58.0, 34.7, 34.6, 29.03, 28.1, 27.8, 21.0, 18.8, 12.8; HRMS (ESI) calcd for $C_{29}H_{34}FN_3ONa^+$, 482.2578. Found: 482.2580.

Synthesis of (2Z,4E,6E,8E)-9-(3-(1H-imidazol-1-yl)-2,6,6-trimethylcyclohex-1-en-1-yl)-N-benzyl-3,7-dimethylnona-2,4,6,8-tetraenamide (Compound 21)

Compound 21 was synthesized using general procedure B. Yellow powder. Yield: 0.124 g (52%); mp: 79-81° C.; $^1$H NMR (400 MHz, $CDCl_3$) δ 7.89 (d, J=3.3 Hz, 1H), 7.71-7.65 (m, 2H), 7.37 (dd, J=14.1, 6.2 Hz, 1H), 7.34-7.28 (m, 5H), 7.09 (s, 1H), 6.92 (s, 1H), 6.28 (d, J=11.2 Hz, 1H), 6.18 (d, J=5.8 Hz, 1H), 5.79 (s, 1H), 5.58 (s, 1H), 4.58 (s, 1H), 4.49 (d, J=5.7 Hz, 2H), 2.16-2.08 (m, 1H), 2.06-1.97 (m, 6H), 1.82 (dd, J=8.8, 4.2 Hz, 1H), 1.61-1.53 (m, 3H), 1.52-1.47 (m, 2H), 1.15 (d, J=6 Hz, 6H). $^{13}$C NMR (100 MHz, $CDCl_3$) δ 166.2, 146.8, 146.0, 139.5, 138.4, 137.5, 136.1, 132.3, 130., 130.38, 128.7, 127.8, 127.4, 126.0, 125.6, 124.1, 123.8, 120., 119.0, 110.1, 58.7, 43.5, 34.7, 34.3, 29.0, 28.0, 27.7, 20.8, 18.8, 12; calcd for $C_{30}H_{37}N_3ONa^+$, 478.2828. Found: 478.2829.

Synthesis of (2Z,4E,6E,8E)-9-(3-(1H-imidazol-1-yl)-2,6,6-trimethylcyclohex-1-en-1-yl)-N-(4-hydroxybenzyl)-3,7-dimethylnona-2,4,6,8-tetraenamide (Compound 22)

Compound 22 was synthesized using general procedure B. Yellow powder. Yield: 0.161 g (62%); mp: 139-141° C.; $^1$H NMR (400 MHz, $CDCl_3$) δ 7.66 (d, J=15.3 Hz, 1H), 7.55 (s, 1H), 7.14 (d, J=7.5 Hz, 2H), 7.09 (s, 1H), 6.95 (s, 1H), 6.87-6.77 (m, 3H), 6.17 (dd, J=18.0, 10.5 Hz, 3H), 5.94 (s, 1H), 5.62 (s, 1H), 4.54 (s, 1H), 4.48-4.29 (m, 2H), 2.14 (s, 1H), 1.97 (t, J=6 Hz, 6H), 1.85 (s, 2H), 1.60 (s, 3H), 1.53 (d, J=12.8 Hz, 2H), 1.10 (s, 6H). $^{13}$C NMR (100 MHz, $CDCl_3$) δ 166.4, 156.9, 145.6, 145.2, 140.0, 137.2, 136.2, 132.5, 131.0, 129.8, 129.3, 128.9, 128.2, 125.5, 124.4, 121.1, 118.8, 115.8, 58.5, 43.2, 34.6, 34.4, 29.0, 28.0, 27.8, 20.5, 19.1, 12.7; HRMS (ESI) calcd for $C_{30}H_{37}N_3O_2Na^+$, 494.2777. Found: 494.2780.

Synthesis of (2Z,4E,6E,8E)-9-(3-(1H-imidazol-1-yl)-2,6,6-trimethylcyclohex-1-en-1-yl)-N-(4-fluorobenzyl)-3,7-dimethylnona-2,4,6,8-tetraenamide (Compound 23)

Compound 23 was synthesized using general procedure B. Yellow powder. Yield: 0.119 g (47%); mp: 93-95° C.; $^1$H NMR (400 MHz, CDCl$_3$) δ 7.95-7.84 (m, 2H), 7.74-7.65 (m, 1H), 7.12 (s, 1H), 6.93 (ddd, J=26.9, 16.4, 10.0 Hz, 4H), 6.22 (dt, J=22.8, 13.7 Hz, 4H), 5.86 (s, 1H), 5.59 (s, 1H), 4.58 (d, J=4.6 Hz, 1H), 4.45 (d, J=5.8 Hz, 2H), 2.18-2.07 (m, 1H), 2.05-1.96 (m, 6H), 1.83 (dd, J=9.1, 4.8 Hz, 1H), 1.58 (s, 3H), 1.53-1.49 (m, 2H), 1.15-1.06 (m, 6H). $^{13}$C NMR (100 MHz, CDCl$_3$) δ 166.2, 164.8, 163.4, 150.6, 147.0, 146.7, 139.5, 137.6, 134.3, 132.2, 130.9, 130.4, 129.5, 129.4, 125.6, 123.9, 123.9, 122.0, 115.6, 115.4, 110.1, 58.8, 42.7, 34.7, 34.2, 29.0, 28.0, 27.7, 20.8, 18.8, 12.8; calcd for $C_{30}H_{36}FN_3ONa^+$, 496.2734. Found: 496.2735.

Synthesis of (2Z,4E,6E,8E)-9-(3-(1H-imidazol-1-yl)-2,6,6-trimethylcyclohex-1-en-1-yl)-N-(3-fluorobenzyl)-3,7-dimethylnona-2,4,6,8-tetraenamide (Compound 24)

Compound 24 was synthesized using general procedure B. Yellow powder. Yield: 0.137 g (54%); mp: 96-98° C.; $^1$H NMR (400 MHz, CDCl$_3$) δ 7.93-7.86 (m, 1H), 7.69 (s, 1H), 7.15-6.84 (m, 7H), 6.28 (d, J=11.4 Hz, 1H), 6.26-6.12 (m, 2H), 5.91 (s, 1H), 5.60 (s, 1H), 4.58 (d, J=4.5 Hz, 1H), 4.49 (d, J=5.9 Hz, 2H), 2.19-2.07 (m, 1H), 2.02 (d, J=18.1 Hz, 6H), 1.83 (dd, J=9.5, 5.5 Hz, 1H), 1.58 (s, 3H), 1.50 (dd, J=15.4, 9.4 Hz, 2H), 1.16-1.05 (m, 6H). $^{13}$C NMR (100 MHz, CDCl$_3$) δ 166.2, 164.2, 161.7, 147.2, 145.9, 141.2, 139.5, 137.7, 132.2, 130.9, 130.5, 130.1, 125.7, 124.0, 123.2, 119.7, 114.6, 110.0, 58.6, 42.8, 34.7, 34.3, 29.0, 27.9, 27.7, 20.8, 18.8, 12.8; calcd. for $C_{30}H_{36}FN_3ONa^+$, 496.2734. Found: 496.2735.

Synthesis of (2Z,4E,6E,8E)-9-(3-(1H-imidazol-1-yl)-2,6,6-trimethylcyclohex-1-en-1-yl)-N-(4-hydroxyphenethyl)-3,7-dimethylnona-2,4,6,8-tetraenamide (Compound 25)

Compound 25 was synthesized using general procedure B. Yellow powder. Yield: 0.161 g (60%); mp: 126-128° C.; $^1$H NMR (400 MHz, CDCl$_3$) δ 7.58 (d, J=15.3 Hz, 1H), 7.10 (s, 1H), 7.04 (d, J=8.4 Hz, 2H), 6.94 (s, 1H), 6.85-6.80 (m, 3H), 6.23-6.16 (m, 4H), 5.60 (t, J=5.7 Hz, 1H), 5.54 (s, 1H), 4.55 (t, J=4.7 Hz, 1H), 3.57-3.51 (m, 2H), 2.76 (t, J=6.7 Hz, 2H), 2.17-2.07 (m, 1H), 1.98 (dd, J=9.1, 5.3 Hz, 6H), 1.88-1.77 (m, 2H), 1.60 (s, 3H), 1.51 (dd, J=14.0, 3.9 Hz, 2H), 1.10 (d, J=9.6 Hz, 6H). $^{13}$C NMR (100 MHz, CDCl$_3$) δ 166.7, 155.3, 145.9, 145.4, 139.7, 137.4, 132.2, 130.7, 130.1, 129.7, 125.9, 125.6, 124.0, 124.0, 121.0, 119.0, 115.0, 110.2, 58.6, 40.7, 34.7, 34.3, 29.1, 28.0, 27.6, 20.7, 19.0, 12.7; calcd for $C_{31}H_{39}N_3O_2Na^+$, 508.2934. Found: 508.2935.

Synthesis of (2Z,4E,6E,8E)-methyl 3,7-dimethyl-9-(2,6,6-trimethyl-3-(trifluoromethyl)sulfonyl)oxy)cyclohexa-1,3-dien-1-yl)nona-2,4,6,8-tetraenoate (Compound 26)

In a 50 mL flask equipped with a magnetic stirrer, THF (10 mL) was added and the temperature lowered to −78° C. Sodium bis(trimethylsilyl)amide solution ((1M in THF), 9.2 mL, 9.24 mmol) was added into the chilled THF. On to this, Compound 12 (2.0 g, 6.09 mmol) dissolved in 10 mL THF was added very slowly and let to stir for 45 min at this temperature. During this time, reaction mixture was seen to turn from yellow color to brick red. N-(5-chloro-2-pyridyl) bis trifluoromethanesulfonimide (3.58 g, 9.12 mmol) dissolved in 10 mL THF was added very slowly onto the reaction mixture. Reaction mixture was then let to stir at this temperature for an additional 3 h. Reaction mixture was thereafter poured quickly into an aqueous solution of NaHCO$_3$ and extracted using EtOAc. Purification by flash chromatography on silica using 10% EtOAc in petroleum ether gave Compound 26 as a yellow powder. Yield: 2.03 g (75%); mp: 98-100° C.; $^1$H NMR (400 MHz, CDCl$_3$) δ 7.82 (d, J=15.3 Hz, 1H), 6.97 (dd, J=15.3, 11.4 Hz, 1H), 6.37-6.11 (m, 3H), 5.73 (t, J=4.9 Hz, 1H), 5.68 (s, 1H), 3.71 (d, J=2.7 Hz, 3H), 2.24 (d, J=5.0 Hz, 2H), 2.08 (d, J=1.1 Hz, 3H), 2.01 (s, 3H), 1.90 (s, 3H), 1.06 (s, 6H). $^{13}$C NMR (100 MHz, CDCl$_3$) δ 166.7, 150.8, 147.9, 144.5, 139.1, 138.5, 132.5, 131.6, 130.6, 125.4, 122.0, 120.1, 116.9, 113.8, 51.0, 37.7, 34.5, 26.3, 20.9, 14.4, 12.7; calcd for $C_{22}H_{27}F_3O_5SNa^+$, 483.1423. Found: 483.1422.

General Procedure C

Synthesis of (2Z,4E,6E,8E)-methyl-9-(3'-methoxy-2,4,4-trimethyl-4,5-dihydro-[1,1'-biphenyl]-3-yl)-3,7-dimethylnona-2,4,6,8-tetraenoate (Compound 27)

In a 50 ml flask, CeCO$_3$ (2.11 g, 6.47 mmol) dissolve in 1 mL was added followed by 10 mL of dioxane. The solution was flushed with N$_2$ for 1 h. Compound 19 (1.92 g, 4.31 mmol), 3-methoxyphenylboronic acid (0.787 g, 5.18 mmol) and lastly Pd(Ph$_3$)$_4$ (5% weight of 18) were added onto the flask and the reaction mixture allowed to reflux at 85° C. for 12 h. The reaction mixture was concentrated and brine was added. Extraction was done using EtOAc and the organic extracts were concentrated to give a crude product as a dark yellow oil. Purification by gravity chromatography on silica using 5% EtOAc in petroleum ether gave Compound 27 as a red oil. Yield: 1.60 g (88%); $^1$H NMR (400 MHz, CDCl$_3$) δ 7.80 (d, J=15.3 Hz, 1H), 7.27-7.21 (m, 1H), 6.99 (dd, J=15.3, 11.5 Hz, 1H), 6.84-6.76 (m, 2H), 6.73 (dd, J=2.3, 1.6 Hz, 1H), 6.35 (s, 2H), 6.32 (d, J=11.6 Hz, 1H), 5.76 (t, J=4.7 Hz, 1H), 5.65 (s, 2H), 3.86 (s, 1H), 3.81 (d, J=1.8 Hz, 3H), 3.70 (s, 3H), 2.18 (d, J=4.8 Hz, 2H), 2.07 (d, J=1.0 Hz, 3H), 2.03 (s, 3H), 1.74 (s, 3H), 1.10 (d, J=5.8 Hz, 6H). $^{13}$C NMR (100 MHz, CDCl$_3$) δ 166.7, 159.2, 151.1, 143.6, 141.6, 140.9, 139.5, 137.4, 132.1, 131.2, 129.7, 128.8, 127.7, 127.4, 124.6, 120.9, 116.3, 114.0, 111.9, 55.2, 50.9, 39.6, 34.3, 26.6, 20.9, 18.8, 12.8; calcd for $C_{28}H_{34}O_3Na^+$, 441.2400. Found: 441.24.

Synthesis of (2Z,4E,6E,8E)-methyl-3,7-dimethyl-9-(2,6,6-trimethyl-3-(pyridin-3-yl)cyclohexa-1,3-dien-1-yl)nona-2,4,6,8-tetraenoate (Compound 28)

Compound 28 was synthesized using general procedure C using the respective boronic acid. Yellow powder. Yield: 1.201 g (69%); mp: 77-79° C.; $^1$H NMR (400 MHz, CDCl$_3$) δ 8.54-8.44 (m, 2H), 7.80 (d, J=15.3 Hz, 1H), 7.57-7.45 (m, 1H), 7.27-7.22 (m, 1H), 6.99 (dd, J=15.3, 11.4 Hz, 1H), 6.32 (d, J=10.5 Hz, 1H), 5.79 (t, J=4.8 Hz, 1H), 5.66 (s, 1H), 3.71 (d, J=3.0 Hz, 3H), 2.22 (t, J=5.8 Hz, 2H), 2.08 (d, J=1.0 Hz, 3H), 2.03 (s, 3H), 1.71 (s, 3H), 1.11 (d, J=6.1 Hz, 6H). $^{13}$C NMR (100 MHz, CDCl$_3$) δ 166.7, 151.1, 149.2, 147.8, 141.6, 139.3, 138.4, 137.8, 137.6, 135.6, 132.0, 131.4, 129.9, 126.9, 126.5, 126.3, 122.7, 116.4, 50.9, 39.5, 34.3, 26.7, 26.6, 20.9, 18.8, 12.8; calcd for $C_{26}H_{31}NO_2Na^+$, 412.2247. Found: 412.2247.

Synthesis of (2Z,4E,6E,8E)-methyl-3,7-dimethyl-9-(2,6,6-trimethyl-3-(pyrimidin-5-yl)cyclohexa-1,3-dien-1-yl)nona-2,4,6,8-tetraenoate (Compound 29)

Compound 29 was synthesized using general procedure C using the respective boronic acid. Yellow powder. Yield: 0.896 g (60%); mp: 162-164° C.; $^1H$ NMR (400 MHz, CDCl$_3$) δ 9.13 (s, 1H), 8.61 (d, J=3.9 Hz, 2H), 7.81 (d, J=15.3 Hz, 1H), 6.99 (dd, J=15.3, 11.4 Hz, 1H), 6.33 (t, J=5.6 Hz, 3H), 5.85 (t, J=4.7 Hz, 1H), 5.67 (s, 1H), 3.71 (s, 3H), 2.25 (d, J=4.8 Hz, 2H), 2.08 (d, J=0.8 Hz, 3H), 2.04 (d, J=5.0 Hz, 3H), 1.73 (s, 3H), 1.11 (d, J=5.7 Hz, 6H). $^{13}C$ NMR (100 MHz, CDCl$_3$) δ 166.7, 157.0, 155.8, 151.0, 142.4, 139.0, 138.2, 135.4, 135.2, 131.8, 131.7, 130.1, 128.0, 126.5, 125.2, 116.6, 50.9, 39.4, 34.3, 26.6, 26.6, 20.9, 18.8, 12.8; calcd for $C_{25}H_{30}N_2O_2Na^+$, 413.2199. Found: 413.2199.

Synthesis of (2Z,4E,6E,8E)-9-(3'-methoxy-2,4,4-trimethyl-4,5-dihydro-[1,1'-biphenyl]-3-yl)-3,7-dimethylnona-2,4,6,8-tetraenoic acid (Compound 30)

Compound 30 was synthesized using the general procedure A. Yellow powder. Yield: 0.621 g (62%); mp: 194-196° C.; $^1H$ NMR (400 MHz, CDCl$_3$) δ 7.76 (t, J=14.0 Hz, 1H), 7.22 (t, J=7.9 Hz, 1H), 7.03 (dd, J=15.3, 11.5 Hz, 1H), 6.82-6.75 (m, 2H), 6.73 (d, J=1.7 Hz, 1H), 6.39-6.31 (m, 3H), 5.76 (t, J=4.7 Hz, 1H), 5.68 (s, 1H), 3.81 (d, J=3.0 Hz, 3H), 2.18 (t, J=6.4 Hz, 2H), 2.11 (s, 3H), 2.03 (s, 3H), 1.73 (s, 3H), 1.11 (d, J=7.1 Hz, 6H). $^{13}C$ NMR (100 MHz, CDCl$_3$) δ 166.7, 159.2, 151.1, 143.6, 141.6, 140.9, 139.5, 137.4, 132.1, 131.2, 129.7, 128.8, 127.6, 127.4, 124.6, 120.9, 116.3, 113.9, 111.9, 55.2, 50.9, 39.6, 34.3, 26.7, 26.6, 20.9, 18.8, 12.8; calcd for $C_{27}H_{32}O_3Na^+$, 427.2243. Found: m/z=427.2246.

Synthesis of (2Z,4E,6E,8E)-3,7-dimethyl-9-(2,6,6-trimethyl-3-(pyridin-3-yl)cyclohexa-1,3-dien-1-yl)nona-2,4,6,8-tetraenoic acid (Compound 31)

Compound 31 was synthesized using general procedure A. Orange powder. Yield: 0.584 g (48%); mp: 113-116° C.; $^1H$ NMR (400 MHz, CDCl$_3$) δ 8.54-8.44 (m, 2H), 7.81 (d, J=15.3 Hz, 1H), 7.53 (dt, J=7.8, 1.9 Hz, 1H), 7.31-7.22 (m, 1H), 7.01 (dd, J=15.3, 11.5 Hz, 1H), 6.34 (d, J=9.6 Hz, 3H), 5.78 (t, J=4.7 Hz, 1H), 5.71 (s, 1H), 2.21 (d, J=4.8 Hz, 2H), 2.10 (t, J=3.4 Hz, 3H), 2.04 (d, J=5.0 Hz, 3H), 1.70 (s, 3H), 1.11 (d, J=8.8 Hz, 6H). $^{13}C$ NMR (100 MHz, CDCl$_3$) δ 169.3, 152.5, 148.6, 147.2, 141.7, 139.5, 138.2, 137.8, 136.1, 132.3, 131.5, 129.9, 127.1, 126.6, 126.4, 122.9, 116.3, 77.3, 77.2, 77.0, 76.7, 39.5, 34.3, 26.6, 21.1, 18.8, 12.8; calcd for $C_{25}H_{29}NO_2Na^+$, 398.2090. Found: 398.2090.

Synthesis of (2Z,4E,6E,8E)-3,7-dimethyl-9-(2,6,6-trimethyl-3-(pyrimidin-5-yl)cyclohexa-1,3-dien-1-yl)nona-2,4,6,8-tetraenoic acid (Compound 32)

Compound 32 was synthesized using general procedure A. Yellow powder. Yield: 0.673 g (70%); mp: 111-113° C.; $^1H$ NMR (400 MHz, CDCl$_3$) δ 9.13 (d, J=3.6 Hz, 1H), 8.62 (d, J=5.5 Hz, 2H), 7.80 (d, J=15.3 Hz, 1H), 7.02 (dd, J=15.3, 11.5 Hz, 1H), 6.41-6.29 (m, 3H), 5.85 (t, J=4.7 Hz, 1H), 5.70 (s, 1H), 2.25 (d, J=4.8 Hz, 2H), 2.11 (t, J=3.6 Hz, 3H), 2.04 (d, J=3.8 Hz, 3H), 1.73 (s, 3H), 1.11 (d, J=7.4 Hz, 6H). $^{13}C$ NMR (100 MHz, CDCl$_3$) δ 169.7, 156.8, 155.8, 153.0, 142.4, 139.5, 138.2, 135.5, 135.1, 132.4, 131.7, 130.0, 128.2, 126.7, 125.3, 116.0, 67.1, 39.4, 34.3, 26.6, 21.1, 18.8, 12.8; calcd for $C_{24}H_{28}N_2O_2Na^+$, 399.2042. Found: 399.2043.

Synthesis of (2Z,4E,6E,8E)-N-(4-hydroxybenzyl)-9-(3'-methoxy-2,4,4-trimethyl-4,5-dihydro-[1,1'-biphenyl]-3-yl)-3,7-dimethylnona-2,4,6,8-tetraenamide (Compound 33)

Compound 33 was synthesized using general procedure B as a red oil. Yield: 0.124 g (45%); $^1H$ NMR (400 MHz, CDCl$_3$) δ 7.21-7.14 (m, 2H), 6.83-6.69 (m, 5H), 6.35-6.13 (m, 4H), 5.77-5.52 (m, 4H), 4.92 (d, J=5.7 Hz, 1H), 4.42 (d, J=5.6 Hz, 2H), 3.83 (t, J=7.8 Hz, 3H), 2.18 (t, J=5.3 Hz, 3H), 2.02 (d, J=6.8 Hz, 3H), 1.75 (d, J=11.6 Hz, 3H), 1.10 (dd, J=11.3, 5.9 Hz, 6H). $^{13}C$ NMR (100 MHz, CDCl$_3$) δ 166.5, 159.2, 155.5, 149.1, 147.0, 143.7, 141.6, 141.0, 138.6, 137.6, 135.8, 132.3, 131.4, 130.8, 130.1, 129.3, 128.8, 127.5, 126.9, 124.5, 120.9, 119.5, 115.6, 113.9, 111.9, 55.2, 43.0, 39.5, 36.6, 34.3, 26.6, 20.8, 18.8, 12.8; calcd for $C_{34}H_{39}NO_3Na^+$, 532.2822. Found: 532.2821.

Synthesis of (2Z,4E,6E,8E)-N-(4-hydroxyphenethyl)-9-(3'-methoxy-2,4,4-trimethyl-4,5-dihydro-[1,1'-biphenyl]-3-yl)-3,7-dimethylnona-2,4,6,8-tetraenamide (Compound 34)

Compound 34 was synthesized using general procedure B. Yellow powder. Yield: 0.104 g (40%); mp: 102-105° C.; $^1H$ NMR (400 MHz, CDCl$_3$) δ 7.76 (d, J=15.3 Hz, 1H), 7.23 (t, J=7.9 Hz, 1H), 7.06 (d, J=8.4 Hz, 2H), 6.88 (dd, J=15.3, 11.4 Hz, 1H), 6.80 (dd, J=14.0, 5.4 Hz, 4H), 6.73 (s, 1H), 6.32 (s, 2H), 6.27 (d, J=11.5 Hz, 1H), 5.75 (t, J=4.6 Hz, 1H), 5.46 (d, J=11.5 Hz, 2H), 5.09 (s, 1H), 3.82 (s, 3H), 3.53 (dd, J=12.9, 6.7 Hz, 2H), 2.77 (t, J=6.9 Hz, 2H), 2.18 (t, J=5.1 Hz, 2H), 1.99 (d, J=8.2 Hz, 6H), 1.73 (s, 3H), 1.56 (s, 3H), 1.10 (d, J=4.8 Hz, 6H). $^{13}C$ NMR (100 MHz, CDCl$_3$) δ 200.9, 191.8, 166.6, 159.2, 154.4, 146.5, 143.7, 141.6, 141.0, 138.5, 137.6, 131.4, 130.8, 130.7, 130.1, 129.8, 128.8, 127.4, 126.8, 125.2, 124.5, 120.9, 119.9, 115.5, 113.9, 111.9, 109.3, 55.2, 40.7, 39.5, 34.8, 34.3, 26.6, 20.8, 18.8, 12.7; calcd for $C_{35}H_{41}NO_3Na^+$, 546.2978. Found: 546.2977.

Synthesis of (2Z,4E,6E,8E)-3,7-dimethyl-N-phenyl-9-(2,6,6-trimethyl-3-(pyridin-3-yl)cyclohexa-1,3-dien-1-yl)nona-2,4,6,8-tetraenamide (Compound 35)

Compound 35 was synthesized using general procedure B. Yellow powder. Yield: 0.149 g (62%); mp: 102-104° C.; $^1H$ NMR (400 MHz, CDCl$_3$) δ 8.51 (dd, J=4.8, 1.6 Hz, 1H), 8.47 (d, J=1.6 Hz, 1H), 7.92 (d, J=15.5 Hz, 1H), 7.55 (d, J=7.1 Hz, 2H), 7.53-7.48 (m, 1H), 7.32 (t, J=7.9 Hz, 3H), 7.17 (s, 1H), 7.11 (d, J=7.4 Hz, 1H), 6.96 (dd, J=15.1, 11.4 Hz, 1H), 6.35 (s, 1H), 6.32 (s, 2H), 5.79 (t, J=4.7 Hz, 1H), 5.68 (s, 1H), 2.21 (d, J=4.8 Hz, 2H), 2.09 (s, 3H), 2.02 (s, 3H), 1.71 (d, J=4.6 Hz, 3H), 1.11 (d, J=7.4 Hz, 6H) $^{13}C$ NMR (100 MHz, CDCl$_3$) δ 166.8, 158.2, 149.2, 148.4, 147.8, 141.6, 138.8, 138.4, 137.9, 137.6, 135.6, 131.6, 131.3, 130.2, 128.9, 126.7, 126.3, 122.7, 39.5, 34.3, 26.6, 20.9, 18.8, 12.8; calcd for $C_{31}H_{34}N_2ONa^+$, 473.2563. Found: 473.2563.

Synthesis of (2Z,4E,6E,8E)-N-(4-hydroxybenzyl)-3,7-dimethyl-9-(2,6,6-trimethyl-3-(pyridin-3-yl)cyclohexa-1,3-dien-1-yl)nona-2,4,6,8-tetraenamide (Compound 36)

Compound 36 was synthesized using general procedure B. Yellow powder. Yield: 0.104 g (80%); mp: 124-126° C.; $^1$H NMR (400 MHz, CDCl$_3$) δ 8.52-8.42 (m, 2H), 7.78 (d, J=15.0 Hz, 1H), 7.62-7.49 (m, 2H), 7.16 (d, J=8.5 Hz, 2H), 6.82 (q, J=3.0 Hz, 2H), 6.31-6.22 (m, 3H), 5.79 (dd, J=12.5, 7.8 Hz, 2H), 5.57 (s, 1H), 4.41 (d, J=5.7 Hz, 2H), 2.21 (d, J=4.8 Hz, 2H), 2.01 (d, J=5.1 Hz, 6H), 1.71 (s, 3H), 1.10 (d, J=7.3 Hz, 6H). $^{13}$C NMR (100 MHz, DMSO) δ 165.8, 156.7, 148.9, 148.2, 145.3, 141.8, 138.5, 138.3, 138.2, 137.4, 135.9, 132.2, 131.5, 130.2, 129.1, 126.4, 126.3, 126.3, 123.6, 123.5, 121.5, 118.8, 115.4, 111.0, 41.9, 34.3, 26.8, 20.9, 19.0, 12.9; calcd for $C_{32}H_{36}N_2O_2Na^+$, 503.2669. Found: 503.2667.

Synthesis of (2Z,4E,6E,8E)-N-(4-hydroxyphenethyl)-3,7-dimethyl-9-(2,6,6-trimethyl-3-(pyridin-3-yl)cyclohexa-1,3-dien-1-yl)nona-2,4,6,8-tetraenamide (Compound 37)

Compound 37 was synthesized using general procedure B. Yellow powder. Yield: 0.135 g (51%); mp: 110-112° C.; $^1$H NMR (400 MHz, CDCl$_3$) δ 8.50 (dd, J=4.8, 1.6 Hz, 1H), 8.47 (d, J=1.5 Hz, 1H), 7.76 (d, J=15.3 Hz, 1H), 7.56-7.50 (m, 1H), 7.05 (d, J=8.4 Hz, 2H), 6.87 (dd, J=15.3, 11.5 Hz, 1H), 6.80 (d, J=8.5 Hz, 2H), 6.30 (d, J=3.1 Hz, 2H), 6.27 (d, J=11.3 Hz, 1H), 5.79 (t, J=4.7 Hz, 1H), 5.53 (t, J=5.6 Hz, 1H), 5.49 (s, 1H), 3.53 (dd, J=12.9, 6.8 Hz, 2H), 2.77 (t, J=6.9 Hz, 2H), 2.21 (d, J=4.8 Hz, 2H), 2.00 (s, 6H), 1.71 (s, 3H), 1.09 (s, 6H). $^{13}$C NMR (100 MHz, CDCl$_3$) δ 166.6, 154.8, 148.9, 147.5, 146.2, 141.8, 138.3, 138.2, 138.1, 137.8, 135.8, 131.7, 130.5, 130.4, 129.8, 126.3, 126.3, 126.2, 122.9, 120.1, 115.6, 40.7, 39.4, 34.8, 34.3, 26.6, 20.7, 18.9, 12.7; calcd for $C_{33}H_{38}N_2O_2Na^+$, 517.2803. Found: 517.2824.

Synthesis of (2Z,4E,6E,8E)-3,7-dimethyl-N-phenyl-9-(2,6,6-trimethyl-3-(pyrimidin-5-yl)cyclohexa-1,3-dien-1-yl)nona-2,4,6,8-tetraenamide (Compound 38)

Compound 38 was synthesized using general procedure B. Yellow powder. Yield: 0.116 g (48%); mp: 105-107° C.; $^1$H NMR (400 MHz, CDCl$_3$) δ 9.12 (s, 1H), 8.61 (d, J=6.1 Hz, 2H), 7.94 (d, J=15.2 Hz, 1H), 7.54 (s, 2H), 7.32 (t, J=7.9 Hz, 2H), 7.12 (dd, J=18.8, 11.4 Hz, 2H), 6.96 (dd, J=15.4, 11.5 Hz, 1H), 6.37-6.27 (m, 2H), 5.84 (t, J=4.5 Hz, 1H), 5.69 (s, 1H), 2.24 (d, J=4.7 Hz, 2H), 2.10 (s, 3H), 2.01 (d, J=11.4 Hz, 3H), 1.72 (s, 3H), 1.11 (d, J=6.6 Hz, 6H). $^{13}$C NMR (100 MHz, CDCl$_3$) δ 166.3, 156.9, 156.8, 155.8, 155.3, 146.6, 142.7, 142.6, 138.6, 138.3, 138.1, 137.9, 135.5, 135.2, 132.1, 130.7, 130.5, 129.4, 127.9, 125.9, 125.1, 120.0, 115.5, 39.4, 34.3, 26.5, 20.7, 18.9, 12.7; calcd for $C_{30}H_{33}N_3ONa^+$, 474.2515. Found: 474.2515.

Synthesis of (2Z,4E,6E,8E)-N-(4-hydroxybenzyl)-3,7-dimethyl-9-(2,6,6-trimethyl-3-(pyrimidin-5-yl)cyclohexa-1,3-dien-1-yl)nona-2,4,6,8-tetraenamide (Compound 39)

Compound 39 was synthesized using general procedure B. Yellow powder. Yield: 0.154 g (60%); mp: 145-147° C.; $^1$H NMR (400 MHz, CDCl$_3$) δ 9.13 (s, 1H), 8.61 (d, J=6.6 Hz, 2H), 7.84 (d, J=15.3 Hz, 1H), 7.17 (d, J=8.3 Hz, 2H), 6.87 (d, J=15.3 Hz, 1H), 6.80 (d, J=8.4 Hz, 2H), 6.28 (d, J=5.2 Hz, 2H), 5.85 (t, J=4.6 Hz, 1H), 5.70 (d, J=11.4 Hz, 1H), 5.57 (s, 1H), 4.41 (d, J=5.6 Hz, 2H), 2.24 (d, J=4.8 Hz, 2H), 2.02 (d, J=7.0 Hz, 6H), 1.72 (s, 3H), 1.10 (d, J=5.7 Hz, 6H). $^{13}$C NMR (100 MHz, CDCl$_3$) δ 166.3, 156.9, 156.8, 155.8, 155.3, 146.6, 142.7, 142.6, 138.6, 138.3, 138.1, 137.9, 135.5, 135.2, 132.1, 130.7, 130.5, 129.4, 127.9, 125.9, 125.1, 120.0, 115.5, 43.0, 39.4, 34.3, 26.5, 20.7, 18.9, 12.7; calcd for $C_{31}H_{35}N_3O_2Na^+$, 504.2621. Found: 504.2620.

Synthesis of (2Z,4E,6E,8E)-N-(4-hydroxyphenethyl)-3,7-dimethyl-9-(2,6,6-trimethyl-3-(pyrimidin-5-yl)cyclohexa-1,3-dien-1-yl)nona-2,4,6,8-tetraenamide (Compound 40)

Compound 40 was synthesized using general procedure B. Yellow powder. Yield: 0.161 g (61%); mp: 115-117° C.; $^1$H NMR (400 MHz, CDCl$_3$) δ 9.12 (s, 1H), 8.61 (d, J=3.5 Hz, 2H), 7.77 (d, J=15.3 Hz, 1H), 7.05 (d, J=8.3 Hz, 2H), 6.79 (d, J=8.3 Hz, 2H), 6.32-6.21 (m, 2H), 5.84 (t, J=4.6 Hz, 1H), 5.55 (t, J=5.7 Hz, 1H), 5.50 (s, 1H), 3.53 (dd, J=12.9, 6.7 Hz, 2H), 2.77 (t, J=6.9 Hz, 2H), 2.24 (d, J=4.8 Hz, 2H), 1.99 (d, J=7.6 Hz, 6H), 1.74 (d, J=10.0 Hz, 3H), 1.13-1.02 (m, 6H). $^{13}$C NMR (100 MHz, CDCl$_3$) δ 166.6, 156.8, 155.8, 154.7, 146.3, 142.6, 138.5, 138.0, 135.5, 135.2, 132.0, 130.6, 130.5, 130.4, 129.8, 128.0, 125.9, 125.0, 120.2, 115.6, 40.7, 39.4, 34.8, 34.3, 26.6, 20.7, 18.8, 12.7; calcd for $C_{32}H_{37}N_3O_2Na^+$, 518.2777. Found: 518.2778.

The inventors have shown for the first time that high anti-cancer activities can be retained in C-4 heteroaryl retinamides based on the sparse 13-cis retinoic acid scaffold. The inventors describe a series of novel C-4 heteroaryl 13-cis retinamides that degrade Mnk 1 and 2 with concomitant suppression of oncogenic eIF4E phosphorylation in a variety of human breast and prostate cancer cell lines. In addition, the compounds modulate activities of full-length and splice variant androgen receptors (fAR and AR-V7) via AR antagonism and AR degradation in prostate cancer cells. Lead compounds, including Compounds 16, 20 and 22, were identified. Of these compounds, Compounds 20 and 22 exhibited equipotent and exquisite suppression of the growth of aggressive human triple negative breast cancer MDA-MB-231 tumor xenografts. Compound 20 also proved to be very effective at inhibiting the growth of castration-resistant CWR22Rv1 human prostate tumor xenografts. These impressive in vitro and in vivo anti-breast and anti-prostate cancers activities make Compounds 20 and 22 strong candidates for further development as potential new drugs for the treatments of breast and prostate cancers in humans. In addition, given the implication of Mnk1/2-eIFE axis in the initiation and progressions of all types of solid tumors[24] and hematologic cancers,[25] these and related retinamides warrant evaluation in other types of cancers.

Associated Content
Supporting Information:
HPLC chromatograms and high resolution mass spectral data for Compounds 16-20 and 33-40. This material is available free of charge via the Internet at http://pubs.acs.org.

Abbreviations Used

AML, acute myeloid leukemia; AR, Androgen Receptor; AR-V7, type of slice varant AR; ATRA, all-trans retinoic acid; BC, breast cancer; eIF4E, eukaryotic translation initiation factor 4E; MAPK, mitogen activated protein kinase;

fAR, full-length AR; Mnks, MAPK-interacting kinases; $GI_{50}$, concentration of agent/compound needed to inhibit cell growth by 50%; MNKDAs, Mnk degrading agents; peIF4E, phosphorylated eukaryotic translation initiation factor 4E; NR, novel retinamides; PC, prostate cancer; TLC, thin layer chromatography; TNBC, triple negative breast cancer; 4-HPR, 4-hydroxyphenyl retinamide, 13-CRA, 13-cis-retinoic acid.

REFERENCES 1. (a) Avdulov, S.; Li, S.; Michalek, V.; Burrichter, D.; Peterson, M.; Perlman, D. M.; Manivel, J. C.; Sonenberg, N.; Yee, D.; Bitterman, P. B.; Polunovsky, V. A., Activation of translation complex eIF4F is essential for the genesis and maintenance of the malignant phenotype in human mammary epithelial cells. *Cancer cell* 2004, 5 (6), 553-63; (b) Gebauer, F.; Hentze, M. W., Molecular mechanisms of translational control. *Nature reviews. Molecular cell biology* 2004, 5 (10), 827-35; (c) Sonenberg, N.; Hinnebusch, A. G., Regulation of translation initiation in eukaryotes: mechanisms and biological targets. *Cell* 2009, 136 (4), 731-45.
2. (a) Nasr, Z.; Robert, F.; Porco, J. A., Jr.; Muller, W. J.; Pelletier, J., eIF4F suppression in breast cancer affects maintenance and progression. *Oncogene* 2013, 32 (7), 861-71; (b) Robichaud, N.; Del Rincon, S. V.; Huor, B.; Alain, T.; Petruccelli, L. A.; Hearnden, J.; Goncalves, C.; Grotegut, S.; Spruck, C. H.; Furic, L.; Larsson, O.; Muller, W. J.; Miller, W. H.; Sonenberg, N., Phosphorylation of eIF4E promotes EMT and metastasis via translational control of SNAIL and MMP-3. *Oncogene* 2014; (c) Wendel, H. G.; Silva, R. L.; Malina, A.; Mills, J. R.; Zhu, H.; Ueda, T.; Watanabe-Fukunaga, R.; Fukunaga, R.; Teruya-Feldstein, J.; Pelletier, J.; Lowe, S. W., Dissecting eIF4E action in tumorigenesis. *Genes & development* 2007, 21 (24), 3232-7.
3. (a) Aktas, B. H.; Qiao, Y.; Ozdelen, E.; Schubert, R.; Sevinc, S.; Harbinski, F.; Grubissich, L.; Singer, S.; Halperin, J. A., Small-Molecule targeting of translation initiation for cancer therapy. *Oncotarget* 2013, 4 (10), 1606-17; (b) Bitterman, P. B.; Polunovsky, V. A., Attacking a nexus of the oncogenic circuitry by reversing aberrant eIF4F-mediated translation. *Molecular cancer therapeutics* 2012, 11 (5), 1051-61; (c) Bitterman, P. B.; Polunovsky, V. A., Translational control of cell fate: from integration of environmental signals to breaching anticancer defense. *Cell cycle* 2012, 11 (6), 1097-107; (d) Carroll, M.; Borden, K. L., The oncogene eIF4E: using biochemical insights to target cancer. *Journal of Interferon & Cytokine Research: The Official Journal of the International Society for Interferon and Cytokine Research* 2013, 33 (5), 227-38; (e) Diab, S.; Kumarasiri, M.; Yu, M.; Teo, T.; Proud, C.; Milne, R.; Wang, S., MAP kinase-interacting kinases-emerging targets against cancer. *Chemistry & Biology* 2014, 21 (4), 441-52.
4. Graff, J. R.; Konicek, B. W.; Vincent, T. M.; Lynch, R. L.; Monteith, D.; Weir, S. N.; Schwier, P.; Capen, A.; Goode, R. L.; Dowless, M. S.; Chen, Y.; Zhang, H.; Sissons, S.; Cox, K.; McNulty, A. M.; Parsons, S. H.; Wang, T.; Sams, L.; Geeganage, S.; Douglass, L. E.; Neubauer, B. L.; Dean, N. M.; Blanchard, K.; Shou, J.; Stancato, L. F.; Carter, J. H.; Marcusson, E. G., Therapeutic suppression of translation initiation factor eIF4E expression reduces tumor growth without toxicity. *J Clin Invest* 2007, 117 (9), 2638-48.
5. Hong, D. S.; Kurzrock, R.; Oh, Y.; Wheler, J.; Naing, A.; Brail, L.; Callies, S.; Andre, V.; Kadam, S. K.; Nasir, A.; Holzer, T. R.; Meric-Bernstam, F.; Fishman, M.; Simon, G., A phase 1 dose escalation, pharmacokinetic, and pharmacodynamic evaluation of eIF-4E antisense oligonucleotide LY2275796 in patients with advanced cancer. *Clin Cancer Res* 2011, 17 (20), 6582-91.
6. Konicek, B. W.; Stephens, J. R.; McNulty, A. M.; Robichaud, N.; Peery, R. B.; Dumstorf, C. A.; Dowless, M. S.; Iversen, P. W.; Parsons, S.; Ellis, K. E.; McCann, D. J.; Pelletier, J.; Furic, L.; Yingling, J. M.; Stancato, L. F.; Sonenberg, N.; Graff, J. R., Therapeutic inhibition of MAP kinase interacting kinase blocks eukaryotic initiation factor 4E phosphorylation and suppresses outgrowth of experimental lung metastases. *Cancer research* 2011, 71 (5), 1849-57.
7. Altman, J. K.; Szilard, A.; Konicek, B. W.; Iversen, P. W.; Kroczynska, B.; Glaser, H.; Sassano, A.; Vakana, E.; Graff, J. R.; Platanias, L. C., Inhibition of Mnk kinase activity by cercosporamide and suppressive effects on acute myeloid leukemia precursors. *Blood* 2013, 121 (18), 3675-81.
8. (a) Ramalingam, S.; Gediya, L.; Kwegyir-Afful, A. K.; Ramamurthy, V. P.; Purushottamachar, P.; Mbatia, H.; Njar, V. C., First MNKs degrading agents block phosphorylation of eIF4E, induce apoptosis, inhibit cell growth, migration and invasion in triple negative and Her2-over-expressing breast cancer cell lines. *Oncotarget* 2014, 5 (2), 530-43; (b) Ramamurthy, V. P., Ramalingam, S., Gediya, L. K., Kwegyir-Afful, A. K., Njar, V. C. O., Simultaneous targeting of AR and MNK signaling pathways by novel retinamides induce profound anti-tumor and anti-invasive activities in human prostate cancer cell lines. *Oncotarget* 2014, in press.
9. Hou, J.; Lam, F.; Proud, C.; Wang, S., Targeting Mnks for cancer therapy. *Oncotarget* 2012, 3 (2), 118-31.
10. Bain, J.; Plater, L.; Elliott, M.; Shpiro, N.; Hastie, C. J.; McLauchlan, H.; Klevernic, I.; Arthur, J. S.; Alessi, D. R.; Cohen, P., The selectivity of protein kinase inhibitors: a further update. *The Biochemical journal* 2007, 408 (3), 297-315.
11. Teo, T., Lam, F., Yu, M., Yang, Y., Basnet, S., Albrecht, H., Sykes, M., Wag, S., Pharmacologic inhibition of Mnks in acute myeloid leukemia. *FEBS Journal* 2014, In press.
12. (a) Njar, V. C.; Gediya, L.; Purushottamachar, P.; Chopra, P.; Vasaitis, T. S.; Khandelwal, A.; Mehta, J.; Huynh, C.; Belosay, A.; Patel, J., Retinoic acid metabolism blocking agents (RAMBAs) for treatment of cancer and dermatological diseases. *Bioorganic & medicinal chemistry* 2006, 14 (13), 4323-40; (b) Patel, J. B.; Huynh, C. K.; Handratta, V. D.; Gediya, L. K.; Brodie, A. M.; Goloubeva, O. G.; Clement, O. O.; Nanne, I. P.; Soprano, D. R.; Njar, V. C., Novel retinoic acid metabolism blocking agents endowed with multiple biological activities are efficient growth inhibitors of human breast and prostate cancer cells in vitro and a human breast tumor xenograft in nude mice. *Journal of medicinal chemistry* 2004, 47 (27), 6716-29.
13. (a) Bissantz, C.; Kuhn, B.; Stahl, M., A medicinal chemist's guide to molecular interactions. *Journal of medicinal chemistry* 2010, 53 (14), 5061-84; (b) Purushottamachar, P.; Godbole, A. M.; Gediya, L. K.; Martin, M. S.; Vasaitis, T. S.; Kwegyir-Afful, A. K.; Ramalingam, S.; Ates-Alagoz, Z.; Njar, V. C., Systematic structure modifications of multitarget prostate cancer drug candidate galeterone to produce novel androgen receptor downregulating agents as an approach to treatment of advanced prostate cancer. *Journal of medicinal chemistry* 2013, 56 (12), 4880-98.

14. (a) Clamon, G.; Chabot, G. G.; Valeriote, F.; Davilla, E.; Vogel, C.; Gorowski, E.; Birch, R., Phase I study and pharmacokinetics of weekly high-dose 13-cis-retinoic acid. *Cancer research* 1985, 45 (4), 1874-8; (b) Reynolds, C. P.; Matthay, K. K.; Villablanca, J. G.; Maurer, B. J., Retinoid therapy of high-risk neuroblastoma. *Cancer letters* 2003, 197 (1-2), 185-92; (c) Veal, G. J.; Cole, M.; Errington, J.; Pearson, A. D.; Foot, A. B.; Whyman, G.; Boddy, A. V.; Group, U. P. W., Pharmacokinetics and metabolism of 13-cis-retinoic acid (isotretinoin) in children with high-risk neuroblastoma—a study of the United Kingdom Children's Cancer Study Group. *British journal of cancer* 2007, 96 (3), 424-31.

15. Marin, J.; Capron, C. C.; Idres, N.; Chabot, G. G., Human cytochrome P450s involved in the metabolism of 9-cis- and 13-cis-retinoic acids. *Biochemical pharmacology* 2002, 63 (5), 933-43.

16. (a) Hu, Q.; Negri, M.; Jahn-Hoffmann, K.; Zhuang, Y.; Olgen, S.; Bartels, M.; Muller-Vieira, U.; Lauterbach, T.; Hartmann, R. W., Synthesis, biological evaluation, and molecular modeling studies of methylene imidazole substituted biaryls as inhibitors of human 17alpha-hydroxylase-17,20-lyase (CYP17)—part II: Core rigidification and influence of substituents at the methylene bridge. *Bioorganic & medicinal chemistry* 2008, 16 (16), 7715-27; (b) Mahalingam, P.; Takrouri, K.; Chen, T.; Sahoo, R.; Papadopoulos, E.; Chen, L.; Wagner, G.; Aktas, B. H.; Halperin, J. A.; Chorev, M., Synthesis of rigidified eIF4E/eIF4G inhibitor-1 (4EGI-1) mimetic and their in vitro characterization as inhibitors of protein-protein interaction. *Journal of medicinal chemistry* 2014, 57 (12), 5094-111.

17. (a) Agranat, I.; Caner, H.; Caldwell, J., Putting chirality to work: the strategy of chiral switches. *Nature reviews. Drug discovery* 2002, 1 (10), 753-68; (b) Caner, H.; Groner, E.; Levy, L.; Agranat, I., Trends in the development of chiral drugs. *Drug discovery today* 2004, 9 (3), 105-10.

18. Patel, J. B.; Huynh, C. K.; Handratta, V. D.; Gediya, L. K.; Brodie, A. M. H.; Goloubeva, O. G.; Clement, O. O.; Nanne, I. P.; Soprano, D. R.; Njar, V. C. O., Novel Retinoic Acid Metabolism Blocking Agents Endowed with Multiple Biological Activities Are Efficient Growth Inhibitors of Human Breast and Prostate Cancer Cells in Vitro and a Human Breast Tumor Xenograft in Nude Mice. *Journal of Medicinal Chemistry* 2004, 47 (27), 6716-6729.

19. Johnson, A. T.; Klein, E. S.; Gillett, S. J.; Wang, L.; Song, T. K.; Pino, M. E.; Chandraratna, R. A. S., Synthesis and Characterization of a Highly Potent and Effective Antagonist of Retinoic Acid Receptors. *J. Med. Chem.* 1995, 38 (Copyright (C) 2014 American Chemical Society (ACS). All Rights Reserved.), 4764-7.

20. Zaveri, N.; Jiang, F.; Olsen, C.; Polgar, W.; Toll, L., Novel α3β4 Nicotinic Acetylcholine Receptor-Selective Ligands. Discovery, Structure-Activity Studies, and Pharmacological Evaluation. *J. Med. Chem.* 2010, 53 (Copyright (C) 2014 American Chemical Society (ACS). All Rights Reserved.), 8187-8191.

21. Gediya, L. K.; Khandelwal, A.; Patel, J.; Belosay, A.; Sabnis, G.; Mehta, J.; Purushottamachar, P.; Njar, V. C., Design, synthesis, and evaluation of novel mutual prodrugs (hybrid drugs) of all-trans-retinoic acid and histone deacetylase inhibitors with enhanced anticancer activities in breast and prostate cancer cells in vitro. *Journal of medicinal chemistry* 2008, 51 (13), 3895-904.

22. Lonergan, P. E.; Tindall, D. J., Androgen receptor signaling in prostate cancer development and progression. *Journal of carcinogenesis* 2011, 10, 20.

23. (a) Bissery, M. C.; Chabot, G. G., [History and new development of screening and evaluation methods of anticancer drugs used in vivo and in vitro]. *Bulletin du cancer* 1991, 78 (7), 587-602; (b) Hollingshead, M. G., Antitumor efficacy testing in rodents. *Journal of the National Cancer Institute* 2008, 100 (21), 1500-10.

24. Hsieh, A. C.; Ruggero, D., Targeting eukaryotic translation initiation factor 4E (eIF4E) in cancer. *Clinical cancer research: an official journal of the American Association for Cancer Research* 2010, 16 (20), 4914-20.

25. Hagner, P. R.; Schneider, A.; Gartenhaus, R. B., Targeting the translational machinery as a novel treatment strategy for hematologic malignancies. *Blood* 2010, 115 (11), 2127-35.

26. Kanazawa, S.; Fujiwara, T.; Matsuzaki, S.; Shingaki, K.; Taniguchi, M.; Miyata, S.; Tohyama, M.; Sakai, Y.; Yano, K.; Hosokawa, K.; Kubo, T., bFGF regulates PI3-kinase-Rac1-JNK pathway and promotes fibroblast migration in wound healing. *PloS one* 2010, 5 (8), e12228.

27. Grzmil, M.; Huber, R. M.; Hess, D.; Frank, S.; Hynx, D.; Moncayo, G.; Klein, D.; Merlo, A.; Hemmings, B. A., MNK1 pathway activity maintains protein synthesis in rapalog-treated gliomas. *The Journal of clinical investigation* 2014, 124 (2), 742-54.

The invention claimed is:

1. A process for treatment of breast cancer, prostate cancer, bladder cancer, pancreatic cancer, hepatocellular carcinoma, benign prostatic hyperplasia, Kennedy's disease, or hematologic cancer, comprising administering to a subject in need thereof a pharmaceutical composition comprising as an active ingredient a compound having the following Formula 1:

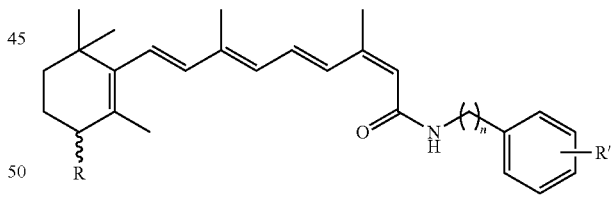

Formula 1 wherein R is a heteroaryl group,
wherein R' is a hydrogen, a halide, a hydroxyl group, an alkyl group, an ester group, an ether group, a benzyl group, a thio group, a Weinreb amide group, or a heterocyclic group, and
wherein n is an integer between 0 and 6, and
wherein when R' is the hydroxyl group, the compound is not (2Z, 4E, 6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide.

2. The process as claimed in claim 1, wherein the process is for the treatment of breast cancer or prostate cancer.

3. The process as claimed in claim 2, wherein R is an imidazole, and wherein the compound is selected from the following:

(2Z,4E,6E,8E)-9-(3-(1H-imidazol-1-yl)-2,6,6-trimethyl-cyclohex-1-en-1-yl)-3, 7-dimethyl-N-phenylnona-2,4,6,8-tetraenamide;

(2Z,4E,6E,8E)-9-(3-(1H-imidazol-1-yl)-2,6,6-trimethyl-cyclohex-1-en-1-yl)-N-(2-hydroxyphenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-fluorophenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorophenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-benzyl-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-hydroxybenzyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-fluorobenzyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorobenzyl)-3,7-dimethylnona-2,4,6,8-tetraenamide; and (2Z,4E,6E,8E)-9-(3-(1H-imidazol-1-yl)-2,6,6-trimethyl-cyclohex-1-en-1-yl)-N-(4-hydroxyphenethyl)-3,7-dimethylnona-2,4,6,8-tetraenamide.

4. The process as claimed in claim 3, wherein the compound is selected from the following:

(2Z,4E,6E,8E)-9-(3-(1H-imidazol-1-yl)-2,6,6-trimethyl-cyclohex-1-en-1-yl)-3,7-dimethyl-N-phenylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorophenyl)-3,7-dimethylnona-2,4,6,8-tetraenamide; and (2Z,4E,6E,8E)-9-(3-(1H-imidazol-1-yl)-2,6,6-trimethyl-cyclohex-1-en-1-yl)-N-(4-hydroxybenzyl)-3,7-dimethylnona-2,4,6,8-tetraenamide.

5. The process as claimed in claim 1, wherein R is an imidazole, and R' is hydrogen, fluorine, or a hydroxyl group, and n is 0, 1, or 2.

6. The process as claimed in claim 2, wherein R is a pyridine or a derivative thereof, and the compound is selected from the following:

(2Z,4E,6E,8E)-3,7-dimethyl-N-phenyl-9-(2,6,6-trimethyl-3-(pyridin-3-yl) cyclohexa-1,3-dien-1-yl)nona-2,4,6,8-tetraenamide;

(2Z,4E,6E,8E)-N-(4-hydroxybenzyl)-3,7-dimethyl-9-(2,6,6-trimethyl-3-(pyridin-3-yl)cyclohexa-1,3-dien-1-yl)nona-2,4,6,8-tetraenamide; and (2Z,4E,6E,8E)-N-(4-hydroxyphenethyl)-3,7-dimethyl-9-(2,6,6-trimethyl-3-(pyridin-3-yl)cyclohexa-1,3-dien-1-yl)nona-2,4,6,8-tetraenamide.

7. The process as claimed in claim 2, wherein R is a pyrimidine or a derivative thereof, and the compound is selected from the following:

(2Z,4E,6E,8E)-3,7-dimethyl-N-phenyl-9-(2,6,6-trimethyl-3-(pyrimidin-5-yl)cyclohexa-1,3-dien-1-yl)nona-2,4,6,8-tetraenamide;

(2Z,4E,6E,8E)-N-(4-hydroxybenzyl)-3,7-dimethyl-9-(2,6,6-trimethyl-3-(pyrimidin-5-yl)cyclohexa-1,3-dien-1-yl)nona-2,4,6,8-tetraenamide; and (2Z,4E,6E,8E)-N-(4-hydroxyphenethyl)-3,7-dimethyl-9-(2,6,6-trimethyl-3-(pyrimidin-5-yl)cyclohexa-1,3-dien-1-yl)nona-2,4,6,8-tetraenamide.

8. A process for treatment of breast cancer, prostate cancer, bladder cancer, pancreatic cancer, hepatocellular carcinoma, benign prostatic hyperplasia, Kennedy's disease, or hematologic cancer, comprising administering to a subject in need thereof a pharmaceutical composition comprising as an active ingredient a compound having the following Formula 1:

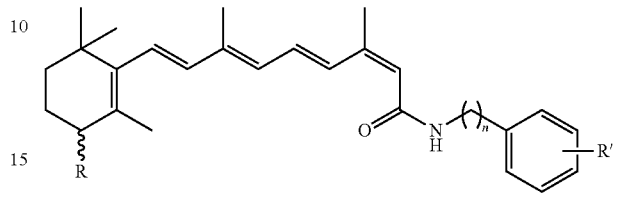

Formula 1 wherein R is a substituted or unsubstituted phenyl group,
wherein R' is a hydroxyl group in the para position,
wherein n is 0, 1, or 2, and
wherein when R' is the hydroxyl group, the compound is not (2Z,4E,6E,8E-9-(3-(1H-imidazol-1-yl)-2,6,6-trimethylcyclohex-1-en-1-yl)-N-(4-hydroxyphenyl)-3,7-dimethylnona-2,4,6,8-tetraenamide.

9. The process as claimed in claim 8, wherein the process is for the treatment of breast cancer or prostate cancer.

10. The process as claimed in claim 9, wherein R is a substituted phenyl group, and the compound is selected from the following:

(2Z,4E,6E,8E)-N-(4-hydroxybenzyl)-9-(3'-methoxy-2,4,4-trimethyl-4,5-dihydro-[1,1'-biphenyl]-3-yl)-3,7-dimethylnona-2,4,6,8-tetraenamide; and (2Z,4E,6E,8E)-N-(4-hydroxyphenethyl)-9-(3'-methoxy-2,4,4-trimethyl-4,5-dihydro-[1,1'-biphenyl]-3-yl)-3,7-dimethylnona-2,4,6,8-tetraenamide.

11. A process for treatment of a Mnk 1-, Mnk 2-, and/or androgen receptor-associated condition, comprising administering to a subject in need thereof a pharmaceutical composition comprising as an active ingredient a compound having the following Formula 1:

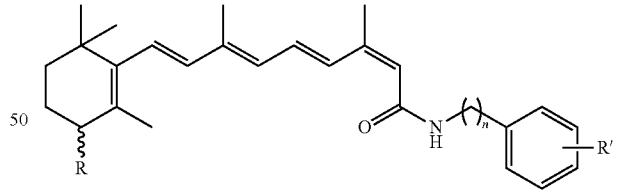

Formula 1 wherein R is a heteroaryl group or a phenyl group,
wherein R' is a hydrogen, a halide, a hydroxyl group, an alkyl group, an ester group, an ether group, a benzyl group, a thio group, a Weinreb amide group, or a heterocyclic group,
wherein n is an integer between 0 and 6, and
wherein when R' is the hydroxyl group, the compound is not (2Z,4E,6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide.

12. The process as claimed in claim 11, wherein R is an imidazole, and wherein the compound is selected from the following:

(2Z,4E,6E,8E)-9-(3-(1H-imidazol-1-yl)-2,6,6-trimethyl-cyclohex-1-en-1-yl)-3,7-dimethyl-N-phenylnona-2,4,6,8-tetraenamide;

(2Z,4E,6E,8E)-9-(3-(1H-imidazol-1-yl)-2,6,6-trimethyl-cyclohex-1-en-1-yl)-N-(2-hydroxyphenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-fluorophenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorophenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-benzyl-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-hydroxybenzyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-fluorobenzyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorobenzyl)-3,7-dimethylnona-2,4,6,8-tetraenamide; and (2Z,4E,6E,8E)-9-(3-(1H-imidazol-1-yl)-2,6,6-trimethyl-cyclohex-1-en-1-yl)-N-(4-hydroxyphenethyl)-3,7-dimethylnona-2,4,6,8-tetraenamide.

13. The process as claimed in claim 12, wherein the compound is selected from the following:

(2Z,4E,6E,8E)-9-(3-(1H-imidazol-1-yl)-2,6,6-trimethyl-cyclohex-1-en-1-yl)-3,7-dimethyl-N-phenylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorophenyl)-3,7-dimethylnona-2,4,6,8-tetraenamide; and (2Z,4E,6E,8E)-9-(3-(1H-imidazol-1-yl)-2,6,6-trimethyl-cyclohex-1-en-1-yl)-N-(4-hydroxybenzyl)-3,7-dimethylnona-2,4,6,8-tetraenamide.

14. The process as claimed in claim 11, wherein the Mnk 1-, Mnk 2-, and/or androgen receptor-associated condition is breast cancer or prostate cancer.

15. A process for inhibiting at least one of (i) mitogen-activated protein kinase (MAPK)-interacting kinase (Mnk)-driven phosphorylation of eukaryotic translation initiation factor 4E (eIF4E) and (ii) androgen receptor signaling pathway, comprising administering a therapeutically effective amount of a compound having the following Formula 1:

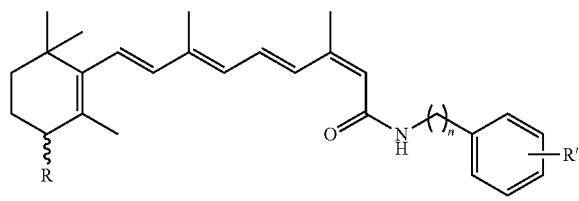

Formula 1 wherein R is a heteroaryl group or a phenyl group,
wherein R' is a hydrogen, a halide, a hydroxyl group, an alkyl group, an ester group, an ether group, a benzyl group, a thio group, a Weinreb amide group, or a heterocyclic group, wherein n is an integer between 0 and 6, and
wherein when R' is the hydroxyl group, the compound is not (2Z,4E,6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide.

16. The process as claimed in claim 15, wherein R is an imidazole, and wherein the compound is selected from the following:

(2Z,4E,6E,8E)-9-(3-(1H-imidazol-1-yl)-2,6,6-trimethyl-cyclohex-1-en-1-yl)-3,7-dimethyl-N-phenylnona-2,4,6,8-tetraenamide;

(2Z,4E,6E,8E)-9-(3-(1H-imidazol-1-yl)-2,6,6-trimethyl-cyclohex-1-en-1-yl)-N-(2-hydroxyphenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-fluorophenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorophenyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-benzyl-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-hydroxybenzyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(4-fluorobenzyl)-3,7-dimethylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorobenzyl)-3,7-dimethylnona-2,4,6,8-tetraenamide; and (2Z,4E,6E,8E)-9-(3-(1H-imidazol-1-yl)-2,6,6-trimethyl-cyclohex-1-en-1-yl)-N-(4-hydroxyphenethyl)-3,7-dimethylnona-2,4,6,8-tetraenamide.

17. The process as claimed in claim 16, wherein the compound is selected from the following:

(2Z,4E,6E,8E)-9-(3-(1H-imidazol-1-yl)-2,6,6-trimethyl-cyclohex-1-en-1-yl)-3,7-dimethyl-N-phenylnona-2,4,6,8-tetraenamide;

(2Z,4E,6E,8E)-9-(3-(1H-imidazol-1-yl)-2,6,6-trimethyl-cyclohex-1-en-1-yl)-N-(3-fluorophenyl)-3,7-dimethylnona-2,4,6,8-tetraenamide; and (2Z,4E,6E,8E)-9-(3-(1H-imidazol-1-yl)-2,6,6-trimethyl-cyclohex-1-en-1-yl)-N-(4-hydroxybenzyl)-3,7-dimethylnona-2,4,6,8-tetraenamide.

18. A process for treatment of a dermatological condition, comprising administering to a subject in need thereof a pharmaceutical composition comprising as an active ingredient a compound having the following Formula 1:

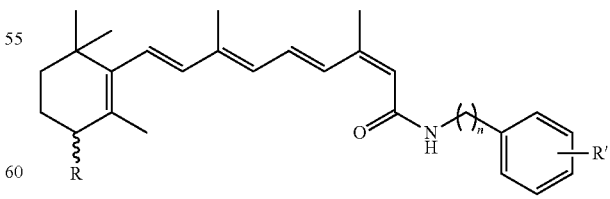

Formula 1 wherein R is a heteroaryl group or a phenyl group,
wherein R' is a hydrogen, a fluorine, or a hydroxyl group,
wherein n is 0, 1, or 2, and
wherein when R' is the hydroxyl up, the compound is not (2Z,4E,6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide.

19. The process as claimed in claim 18, wherein R is an imidazole, and wherein the compound is selected from the following:
- (2Z,4E,6E,8E)-9-(3-(1H-imidazol-1-yl)-2,6,6-trimethylcyclohex-1-en-1-yl)-3,7-dimethyl-N-phenylnona-2,4,6,8-tetraenamide;
- (2Z,4E,6E,8E)-9-(3-(1H-imidazol-1-yl)-2,6,6-trimethylcyclohex-1-en-1-yl)-N-(2-hydroxyphenyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(4-fluorophenyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(3-fluorophenyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-benzyl-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(4-hydroxybenzyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(4-fluorobenzyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(3-fluorobenzyl)-3,7-dimethylnona-2,4,6,8-tetraenamide; and
- (2Z,4E,6E,8E)-9-(3-(1H-imidazol-1-yl)-2,6,6-trimethylcyclohex-1-en-1-yl)-N-(4-hydroxyphenethyl)-3,7-dimethylnona-2,4,6,8-tetraenamide.

20. The process as claimed in claim 19, wherein the compound is selected from the following:
- (2Z,4E,6E,8E)-9-(3-(1H-imidazol-1-yl)-2,6,6-trimethylcyclohex-1-en-1-yl)-3,7-dimethyl-N-phenylnona-2,4,6,8-tetraenamide;
- (2Z,4E,6E,8E)-9-(3-(1H-imidazol-1-yl)-2,6,6-trimethylcyclohex-1-en-1-yl)-N-(3-fluorophenyl)-3,7-dimethylnona-2,4,6,8-tetraenamide; and
- (2Z,4E,6E,8E)-9-(3-(1H-imidazol-1-yl)-2,6,6-trimethylcyclohex-1-en-1-yl)-N-(4-hydroxybenzyl)-3,7-dimethylnona-2,4,6,8-tetraenamide.

21. A compound, or a pharmaceutically acceptable salt thereof, having the following Formula 1:

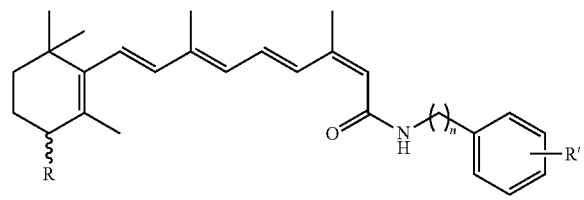

Formula 1 wherein R is a heteroaryl group or a phenyl group,
wherein R' is a hydrogen, a halide, a hydroxyl group, an alkyl group, an ester group, an ether group, a benzyl group, a thio group, a Weinreb amide group, or a heterocyclic group, wherein n is an integer between 0 and 6, and
wherein when R' is the hydroxyl group, the compound is not (2Z,4E,6E,8E)-9-(3-(1H-imidazol-1-yl)-2,6,6-trimethylcyclohex-1-en-1-yl)-N-(4-hydroxyphenyl)-3,7-dimethylnona-2,4,6,8-tetraenamide.

22. The compound as claimed in claim 21, wherein R is an imidazole, and wherein the compound is selected from the following:
- (2Z,4E,6E,8E)-9-(3-(1H-imidazol-1-yl)-2,6,6-trimethylcyclohex-1-en-1-yl)-3,7-dimethyl-N-phenylnona-2,4,6,8-tetraenamide;
- (2Z,4E,6E,8E)-9-(3-(1H-imidazol-1-yl)-2,6,6-trimethylcyclohex-1-en-1-yl)-N-(2-hydroxyphenyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(4-fluorophenyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(3-fluorophenyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-benzyl-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(4-hydroxybenzyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(4-fluorobenzyl)-3,7-dimethylnona-2,4,6,8-tetraenamide;
- (2Z,4E,6E,8E)-9-(3-(1H-imidazol-1-yl)-2,6,6-trimethylcyclohex-1-en-1-yl)-N-(3-fluorobenzyl)-3,7-dimethylnona-2,4,6,8-tetraenamide; and
- (2Z,4E,6E,8E)-9-(3-(1H-imidazol-1-yl)-2,6,6-trimethylcyclohex-1-en-1-yl)-N-(4-hydroxyphenethyl)-3,7-dimethylnona-2,4,6,8-tetraenamide.

23. The compound as claimed in claim 22, wherein R is an imidazole and wherein the compound is selected from the following:
- (2Z,4E,6E,8E)-9-(3-(1H-imidazol-1-yl)-2,6,6-trimethylcyclohex-1-en-1-yl)-3,7-dimethyl-N-phenylnona-2,4,6,8-tetraenamide;
- (2Z,4E,6E,8E)-9-(3-(1H-imidazol-1-yl)-2,6,6-trimethylcyclohex-1-en-1-yl)-N-(3-fluorophenyl)-3,7-dimethylnona-2,4,6,8-tetraenamide; and
- (2Z,4E,6E,8E)-9-(3-(1H-imidazol-1-yl)-2,6,6-trimethylcyclohex-1-en-1-yl)-N-(4-hydroxybenzyl)-3,7-dimethylnona-2,4,6,8-tetraenamide.

24. A pharmaceutical composition for treatment of breast cancer or prostate cancer, comprising a therapeutically effective amount of the compound as claimed in claim 21.

25. The pharmaceutical composition for treatment of a Mnk 1-, Mnk 2-, and/or androgen receptor-associated condition, comprising a therapeutically effective amount of the compound as claimed in claim 21, wherein the Mnk 1-, Mnk 2-, and/or androgen receptor-associated condition is selected from the group consisting of breast cancer or prostate cancer, bladder cancer, pancreatic cancer, hepatocellular carcinoma, benign prostatic hyperplasia, Kennedy's disease, and hematologic cancer.

26. A pharmaceutical composition for treatment of a dermatological condition, comprising a therapeutically effective amount of the compound as claimed in claim 21.

* * * * *